(12) United States Patent
Zhou et al.

(10) Patent No.: US 9,932,610 B2
(45) Date of Patent: Apr. 3, 2018

(54) METHODS OF MAKING VANILLIN VIA THE MICROBIAL FERMENTATION OF FERULIC ACID FROM EUGENOL USING A PLANT DEHYDROGENASE

(71) Applicant: BGN TECH LLC, Rancho Santa Margarita, CA (US)

(72) Inventors: Rui Zhou, Acton, MA (US); Xiaodan Yu, Lexington, MA (US)

(73) Assignee: BGN TECH LLC, Santa Margarita, CA (US)

( * ) Notice: Subject to any disclaimer, the term of this patent is extended or adjusted under 35 U.S.C. 154(b) by 0 days.

(21) Appl. No.: 15/033,980

(22) PCT Filed: Nov. 4, 2014

(86) PCT No.: PCT/US2014/063952
§ 371 (c)(1),
(2) Date: May 3, 2016

(87) PCT Pub. No.: WO2015/066722
PCT Pub. Date: May 7, 2015

(65) Prior Publication Data
US 2016/0312250 A1   Oct. 27, 2016

Related U.S. Application Data

(60) Provisional application No. 61/899,456, filed on Nov. 4, 2013.

(51) Int. Cl.
| | | |
|---|---|---|
| *C12N 9/02* | (2006.01) | |
| *C12N 9/04* | (2006.01) | |
| *C12N 1/20* | (2006.01) | |
| *C12P 7/00* | (2006.01) | |
| *C12P 7/02* | (2006.01) | |
| *C12P 7/22* | (2006.01) | |
| *C07H 21/04* | (2006.01) | |
| *C07K 1/00* | (2006.01) | |
| *C12P 7/24* | (2006.01) | |
| *C12P 7/40* | (2006.01) | |
| *C12P 7/42* | (2006.01) | |
| *C12N 15/70* | (2006.01) | |

(52) U.S. Cl.
CPC ............... *C12P 7/24* (2013.01); *C12N 15/70* (2013.01); *C12P 7/22* (2013.01); *C12P 7/40* (2013.01); *C12P 7/42* (2013.01)

(58) Field of Classification Search
CPC ...... C12P 7/22; C12P 7/24; C12P 7/42; C12P 7/40; C12N 15/70
USPC .... 435/189, 190, 243, 252.8, 132, 155, 156; 536/23.1, 23.2; 530/350
See application file for complete search history.

(56) References Cited

U.S. PATENT DOCUMENTS 6,818,752 B2 * 11/2004 Rozzell, Jr. ............ C07K 14/21
435/183
9,567,618 B2 *  2/2017 Lambrecht ........... C12N 9/0008

OTHER PUBLICATIONS

Baucher et al., Down-regulation of cinnamyl alcohol dehydrogenase in transgenic alfalfa (Medicago sativa L.) and the effect of lignin composition and digestibility. Plant Mol. Biol., 1999, vol. 39: 437-447.*
Sibout et al., Cinnamyl alcohol dehydrogenase-C and -D are the primary genes involved in lignin biosynthesis in the floral stem of arabidopsis. The Plant Cell, 2005, vol. 17: 2059-2076.*
Botosa et al., Quantitative isotopic 13C nuclear magnetic resonance at natural abundance to probe enzyme reaction mechanisms via site-specific isotope fractionation: The case of the chain-shortening reaction for the conversion of ferulic acid to vanillin. Analytical Biochem., 2009, vol. 393: 182-188.*
Overhage et al., Highly efficient bitransformation of eugenol to ferulic acid and further coversion to vanillin in recombiant strains of *Escherichia coli* Appl. Environ. Microbiol., 2003, vol. 69 (11) : 6569-6576.*
Tenailleau et al., Authentication of the origin of vanillin using quantitative natural abundance 13C NMR. J. Agric. Food Chem., 2004, vol. 52: 7782-7787.*
Lambert et al., "Production of ferulic acid and coniferyl alcohol by conversion of eugenol using a recombinant strain of *Saccharomyces cerevisiae*", Flavour and Fragrance Journal, 29:14-21 (2013).
Zhao et al., "Loss of function of cinnamyl alcohol dehydrogenase 1 leads to unconventional lignin and a temperature-sensitive growth defect in Medicago truncatula", PNAS, 110:13660-13665 (2013).
Cheng et al., "Purification and enzymatic characterization of alcohol dehydrogenase from *Arabidopsis thaliana*", Protein Expression and Purification, 90:74-77 (2013).
Kaur et al., "Biotechnological and molecular approaches for vanillin production: A review", Applied Biochemistry and Biotechnology, vol. 169: 1353-1372 (2013).
Graf et al., "Genetic engineering of Pseudomonas putida KT2440 for rapid and high-yield production of vanillin from ferulic acid", Applied Microbiology and Biotechnology, 98: 137-149 (2013).
Mishra et al., "Production of natural value-added compounds: an insight into the eugenol biotransformation pathway", Journal of Industrial Microbiology and Biotechnology, 40: 545-550 (2013).
Ashengroph et al., "Pseudomonas resinovorans SPR1, a newly isolated strain with potential of transforming eugenol to vanillin and vanillic acid", New Biotechnology, 28: 656-664 (2011).
Converti et al., "Microbial production of biovanillin", Brazilian Journal of Microbiology, vol. 41: 519-530 (2010).

* cited by examiner

*Primary Examiner* — Ganapathirama Raghu
(74) *Attorney, Agent, or Firm* — Nixon Peabody LLP; David S. Resnick

(57) ABSTRACT

A bioconversion method of making vanillin including expressing VaoA gene in a mixture, expressing MtSAD1 gene in the mixture, feeding eugenol to the mixture, and converting ferulic acid to vanillin by incubating with a microbial *Amycolatopsis* sp. strain (Zhp06) and/or a recombinant *E. coli* strain.

9 Claims, 12 Drawing Sheets
(9 of 12 Drawing Sheet(s) Filed in Color)

METHODS OF MAKING VANILLIN VIA THE MICROBIAL FERMENTATION OF FERULIC ACID FROM EUGENOL USING A PLANT DEHYDROGENASE

CROSS-REFERENCE TO RELATED APPLICATIONS

This Application is a 35 U.S.C. § 371 National Phase Entry Application of International Application No. PCT/US2014/063952 filed Nov. 4, 2014, which designates the U.S. and claims the benefit under 35 U.S.C. § 119(e) of U.S. Provisional Application No. 61/899,456 filed Nov. 4, 2013, the contents of each of which are incorporated herein by reference in their entirety entireties.

SEQUENCE LISTING

The instant application contains a Sequence Listing which has been submitted electronically in ASCII format and is hereby incorporated by reference in its entirety. Said ASCII copy, created on Dec. 2, 2014, is named 070946-081701-PCT_SL.txt and is 42,009 bytes in size.

FIELD OF DISCLOSURE

The present disclosure relates generally to methods and/or materials for utilizing a plant dehydrogenase to catalyze the bioconversion of eugenol to ferulic acid in bacteria, yeast or other cellular systems. It also relates to the production of vanillin, vanillin as produced using such methods and materials and the authentication of the vanilla product as a natural vanilla product.

BACKGROUND

Vanilla flavours are among some of the most frequently used flavours worldwide. They are used for the flavouring of numerous foods such as ice-cream, dairy products, desserts, confectionary, bakery products and spirits. They are also used in perfumes, pharmaceuticals and personal hygiene products.

Natural vanilla flavour has been obtained traditionally from the fermented pods of Vanilla orchids. It is formed mainly after the harvest during several weeks of a drying and fermentation process of the beans by hydrolysis of the vanillin glucoside that is present in the beans. The essential aromatic substance of vanilla flavour is vanillin (4-hydroxy-3-methoxybenzaldehyde).

Apart from natural vanilla flavor obtained from fermented vanilla pods, biotech and chemical synthetic processes have also been developed to produce biotechnologically and synthetically produced vanillin which is also used for the flavouring of foods. Several potential feedstocks have been suggested for the production of natural vanillin. By way of example, it has been found that many substrates such as ferulic acid, lignin, vanillic acid, eugenol and isoeugenol can be transformed to vanillin using many diffident microorganisms. Some of the highest yields of vanillin are obtained using a *Streptomyces setonii* strain capable of converting ferulic acid to natural vanillin (see, for example, EP0885968B and Muheim and Lerch (1999) Appl Microbiol Biotechnol 51: 456-461). However, as ferulic acid (from rice hull starting material) is an expensive starting material there is a need to identify cheaper ferulic acid precursor starting materials and efficient bioconversion processes for making ferulic acid useful in the preparation of natural vanillin of high flavor quality.

According to legislation to regulate the sale of natural food products, only products obtained from plant and animal materials or obtained from microbial enzymatic biotransformations/biocatalysis can be identified as natural. This regulatory legislation can vary from country to country. By way of example, US natural vanillin is derived from eugenol by a process which is not accepted as natural in the EU. The launch of a natural vanillin product/food ingredient made from a new starting material in the EU is subject to close scrutiny to ensure compliance with the local regulatory legislation and to protect the consumer from a vanillin ingredient which has not been made using regulatory acceptable methods.

Given that the customer-led demand for natural vanilla flavour or for vanillin isolated from the vanilla beans is very high and that the processes for making synthetic vanillin are much less expensive than the traditional process, the problem of falsification and misleading information is a particularly large one. Consumer organisations regularly publish the results of studies on the genuineness of vanilla flavour declared as natural in foods. These evaluations are typically based on analytical results. However, it has become clear that interpretation of the analytical results without knowledge of the production conditions or influencing factors in particular cases can lead to false evaluations and the incorrect designation of a product as synthetic when in fact it may be produced from plant and animal materials or obtained from microbial enzymatic biotransformations/biocatalysis and is thus entitled to be deemed a natural product.

Because of the consumer led demand for natural products such as natural vanillin, there is an increasing need for the efficient production of natural vanillin by biotransformation/bioconversion processes which: (i) use raw materials of natural origin; and (ii) employs process steps which are compatible with the requirements for natural flavours as recognized by the industry and regulatory authorities. There is also a need for the assessment of suitable methods for authenticating that the end product is a true natural vanillin product. The present disclosure seeks to provide for such biosynthesis/bioconversion processes and methods.

SUMMARY

An object of the present disclosure is to provide for a process that can be scaled up to industrial levels for the bioconversion of eugenol into ferulic acid which can in turn be used for natural vanillin production.

The present disclosure is a method for the high-yield bioconversion of eugenol to ferulic acid utilizing bacteria or other cellular systems that employs the gene products of VaoA and MtSAD1. In addition, an aldehyde dehydrogenase expressed by an ADH gene, AtADH, is employed in the bacteria to increase efficiency in the bioconversion reaction. AtADH is cloned from *Arabidopsis*.

Applicants discovered that the gene product of MtSAD1 derived from a plant *Medicago truncatula* is bifunctional. Essentially, MtSAD1 possesses both activities of the gene products of calA and calB. As such, MtSAD1 can substitute for the expression products of calA and calB, thereby allowing a more efficient biosynthetic pathway for the production of ferulic acid. Again, the gene products from VaoA and MtSAD1 can convert eugenol to ferulic acid.

Another disclosure is a bioconversion/biosynthetic method of making ferulic acid comprising: expressing VaoA gene in bacteria, expressing MtSAD1 gene in the bacteria; growing the bacteria in medium, feeding eugenol to the bacteria, incubating the bacteria, and collecting ferulic acid.

An embodiment is a biosynthetic/bioconversion method of making ferulic acid comprising: expressing VaoA gene in bacteria, expressing MtSAD1 gene in the bacteria; growing the bacteria in medium, feeding eugenol to the bacteria, incubating the bacteria, and converting ferulic acid to vanillin.

An embodiment is a bioconversion method of making vanillin comprising expressing VaoA gene in a mixture, expressing MtSAD1 gene in the mixture; feeding eugenol to the mixture; and converting ferulic acid to vanillin.

According to another embodiment of the present disclosure, the bioconversion of ferulic acid to vanillin is carried out by an enzymatic and/or biochemical route and/or fermentation route. The enzymatic and/or biochemical route can be carried out in vitro or in vivo as part of the fermentation route.

According to a further embodiment of the present disclosure, a ferulic acid material is obtained with a $\delta^{13}C$ value range (of from about −25 to about −32‰) which is different from the $\delta^{13}C$ value for ferulic acid obtained from a natural plant source selected from rice, maize, sugar beet, wheat and curcumin (with a $\delta^{13}C$ value range for ferulic acid from maize from about −16 to −19‰ according to Cochennec C Perfumer & Flavourist (2013) 38; 20-27).

According to a further embodiment of the present disclosure, a vanillin material is obtained with a $\delta^{13}C$ value range (of from about −25 to about −32‰) which is different from the $\delta^{13}C$ value for vanillin obtained from a natural plant source selected from rice, maize, sugar beet, wheat and curcumin (with $\delta^{13}C$ value range for vanillin from rice of from about −38 to −35‰ according to Cochennec C Perfumer & Flavourist (2013) 38; 20-27).

There is also provided a ferulic acid product obtainable from bioconverted eugenol which is different from the known ferulic acid products (eg from C3, C4 and CAM plants including but not limited to rice, maize, sugar beet, wheat and curcumin) in terms of its $\delta^{13}C$ value range (of from about −25 to about −32‰) and is different from the known artificially and/or synthetically derived ferulic acid products (eg from lignin and/or guaiacol) when its $\delta^{13}C$ value range is considered in the context of an additional D-NMR value measurement (such as, for example, when its $\delta^{13}C$ value is measured either alone or in combination with a D-NMR value measurement).

There is also provided a vanillin product obtainable from bioconverted eugenol which is different from the known vanillin product (eg from C3, C4 and CAM plants including but not limited to rice, maize, sugar beet, wheat and curcumin) in terms of its $\delta^{13}C$ value range (of from about −25 to about −32‰) and is different from the known artificially and/or synthetically derived ferulic acid products (eg from lignin and/or guaiacol) when its $\delta^{13}C$ value range is considered in the context of an additional D-NMR value measurement (such as, for example, when its $\delta^{13}C$ value is measured either alone or in combination with a D-NMR value measurement).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the present disclosure, reference may be made to the accompanying drawings in which.

DETAILED DESCRIPTION OF THE DISCLOSURE

Figure 1:
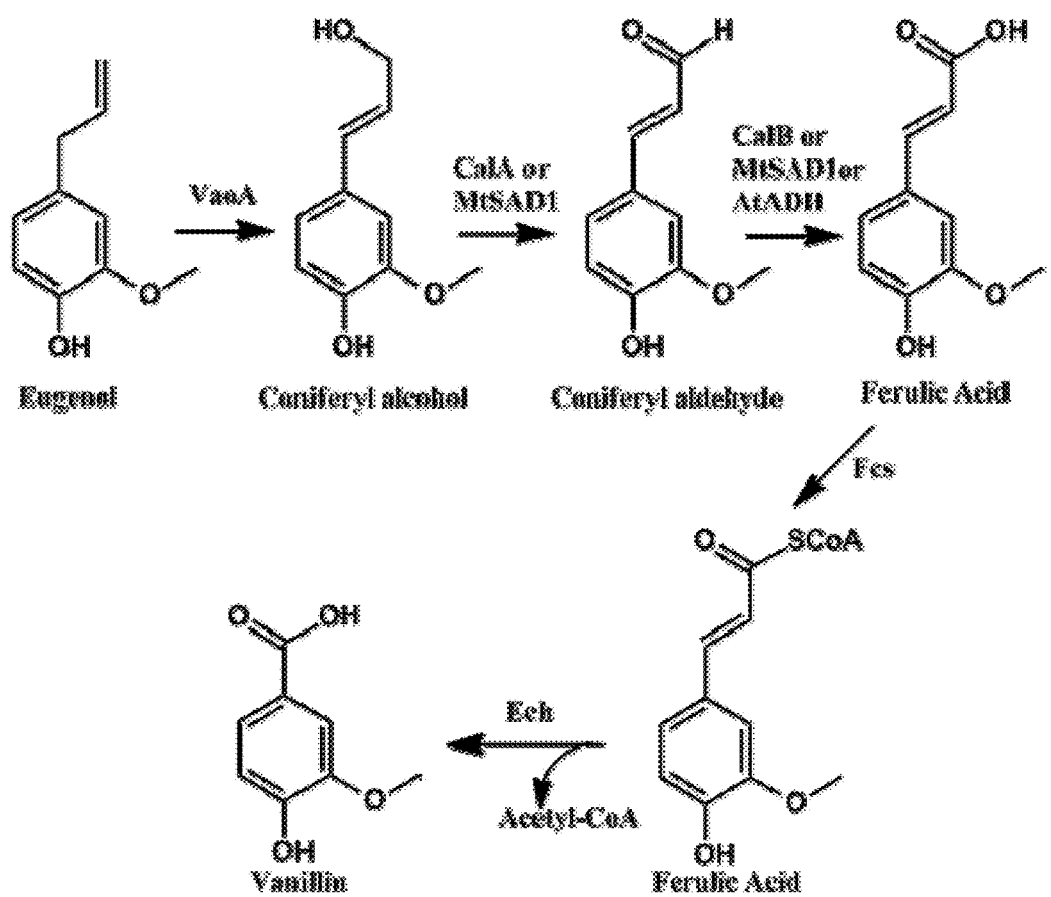
FIG. 1 is a schematic diagram illustrating the known and novel enzymatic pathways from eugenol to ferulic acid to vanillin.

The present disclosure provides a method for producing ferulic acid through the bioconversion of eugenol to ferulic acid and then further conversion to vanillin. The bioconversion can be mediated in a cellular system such as an *Escherichia coli* bacterium.

An embodiment of the present disclosure is a bioconversion method of making ferulic acid comprising expressing VaoA gene in a cellular system, expressing MtSAD1 gene in the cellular system, growing the cells in medium, feeding eugenol to the bacteria, incubating the bacteria, and collecting ferulic acid. The expression of the two aforementioned genes provides a method of making ferulic acid. Expression of other genes serves only to enhance the method. The bioconversion method can include the additional expression of the AtADH gene in the cellular system. The expression of AtADH enhances the bioconversion pathway for making ferulic acid. In addition, the calA gene can be further expressed in the cellular system to enhance the bioconversion pathway. Similarly, the calB gene can be further expressed in the cellular system for the same or similar purpose of enhancing the biosynthetic pathway. The cellular system can be any number of cellular systems that can facilitate the accumulation of ferulic acid. One embodiment uses a bacteria based cellular system, such as *E. coli*. Another embodiment utilizes an *Amycolatopsis* based cellular system. A further embodiment utilizes a yeast based cellular system. The expressed MtSAD1 is based on amino acid SEQ ID No. 1 or a variant, homologue, mutant, derivative or fragment thereof. In an alternative embodiment, the expressed MtSAD1 is based on amino acid with at least 95% identity to SEQ ID No. 1. Alternatively, the expressed MtSAD1 is based on amino acid with at least 90% identity to SEQ ID No. 1. In addition in one embodiment, the expressed MtSAD1 is based on an amino acid sequence expressed from *E. coli*.

The term "bioconversion" as used herein shall specifically refer to the cellular production of a product, e.g. by in vivo production in host cells in cell culture, specifically microbial host cells, which cellular production may be optionally combined with further biosynthetic production steps (e.g. in a host cell different from the prior one) and/or with reactions of chemical synthesis, e.g. by in vitro reactions. The term "bioconversion" is used interchangeably with the term "biotransformation" and/or "biosynthesis" or "biosynthetic" throughout the specification.

The term "Vanillyl-alcohol oxidase (VaoA)" as used herein refers to a covalent flavoprotein from *Penicillium simplicissimum* active on a wide range of para-substituted compounds. VaoA catalyses the oxidation of 4-alkylphenols including eugenol. The VaoA enzyme (EC 1.1.3.38) can also be expressed by host cells to oxidize any formed vanillyl alcohol into vanillin. VaoA enzymes are known in the art and include, but are not limited to enzymes from filamentous fungi such as *Fusarium onilifomis* (GENBANK Accession No. AFJ11909) and *Penicillium simplicissimum* (GENBANK Accession No. P56216; Benen, et al. (1998) J. Biol. Chem. 273:7865-72) and bacteria such as *Modestobacter marinus* (GENBANK Accession No. YP_006366868), *Rhodococcus jostii* (GENBANK Accession No. YPJ703243.1) and *R. opacus* (GENBANK Accession No. EHI39392). VaoA cDNA from *Penicillium simplicissimum* is also available at the National Centre for Biotechnology Information (GenBank) (available on the world wide web at www.ncbi.nlm.nih.gov) with the reference Y15627. VaoA nucleotide and amino acid sequences are provided herein as SEQ ID NO: 6 and SEQ ID NO: 5 respectively.

The method of the present disclosures utilises a dehydrogenase gene product of MtSAD1 derived from a plant *Medicago truncatula* which was discovered to be bifunctional. Essentially, MtSAD1 possessed both activities of the gene products of calA and calB. As such, MtSAD1 can substitute for the expression products of calA and calB, thereby potentially allowing a more efficient bioconversion/biosynthetic pathway for the production of ferulic acid from eugenol. Thus, the gene products from VaoA and MtSAD1 can bioconvert eugenol to ferulic acid. MtSAD1 nucleotide and amino acid sequences are provided herein as SEQ ID NO:2 and SEQ ID NO: 1 respectively.

Eugenol is known by its IUPAC name: 4-Allyl-2-methoxyphenol. It is a phenylpropene, an allyl chain-substituted guaiacol. Eugenol is a relatively inexpensive natural substrate that can be isolated from the essential oil of the clove tree *Syzygium aromaticum* on an industrial scale. Eugenol and isoeugenol are phenylpropenes, an allyl chain-substituted guaiacol. Eugenol is a member of the phenylpropanoids class of chemical compounds. It is a clear to pale yellow oily liquid extracted from certain essential oils especially from clove oil, nutmeg, cinnamon, basil and bay leaf. It is slightly soluble in water and soluble in organic solvents. It has a spicy, clove-like aroma. It is present in concentrations of 80-90% in clove bud oil and at 82-88% in clove leaf oil.

Ferulic acid is known chemically by its IUPAC name (E)-3-(4-hydroxy-3-methoxy-phenyl)prop-2-enoic acid. It is also known as Ferulate, Coniferic acid, and trans-ferulic acid (E)-ferulic acid. Ferulic acid is a hydroxycinnamic acid, a type of organic compound. It is an abundant phenolic phytochemical found in plant cell wall components such as arabinoxylans as covalent side chains. It is related to trans-cinnamic acid. As a component of lignin, ferulic acid is a precursor in the manufacture of other aromatic compounds.

AtADH is an aldehyde dehydrogenase of *Arabidopsis thaliana* (ALDH2C4). The AtADH nucleotide and amino acid sequence is available at the National Centre for Biotechnology Information (GenBank) (available on the world wide web at www.ncbi.nlm.nih.gov) with the reference NM_113359.3. AtADH nucleotide and amino acid sequences are provided herein as SEQ ID NO: 4 and SEQ ID NO: 3 respectively.

A coniferyl-alcohol dehydrogenase known as CalA (EC 1.1.1.194) is an enzyme that catalyzes the chemical reaction: coniferyl alcohol+NADP$^+$⇌coniferyl aldehyde+NADPH+H$^+$ Thus, the two substrates of this enzyme are coniferyl alcohol and NADP+, whereas its 3 products are coniferyl aldehyde, NADPH, and H$^+$. This enzyme belongs to the family of oxidoreductases, specifically those acting on the CH—OH group of donor with NAD$^+$ or NADP$^+$ as acceptor. The systematic name of this enzyme class is coniferyl-alcohol: NADP$^+$ oxidoreductase. This enzyme is also called CAD. A Coniferyl Alcohol Dehydrogenase nucleotide sequence is available at the National Centre for Biotechnology Information (GenBank) (available on the world wide web at www.ncbi.nlm.nih.gov) with the reference A92130. The nucleotide sequence and amino acid sequence for Coniferyl Alcohol Dehydrogenase (CaA) are also disclosed in EP0845532, US2002/0182697A1 and U.S. Pat. No. 6,524,831B2.

A coniferyl-aldehyde dehydrogenase known as CalB (EC 1.2.1.68) is an enzyme that catalyzes the chemical reaction: coniferyl aldehyde+H$_2$O+NAD(P)+⇌ferulate+NAD(P)H+2 H$^+$. The 4 substrates of this enzyme are coniferyl aldehyde, H$_2$O, NAD$^+$, and NADP$^+$, whereas its 4 products are ferulate, NADH, NADPH, and H$^+$. This enzyme belongs to the family of oxidoreductases, specifically those acting on the aldehyde or oxo group of donor with NAD+ or NADP+ as acceptor. The systematic name of this enzyme class is coniferyl aldehyde:NAD(P)+ oxidoreductase (see Achterholt S, Priefert H, Steinbuchel A (1998). "Purification and characterization of the coniferyl aldehyde dehydrogenase from *Pseudomonas* sp. Strain HR199 and molecular characterization of the gene". *J. Bacteriol.* 180 (17): 4387-91. PMC 107445. PMID 9721273). A Coniferyl Aldehyde Dehydrogenase nucleotide and amino acid sequence is available at the National Centre for Biotechnology Information (GenBank) (available on the world wide web at www.ncbi.nlm.nih.gov) with the reference AJ006231. The nucleotide sequence and amino acid sequence for Coniferyl Aldehyde Dehydrogenase (CalB) are also disclosed in EP0845532, US2002/0182697A1 and U.S. Pat. No. 6,524,831B2.

The term "gene" as used herein shall specifically refer to nucleic acid molecules or polynucleotides of the disclosure which can be DNA, cDNA, genomic DNA, synthetic DNA, or, RNA, and can be double-stranded or single-stranded, the sense and/or an antisense strand. The term "gene" shall particularly apply to the polynucleotide(s) as used herein, e.g. as full-length nucleotide sequence or fragments or parts thereof, which encodes a polypeptide with enzymatic activity, e.g. an enzyme of a metabolic pathway, or fragments or parts thereof, respectively.

The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein.

A ribonucleic acid (RNA) molecule can be produced by in vitro transcription. Segments of these molecules are also considered within the scope of the disclosure, and can be produced by, for example, the polymerase chain reaction (PCR) or generated by treatment with one or more restriction endonucleases. Segments of a nucleic acid molecule may be referred to as DNA fragments of a gene, in particular those that are partial genes. A fragment can also contain several open reading frames (ORF), either repeats of the same ORF or different ORF's. The term shall specifically refer to coding nucleotide sequences, but shall also include nucleotide sequences which are non-coding, e.g. untranscribed or untranslated sequences, or encoding polypeptides, in whole or in part. The genes as used herein, e.g. for assembly, diversification or recombination can be non-coding sequences or sequences encoding polypeptides or protein encoding sequences or parts or fragments thereof having sufficient sequence length for successful recombination events. More specifically, said genes have a minimum length of 3 bp, preferably at least 100 bp, more preferred at least 300 bp.

It will be apparent from the foregoing that a reference to an isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice. The term "isolated" polypeptide or peptide fragment as used herein refers to a polypeptide or a peptide fragment which either has no naturally-occurring counterpart or has been separated or purified from components which naturally accompany it, e.g., in plant. In addition, the isolated nucleic acid molecules of the disclosure encompass segments that are not found as such in the natural state.

An isolated polypeptide (or peptide fragment) of the disclosure can be obtained, for example, by extraction from a natural source (e.g., from a plant source); by expression of a recombinant nucleic acid encoding the polypeptide; or by chemical synthesis. A polypeptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

As used herein, the term "recombinant DNA" is either (1) a DNA that contains sequence not identical to that of any naturally occurring sequence, a polynucleotide or nucleic acid which is not naturally occurring, (e.g., is made by the artificial combination (eg artificial manipulation of isolated segments of nucleic acids, e.g., by genetic engineering techniques) of two otherwise separated segments of sequence through human intervention) or (2), in the context of a DNA with a naturally-occurring sequence (e.g., a cDNA or genomic DNA), a DNA free of at least one of the genes that flank the gene containing the DNA of interest in the genome of the organism in which the gene containing the DNA of interest naturally occurs The term "recombinant DNA" as used herein, specifically with respect to nucleic acid sequences shall also refer to nucleic acids or polynucleotides produced by recombinant DNA techniques, e.g. a DNA construct comprising a polynucleotide heterologous to a host cell, which is optionally incorporated into the host cell. A chimeric nucleotide sequence may specifically be produced as a recombinant molecule. The term "recombination" shall specifically apply to assembly of polynucleotides, joining together such polynucleotides or parts thereof, with or without recombination to achieve a cross-over or a gene mosaic. For example, it is performed to join together nucleic acid segments of desired functions to generate a desired combination of functions. A recombinant gene encoding a polypeptide described herein includes the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence.

The term "recombinant" as used herein, specifically with respect to enzymes shall refer to enzymes produced by recombinant DNA techniques, i.e., produced from cells transformed by an exogenous DNA construct encoding the desired enzyme. "Synthetic" enzymes are those prepared by chemical synthesis. A chimeric enzyme may specifically be produced as recombinant molecule. The term "recombinant DNA" therefore includes a recombinant DNA incorporated into a vector into an autonomously replicating plasmid or virus, or into the genomic DNA of a prokaryote or eukaryote (or the genome of a homologous cell, at a position other than the natural chromosomal location).

A further aspect of the present disclosure is a vector containing the polynucleotide(s) of the present disclosure or a protein encoded by a polynucleotide of the present disclosure The term "vector" refers to a protein or a polynucleotide or a mixture thereof which is capable of being introduced or of introducing the proteins and/or nucleic acid comprised into a cell. It is preferred that the proteins encoded by the introduced polynucleotide are expressed within the cell upon introduction of the vector. The diverse genes substrates may be incorporated into plasmids. The plasmids are often standard cloning vectors, e.g., bacterial multicopy plasmids. The substrates can be incorporated into the same or different plasmids. Often at least two different types of plasmid having different types of selectable markers are used to allow selection for cells containing at least two types of vector.

In a preferred embodiment the vector of the present disclosure comprises plasmids, phagemids, phages, cosmids, artificial mammalian chromosomes, knock-out or knock-in constructs, Synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

The term "recombinant host", also referred to as a "genetically modified host cell" denotes a host cell that comprises a heterologous nucleic acid.

In a further aspect the nucleic acid molecule(s) of the present disclosure is/are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression or which allow inducible expression like, for example, CUP-1 promoter, the tet-repressor as employed, for example, in the tet-on or tet-off systems, the lac system, the trp system regulatory elements. By way of example, Isopropyl β-D-1-thiogalactopyranoside (IPTG) is an effective inducer of protein expression in the concentration range of 100 μM to 1.0 mM. This compound is a molecular mimic of allolactose, a lactose metabolite that triggers transcription of the lac operon, and it is therefore used to induce protein expression where the gene is under the control of the lac operator. Another example of regulatory elements which induce protein expression is lactose.

As used herein, "operatively linked" means incorporated into a genetic construct so that expression control sequences effectively control expression of a coding sequence of interest.

Similarly, the nucleic acid molecule(s) of the present disclosure can form part of a hybrid gene encoding additional polypeptide sequences, for example, a sequence that functions as a marker or reporter. Examples of marker and reporter genes including beta-lactamase, chloramphenicol acetyltransferase (CAT), adenosine deammase (ADA), aminoglycoside phosphotransferase dihydrofolate reductase (DHFR), hygromycin-B-phosphotransferase (HPH), thymidine kinase (TK), lacZ (encoding beta. -galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

Another aspect of the present disclosure is a host cell genetically engineered with the polynucleotide or the vector as outlined above. The host cells that may be used for purposes of the disclosure include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the disclosure; simple eukaryotic cells like yeast (for example, *Saccharomyces* and *Pichia*), which can be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondrial DNA or can be maintained extrachromosomally like, for example, episomally or can be only transiently comprised in the cells.

Cells may be transfected with any one or more of the following nucleotide sequence as is well known in the art. For in vivo recombination, the gene to be recombined with the genome or other genes is used to transfect the host using standard transfection techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

A cell may be transformed by exogenous or heterologous DNA when such DNA has been introduced inside the cell. The transforming DNA may or may not be integrated, i.e. covalently linked into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

The present disclosure also features recombinant hosts. As used herein, the term recombinant host is intended to refer to a host, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. However, autonomous or replicative plasmids or vectors can also be used within the scope of this disclosure. Moreover, the present disclosure can be practiced using a low copy number, e.g., a single copy, or high copy number (as exemplified herein) plasmid or vector.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp, yeast host cells, such as *S. cerevisiae*, insect host cells, such as *Spodoptera frugiperda* or human host cells, such as HeLa and Jurkat.

Specifically, the cell is a eukaryotic cell, preferably a fungal, mammalian or plant cell, or prokaryotic cell. Suitable eukaryotic cells include, for example, without limitation, mammalian cells, yeast cells, or insect cells (including Sf9), amphibian cells (including melanophore cells), or worm cells including cells of *Caenorhabditis* (including

*Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include without limitation *E. coli*.

Preferably prokaryotes, such as *E. coli, Bacillus, Streptomyces*, or mammalian cells, like HeLa cells or Jurkat cells, or plant cells, like *Arabidopsis*, may be used.

Preferably the cell is an *Aspergillus* sp or a fungal cell, preferably, it can be selected from the group consisting of the genera *Saccharomyces, Candida, Kluyveromyces, Hansenula, Schizosaccaromyces, Yarrowia, Pichia* and *Aspergillus*.

Preferably the *E. coli* host cell is an *E. coli* host cell which is an *E. coli* host cell which is recognized by the industry and regulatory authorities (including but not limited to an *E. coli* K12 host cell).

One preferred host cell to use with the present disclosure is *E. coli*, which may be recombinantly prepared as described herein. Thus, the recombinant host may be *E. coli*. There are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

In one embodiment, the recombinant *E. coli* microorganism comprises VaoA, MtSAD1 and AtADH genes or functional equivalents/homologies thereof including but not limited to variants, homologues mutants, derivatives or fragments thereof.

Figure 2:
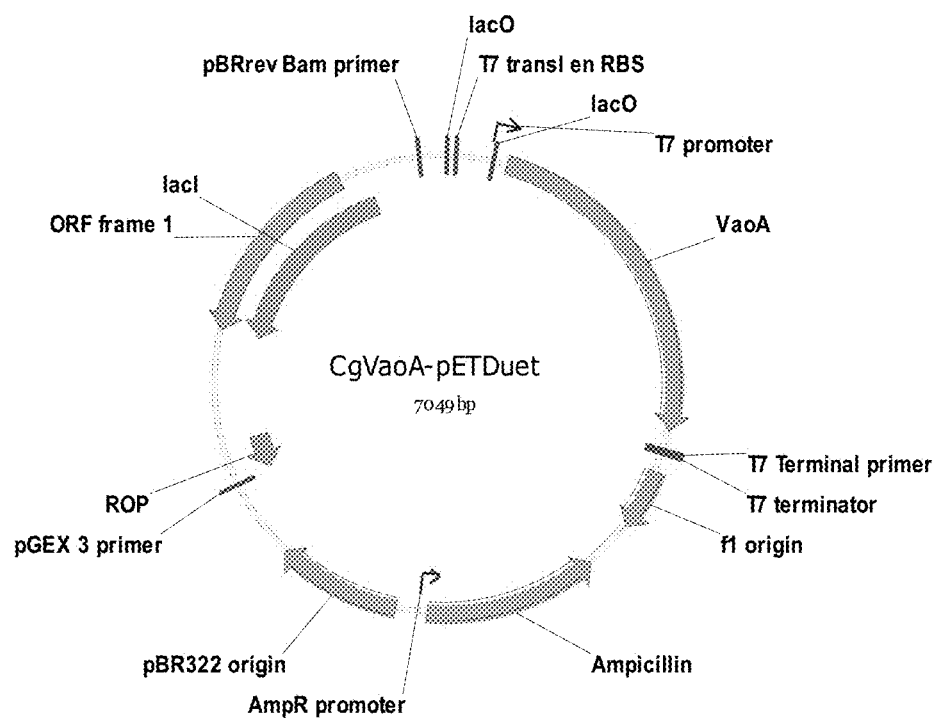
FIG. 2 provides a schematic diagram of a CgVaoA-pETDuet construct.

Preferably, the recombinant *E. coli* microorganism comprises a CgVaoA-pETDuet construct as provided in FIG. 2.

Figure 3:
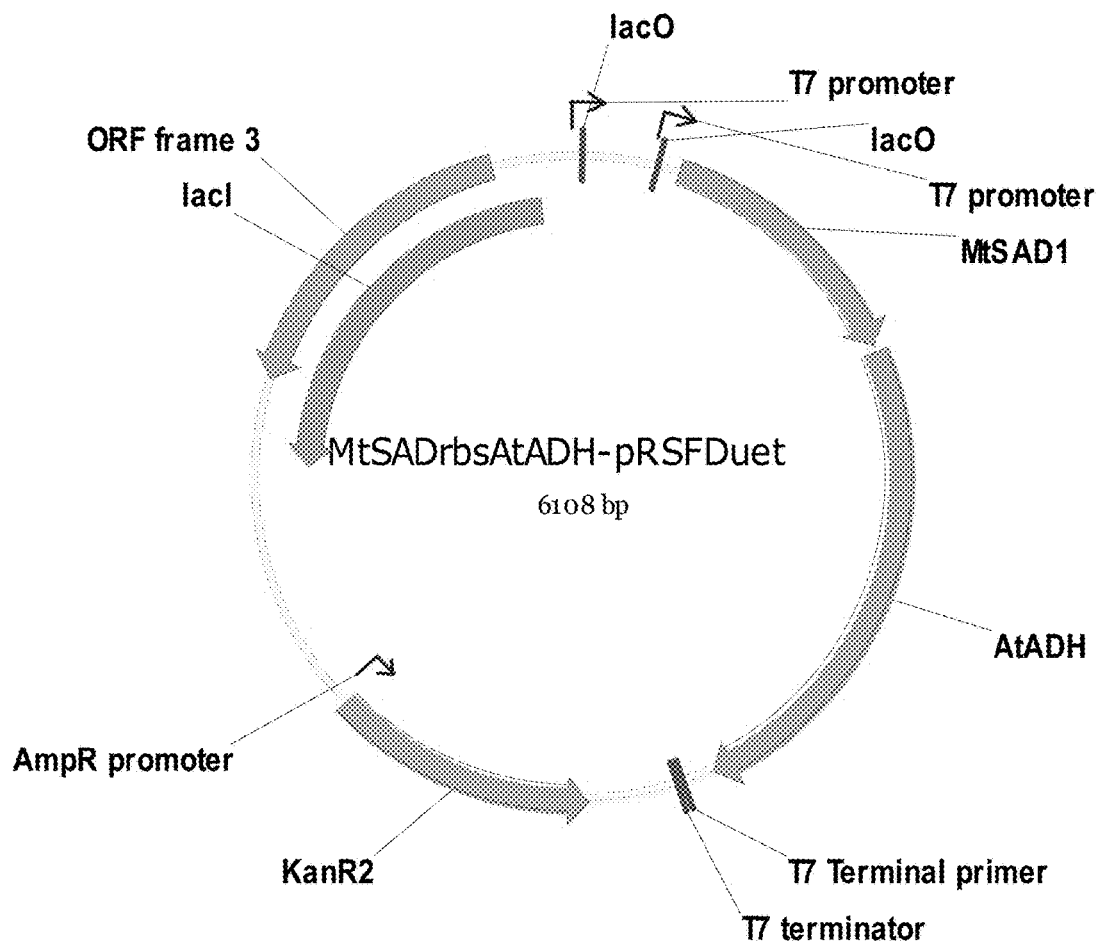
FIG. 3 provides a schematic diagram of a MtSADrbsAt-ADH-pRSFDuet construct.

Preferably, the recombinant *E. coli* microorganism comprises a MtSADrbsAtADH-pRSFDuet construct as provided in FIG. 3.

Preferably the recombinant *E. coli* strain comprises both plasmids CgVaoA-pETDuet and MtSADrbsAtADH-pRSFDuet which bioconverts eugenol to ferulic acid.

In another preferred embodiment, the recombinant *E. coli* microorganism comprises ech and fcs genes or functional equivalents/homologies thereof including but not limited to variants, homologues mutants, derivatives or fragments thereof.

Another preferred host cell to use with the present disclosure is *S. cerevisiae* which is a widely used chassis organism in synthetic biology. Thus, the recombinant host may be *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

The production of ferulic acid and coniferyl alcohol by conversion of eugenol using a recombinant strain of *Saccharomyces cerevisiae* has been disclosed in Lambert et al (2013) Flavour and Fragrance Journal DOI 10.1002/ffj.3173) (see, for example, U.S. Pat. No. 8,344,119B and/or EP2126059).

The term "cell" shall specifically include a single cell or cells cultivated in a cell culture, such as cell lines.

The term "production cell" as used herein shall specifically refer to a cell recombinantly engineered to produce a product of a production process or biosynthesis, e.g. a product of a metabolic pathway.

Once clones are selected that produce the desired products of bioconversion, the products are typically produced by a production host cell line on the large scale by suitable expression systems and fermentations, e.g. by microbial production in cell culture.

The term "cell line" as used herein refers to an established clone of a particular cell type that has acquired the ability to proliferate over a prolonged period of time. The term "host cell line" refers to a cell line as used for engineering and/or expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process or biosynthesis, such as a product of a metabolic pathway.

Alternatively any one or more of the following enzymes VAO, MtSAD1, AtADA, CalA, CalB, FCS and ECH can be expressed using stable or transient expression systems. The generation of a stable cell line is well known.

Recombinant host microorganisms described herein can be used in methods to produce ferulic acid/vanillin. For example, if the recombinant host is a microorganism, the method can include growing the recombinant microorganism in a culture medium under conditions in which ferulic acid and/or the vanillin biosynthesis genes are expressed.

The recombinant microorganism may be grown in a batch, fed batch or continuous process or combinations thereof. Typically, the recombinant microorganism is grown in a fermentor at a defined temperature (s) in the presence of a suitable nutrient source, e.g., a carbon source, for a desired period of time to bioconvert eugenol to ferulic acid/vanillin and to produce a desired amount of ferulic acid and/or vanillin.

The recombinant host cell microorganism may be cultured in a number of ways in order to provide cells suitable for the subsequent bioconversion step. Culturing is carried out under conditions yielding viable cells in all cases if such cells are to be used for the subsequent bioconversion step. Since the microorganisms applicable for the bioconversion step vary broadly (eg yeasts, bacteria and fungi), culturing conditions must, of course be adjusted to the specific requirements of each species and these conditions are well known and documented. Any of the art known methods for growing cells of recombinant host cell microorganisms may be used to produce the cells utilizable in the subsequent bioconversion step of the present disclosure.

Culturing of cells is performed, in a conventional manner. The culture medium contains a carbon source, at least one nitrogen source and inorganic salts, and yeast extract is added to it. The constituents of this medium can be the ones which are conventionally used for culturing the species of microorganism n question.

Carbon sources of use in the instant method include any molecule that can be metabolized by the recombinant host cell to facilitate growth and/or production of the vanillin and/or vanillin glucoside. Examples of suitable carbon sources include, but are not limited to, sucrose (e.g., as found in molasses), fructose, xylose, ethanol, glycerol, glucose, cellulose, starch, cellobiose or other glucose containing polymer.

In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

The suitability of the recombinant host cell microorganism for use in the present disclosure may be determined by simple test procedures using well known methods. For example, the microorganism to be tested may be propagated in a rich medium (e.g., LB-medium, Bacto-tryptone yeast extract medium, nutrient medium and the like) at a pH, temperature and under aeration conditions commonly used for propagation of the microorganism. The cells are harvested by centrifugation or filtration and are washed with the identical sterile medium containing no assimilable carbon source.

The washed cells are suspended in minimal medium (e.g., Mandels medium, MCGC medium, YNB medium) containing 0.1% eugenol plus 0.1% glucose, and the mixture is incubated with or without aeration (preferably with aeration by shaking at about 200 rpm) at 30 degrees C. Aliquots of supernatant are withdrawn from the incubation mixture at 12 hour intervals and are analyzed be HPLC for ferulic, the presence of which is indicative of eugenol conversion to ferulic acid.

In one embodiment of the present disclosure, a defined minimal medium such as M9A is used for cell cultivation.

The components of M9A medium comprise: 14 g/L $KH_2PO_4$, 16 g/L $K_2HPO_4$, 1 g/L $Na_3Citrate.2H_2O$, 7.5 g/L $(NH4)_2SO_4$, 0.25 g/L $MgSO_4.7H_2O$, 0.015 g/L $CaCl_2.2H_2O$, 5 g/L of glucose and 1.25 g/L yeast extract).

In one embodiment, when the medium composition used was M9A, an acceleration of the bioconversion is observed, especially as regards the bioconversion of ferulic acid to vanillic acid In another embodiment of the present disclosure, nutrient rich medium such as LB (Luria-Bertani) was used. The components of LB comprise: 10 g/L trptone, 5 g/L yeast extract, 5 g/L NaCl).

In another embodiment of the present disclosure, a Glucose Yeast Extract (GYE) medium is used. The components of TSB Medium comprise: Yeast extract, 8 g/L; glucose, 30 g/L; MgSO4.7H2O, 0.8 g/L; Na2HPO4*7H2O, 7.5 g/L; and KH2PO4, 1.0 g/L.

Other examples of Mineral Medium and M9 Mineral Medium are disclosed, for example, in U.S. Pat. No. 6,524,831B2 and US 2003/0092143A1.

In order to carry out the bioconversion steps, an aqueous solution containing eugenol and the cell culture medium is contacted with the recombinant host cell microorganism to form a bioconversion mixture which is maintained under conditions of pH, temperature, and agitation necessary to promote the conversion of eugenol to ferulic acid.

The term "mixture" is used interchangeably with the term "medium" in the present disclosure.

It is highly preferred that the bioconversion mixture also contain other substances necessary to promote the viability of the microorganism such as mineral salts, buffers, cofactors, nutrient substances and the like. The general requirements for the maintenance of viability of ferulic acid degrading microorganisms are well known. Specific requirements for maintaining the viability of specific microorganisms are also well documented in the literature or other otherwise easily determined by the skilled microbiologist. Preferably, the solution used for forming the bioconversion mixture consists of a minimal medium such as Mandels medium or MCGC medium to which is added eugenol and the recombinant host cell microorganism.

The mixture is then held at a pH and temperature necessary to promote ferulic acid and/or vanillin production. Preferred pH is between about pH 3 and about pH 7 and preferred temperature is between about 20 degrees C. and about 40 degrees C. Further, it is highly preferred that the bioconversion mixture contain a source of assimilable carbon for the recombinant host cell microorganism, for example, glucose, sucrose, fructose, maltose and the like. Use of an assimilable carbon source in the bioconversion mixture materially increases the yield of ferulic acid and/or vanillin. The most preferred carbon source is glucose.

Although conditions for maintaining cell viability must be maintained throughout the bioconversion step, it is not necessary that active cell growth occurs. It is in fact preferable that the recombinant host cells be in stationary phase for this step. It is also preferable that reducing conditions be maintained in the mixture during the bioconversion step. While absolute anaerobic conditions are not recommended, it is preferable that incorporation of oxygen into the bioconversion mixture through stirring or agitation be minimized to avoid oxidation of the vanillin, particularly when pH is greater than about 6.0. Oxygen may also be excluded, of course, by conducting the bioconversion step under inert atmosphere, e.g., under a nitrogen blanket.

Preferably the biotransformation/bioconversion mixture is a medium used as a culture medium, preferably containing a recombinant host cell/microorganism as described herein or mutants thereof.

The medium composition used for fed batch and continuous cultivation in well controlled bioreactors was as follows:

In some embodiments, ferulic acid is produced using whole cells that are fed raw materials that contain precursor molecules such as eugenol. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

The bioconversion methods of the present disclosure are carried out under conditions of time, temperature, pH, nutrient type and concentration, aeration conditions, methionine supplementation, and limited glucose concentrations, to provide maximal conversion of the eugenol source to vanillin. As described in detail in Example 1, in a preferred embodiment, a fed-batch fermentor is used to convert the eugenol source to ferulic acid followed by organic extraction of ferulic acid e.g., acidification of the fermentation broth and extraction with organic solvent or crystallization of the ferulic acid by pH change and not using an organic solvent extraction. The fed-batch fermentor process and organic extraction methods are known to those skilled in the art. As eugenol is toxic to cells, the eugenol is added slowly into the culture media over a 36-48-64 hour period in order to maintain the cellular integrity to sustain the reaction over a period of 36-48-64 hours. If the cells are lysed the reaction will stop and the yield will be very low. Accordingly, the eugenol is added repeatedly in small amounts so that conversion is completed before adding any new eugenol. The host cells are separated from the culture medium before adding an organic solvent to precipitate the solubilised ferulic acid or by adding acid (eg HCl) to precipitate the ferulic acid. Care is also taken to ensure a correct biomass which can affect the conversion rate of eugenol to ferulic acid.

Owing to the general toxicity displayed by many ferulic acid precursor starting materials for microorganisms, it may be necessary to limit the concentration of such in the bioconversion mixture. It is therefore preferred that the concentration of starting materials be limited at any given time during biotransformation. This is particularly true for those precursors which tend to be fat soluble (e.g., eugenol) as opposed to those with greater water solubility and lower toxicity such as for example, ferulic acid. Multiple additions of precursor may be made throughout the course of the bioconversion step in order to replace precursor as it is converted to vanillin.

In a preferred embodiment, the bioconversion mixture is maintained at a temperature of about 30 degrees C. to about 37 degrees C. and a pH of about 6.5 to about 7.5. It is preferred that the bioconversion mixture also contain other substances necessary to promote the viability of the recombinant microorganisms such as mineral salts, buffers, cofactors, nutrient substances and the like. The bioconversion mixture is preferably maintained in a steady state of dissolved oxygen (DO) concentration and thus is kept under glucose limited conditions, wherein the rate of glucose addition is determined by the level of dissolved oxygen concentration. The more general requirements for the maintenance of viability of microorganisms are well known and specific requirements for maintaining the viability of specific microorganisms are also well known as documented in the literature, or are otherwise easily determined by those skilled in the art. The ferulic acid may then be recovered from the bioconversion mixture by methods known in the art (e.g., organic extraction), and contacted with a second recombinant host cell produce vanillin.

After the recombinant microorganism has been grown in culture for the desired period of time, ferulic acid can then be recovered from the culture using various techniques known in the art, e.g., isolation and purification by extraction, vacuum distillation and multi-stage re-crystallization from aqueous solutions and ultrafiltration. By way of example, ferulic acid may be recovered by separating the culture broth from the cells and extracting it with an organic solvent, such as but not limited to ethyl acetate.

Preferably the purification involves the dissolution of ferulic acid in the purification fluid, and its separation from undissolved impurities.

The crude first material may be obtained by precipitation from a solution, preferably in a crystalline or macrocrystalline state. The solution may be a bioconversion/biotransformation medium, or may be derived from such a medium, e.g. by one or more steps such as removal of biocatalyst (which may be whole cells, cell parts, or immobilised enzyme), pasteurisation and concentration. The bioconversion/biotransformation medium is generally from a bioconversion/biotransformation process which produces vanillin, usually by the biotransformation of ferulic acid into vanillin.

In other embodiments, the ferulic acid is isolated as an extract from a recombinant host. In this respect, the ferulic acid may be isolated, but not necessarily purified to homogeneity.

In this regard, the term "isolated" relating to a bioconversion product means a product which has been separated or purified from other components which accompany it.

Typically, the bioconversion product is considered "isolated" when it is at least 70%, by dry weight, free from the proteins and other materials with which it is associated. Preferably, a the bioconversion product of the disclosure is at least 80%, more preferably at least 90%, and most preferably at least 99%, by dry weight. Thus, for example, a preparation of such of ferulic acid is at least 80%, more preferably at least 90%, and most preferably at least 99%, by dry weight.

In some embodiments, the ferulic acid is isolated and purified to homogeneity (e.g., at least 90%, 92%, 94%, 96%, or 98% pure). Desirably, the amount of ferulic acid produced can be from about 1 mg/l to about 20,000 mg/L (20 g/L) or higher.

For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 (1 g/l) to about 15,000 mg/L (15 g/l), or about 2,000 (2 g/l) to about 10,000 mg/L (10 g/l) or about 2,000 (2 g/l) to about 25,000 mg/L (25 g/l) or about 2,000 (2 g/l) to about 25,000 mg/L (25 g/l), 26,000 mg/L (26 g/l), 27,000 mg/L (27 g/l), 28,000 mg/L (28 g/l), 29,000 mg/L (29 g/l), 30,000 mg/L (30 g/l), of ferulic acid can be produced.

In general, longer culture times will lead to greater amounts of product. Thus, the recombinant microorganism can be cultured for from 1 day to 7 days, from 1 day to 5 days, from 1 day to 3 days, from 3 days to 5 days, about 3 days, about 4 days, or about 5 days.

Preferably ferulic acid at a concentration of at least 20 g/l is produced within a period of time of from 4 to 120 hours.

Preferably ferulic acid at a concentration of about 5-6 g/l is produced within a period of time of from about 4 to about 25 hours.

Preferably ferulic acid at a concentration of about 15-16 g/l is produced within a period of time of from about 4 to about 40 hours.

Preferably ferulic acid at a concentration of about 25-27 g/l is produced within a period of time of from about 4 to about 70 hours.

As Example 2 demonstrates, the present disclosure provides Ferulic acid (26 g/l) was recovered after 64 hours of incubation when the biotransformation/bioconversion method was scaled up to 30 L fermentation volume (in a 50 L fermentation vehicle).

Thus the present disclosure provides a method for making ferulic acid which is: (i) economically attractive, (ii) environmentally friendly; (iii) which utilises an abundant and a relatively inexpensive resource at the starting material; and (iv) which provides a high yield of ferulic acid.

A bioconversion/biotransformation process for converting eugenol to ferulic acid in a recombinant strain of *E. coli* is disclosed Preferably the recombinant host cell microorganism produces a medium containing at least 3 g/l, preferably at least 4 g/l, 5 g/l, 6 g/l, 7 g/l, 8 g/l, 9 g/l, 10 g/l, 11 g/l, 12 g/l, 13 g/l, 14 g/l, 15 g/l, 16 g/l, 17 g/l, 18 g/l, 19 g/l, 20 g/l, 21 g/l, 22 g/l, 23 g/l, 24 g/l, 25 g/l, 26 g/l, 27 g/l, 28 g/l, 29 g/l, 30 g/ of ferulic acid Ferulic acid production from eugenol, isoeugenol by different microorganisms was studied in the last decade. Eugenol is one of the most important raw materials for ferulic acid production and is the main constituent of oil extracted from the clove tree *Syzygium aromaticum*. Many studies have been carried out to elucidate the mechanisms of biotransformation of eugenol to ferulic acid that involves intermediates like eugenol epoxide, eugenol diol, coniferyl alcohol and coniferyl aldehyde catalysted by EhyAB, CalA and CalB enzymes. The pathway from Eugenol to ferulic acid (FIG. 1) was characterized in a strain of *Pseudomonas* (HR199) (Rabenhorst J Arch Microbiol Biotechnol (1996) 46: 470-474). The reactions are catalyzed successively by eugenol hydroxylase (ehyA and ehyB genes), coniferyl alcohol dehydrogenase (calA) and coniferyl aldehyde dehydrogenase (calB) (Priefert et al 1999 Arch Microbiol (1999) 172: 354-363). A vanillyl alcohol oxidase (VaoA) from

*Penicillum simplicissimum* can also oxidise eugenol producing coniferyl alcohol (Overhage et al (2003) Appl and Environ Microbiol 69(11) 6569-6576).

The eugenol hydroxylase encoded by the genes ehyAB derived from *Pseudomonas*, together with coniferyl alcohol dehydrogenase and coniferyl aldehyde dehydrogenase encoded by calA and calB, respectively also derived from *Pseudomonas*, was utilized initially by the Applicants to produce ferulic acid from eugenol in bacteria. Although eugenol hydroxylase together with coniferyl alcohol dehydrogenase and coniferyl aldehyde dehydrogenase proved successful in the microbial conversion of eugenol to ferulic acid, more effective enzymes were sought that could facilitate the process. Applicants also confirmed that the VaoA gene from *Penicillium simplicissimum*, which encodes vanillyl alcohol oxidase (VaoA), can catalyze the conversion of eugenol to coniferyl alcohol. This VaoA enzyme shares extensive regions of homology with the amino acid sequence of the flavoprotein subunit of eugenol hydroxylases. Vanillyl alcohol oxidase (VaoA)—in conjunction with coniferyl alcohol dehydrogenase and coniferyl aldehyde dehydrogenase—facilitates the bioconversion/biotransformation of eugenol to ferulic acid.

Overhage et al (2003 Appl and Env Microbiol 69(11) 6569-6576)) constructed a recombinant strain of *Escherichia coli* using Plac-based expression vector (pSKvaomP-calAmcalB) consisting of VaoA gene of *Penicillum simplicissimum* CBS 170.90 and CalA and CalB genes of *Pseudomonas* sp. HR199 which successfully converted eugenol to coniferyl alcohol, coniferyl aldehyde and finally to ferulic acid with a molar yield of 91% within 15 hours of incubation. Ferulic acid (14.7 g/l) was recovered after 30 hours of incubation (93.3%) molar yield when this biotransformation was scaled up to 30 L fermentation volume. No data/information was provided on whether the process could be enhanced to improve yields by extending the incubation time.

The present disclosure provides a bioconversion/biotransformation process for converting eugenol to ferulic acid in a recombinant strain of *E. coli*. The known bacterial CalA/CalB genes of *Pseudomonas* sp. HR199 (as disclosed in Overhage et al 2003 Appl and Env Microbiol 69(11) 6569-6576)) were replaced with plant based genes (MtSAD1 and AtADH1) which successfully converted eugenol to coniferyl alcohol, coniferyl aldehyde and finally to ferulic acid. Ferulic acid (26 g/l) was recovered after about 64 hours of incubation when this biotransformation was scaled up to 30 L fermentation volume. One advantage of the disclosed bioconversion method is that the fermentation and conversion could be carried out with high efficiency in a mineral culture medium (such as M9A medium) which is more cost effective than a rich culture medium (such as LB, TSB or TB or the like).

The successful development of a bioconversion process for making ferulic acid from eugenol in a recombinant strain of *E. coli* can offer a low cost and industrially economical process for vanillin production.

The present disclosure provides a method for producing vanillin through the bioconversion of eugenol to ferulic acid and then further conversion to vanillin. The bioconversion can be mediated in a cellular system such as bacteria *Escherichia coli* in same host cell or in different host cells (eg different *E. coli* host cells or in a different microbial species host cells such as an *E. coli* strain and an *Amycolatopsis* strain).

Accordingly, another embodiment of the present disclosures is a method of making vanillin comprising expressing VaoA gene in a cellular system, expressing MtSAD1 gene in the cellular system, growing the cellular system in medium, feeding eugenol to the cellular system, incubating the cellular system, and converting ferulic acid to vanillin. The method can further include expressing ADH gene in the cellular system. The expression of ADH enhances the biosynthetic pathway for making vanillin. The calA gene can be further expressed in the cellular system to enhance the method. Similarly, the calB gene can be further expressed in the cellular system for the same or similar purpose of enhancing the method. As for the bioconversion of ferulic acid to vanillin, this is facilitated by microorganisms, especially ones that express feruloyl-CoA synthetase (FCS), enoyl-CoA hydratase/aldolase (ECH) and optionally vanillin synthase. Examples of suitable microorganisms are *Pseudomonas* sp. HR 199, *Amycolatopsis* sp. ATCC 39116, *Amycolatopsis* sp. HR167, *Sphingomonas paucimobilis* SYK-6, *Pseudomonas fluorescens* AN103, *Streptomyces seotonii*, *Streptomyces sannanensis*, *Amycolatopsis* sp. strain (Zhp06) (see for example, CCTCC No. 2011265 from US2013/0115667A1).

In a separate embodiment, the method of making vanillin wherein expressing feruloyl-CoA synthetase (FCS) and enoyl-CoA hydratase/aldolase (ECH) further comprises expressing each step singularly or collectively in a cellular system or in an in vitro system. The cellular system can be any number of cellular systems that can facilitate the expression of vanillin. One embodiment uses a bacteria based cellular system, such as *E. coli*. Another embodiment utilizes an *Amycolatopsis/Streptomyces* based cellular system. Another embodiment utilizes a yeast based cellular system.

Feruloyl-CoA synthetase (FCS) is trans-feruloyl-CoA synthase (EC 6.2.1.34) is an enzyme that catalyzes the chemical reaction ferulic acid+CoASH+ATP⇌trans-feruloyl-CoA+products of ATP breakdown. The 3 substrates of this enzyme are ferulic acid, CoASH, and ATP, whereas its two products are trans-feruloyl-CoA and products of ATP breakdown. This enzyme belongs to the family of ligases, specifically those forming carbon-sulfur bonds as acid-thiol ligases. The systematic name of this enzyme class is trans-ferulate:CoASH ligase (ATP-hydrolysing). This enzyme is also called trans-feruloyl-CoA synthetase. (see Narbad A, Gasson M J (Pt 5). "Metabolism of ferulic acid via vanillin using a novel CoA-dependent pathway in a newly-isolated strain of *Pseudomonas fluorescens*". Microbiology. 144 (5): 1397-405. doi:10.1099/00221287-144-5-1397. PMID 9611814. and Pometto A L 3rd Crawford DL (1983). "Whole-cell bioconversion of vanillin to vanillic acid by *Streptomyces viridosporus*". Appl. Environ. Microbiol. 45 (5): 1582-5. PMC 242504. PMID 6870241. FCS is available at the German Collection of Microorganisms and Cell Cultures (DSMZ) with the reference DSMZ 7063. FCS nucleotide and amino acid sequences are provided herein as SEQ ID No. 7 and 8 respectively.

Enoyl-CoA Hydrataase (ECH)/Aldosase is an enoyl-CoA-hydratase/aldolase of *Pseudomonas* sp. DSMZ 7063, available from UniProt as Q9EY87. ECH nucleotide and amino acid sequences are provided herein as SEQ ID No. 9 and 10 respectively.

Vanillin synthase (EC 4.1.2.41) is an enzyme that catalyzes the chemical reaction 3-hydroxy-3-(4-hydroxy-3-methoxyphenyl)propanoyl-CoA⇌vanillin+acetyl-CoA-Hence, this enzyme has one substrate, 3-hydroxy-3-(4-hydroxy-3-methoxyphenyl)propanoyl-CoA, and two products, vanillin and acetyl-CoA. This enzyme belongs to the family of lyases, specifically the aldehyde-lyases, which cleave carbon-carbon bonds. The systematic name of this enzyme class is 3-hydroxy-3-(4-hydroxy-3-methoxyphenyl) propanoyl-CoA vanillin-lyase (acetyl-CoA-forming). Other names in common use include 3-hydroxy-3-(4-hydroxy-3-methoxyphenyl)propionyl-CoA:vanillin lyase, and (acetyl-CoA-forming).

It will be appreciated that the various genes and modules as discussed herein can be present in two or more recombinant host microorganisms rather than a single microorganism. When a plurality of recombinant microorganisms is used, they can be grown in a mixed culture to produce feulic acid and/or vanillin.

In some embodiments, the method of making vanillin is a one step process whereas in other embodiments the method of making vanillin is a two step process. This two step process can use the same microbial host cell or different microbial host cells.

The vanillin production described herein provides a vanillin product with a fully developed and well-balanced flavor profile comprising the major vanilla flavor compounds.

The main constituent of vanilla flavour is vanillin (3-methoxy-4-hydroxybenzaldehyde). It generally constitutes something less than 3% by weight of vanilla pods. It must be appreciated that the natural vanilla aroma and flavour originating in vanilla pods are due to a complex mixture of compounds, mostly phenolic, of which vanillin is merely the main one in terms of percentage composition. Major vanilla flavor compounds include, without limitation, phenolic compounds, furan compounds, fatty acid compounds, compounds formed by reaction with ethanol, and acetaldehyde diethyl acetal.

These phenolic vanilla flavor compounds include, without limitation, acetovanillone alpha-ethoxy-p-cresol, benzoic acid, guaiacol, 4-methylguaiacol, p-hydroxybenzaldehyde, methylparaben, methyl vanillate, 2-methoxy-4-vinylphenol 5-methoxyvanillin, phenol, Vanillin, vanillic acid, vanillyl alcohol, vanillyl ethyl ether, and p-vinylphenol. These phenolic vanilla flavor compounds, in particular guaiacol are desirably present in a low concentration so that they do not dominate, resulting in an unbalanced flavor.

Furan vanilla flavor compounds include, without limitation, 2-furfural, 2-furfural 5-(hydroxymethyl)-2-furfural, 5-methyl-2-furfural, 2-hydroxyfuraneol, gamma-butyrolactone (dihydro 2(3H)-furanone. Fatty acid vanilla flavor compounds include, without limitation, linoleic acid, and palmitic acid. If the vanilla flavor is extracted with a solvent such as ethanol, the vanilla flavor compounds that are formed by the reaction with ethanol include, without limitation, ethyl acetate, ethyl glycolyte, ethyl lactate, ethyl linoleate, ethyl pyrovate, ethyl levulinate, and diethylsuccinate. Someone seeking to produce a natural vanillin product which matches that of vanilla extract prepared from vanilla pods using the traditional curing method is not seeking to produce vanillin selectively, but to produce a mixture of compounds, mostly phenolic of which vanillin is merely the main one in terms of percentage composition. Overhage et al (2003 Appl and Env Microbiol 69(11) 6569-6576) also proposed vanillin production from eugenol using a two step process catalyzed by two recombinant E. coli strains. In the first step, E. coli strains XL1-Blue (pSKvaomPcalAmCalB) converted eugenol into FA with 93.3% molar yield (as discussed above) while in the second step, recombinant E. coli (pSKechE/Hfcs) converted ferulic acid to vanillin. This process led to the production of 4.6 g/l ferulic acid, 0.3 g/l vanillin and 0.1 g/l vanillyl alcohol from eugenol substrate indicating that the bioconversion of eugenol to vanillin using a recombinant E. coli host cell occurs at a low rate. It was reported in WO 2012/172108 that the vanillin yield from this 2 step process in E. coli was too low to be considered as an economically feasible process.

As Example 3 demonstrates, the present disclosure provide vanillin producing genes ech and fcs from which were cloned in E. coli to produce natural vanillin with limited success in LB culture but with much improved conversion rates in M9A culture medium. Without wishing to be bound by any theory, the use of a recombinant E. coli host microorganism instead of an Amycolatopsis strain to produce natural vanillin from ferulic acid may have advantages in terms of a better conversion rate.

In contrast, typically the highest concentrations of vanillin produced from ferulic acid were obtained using Streptomyces setonii ((see, for example, EP0885968B and Muheim and Lerch (1999) Appl Microbiol Biotechnol 51: 456-461) and Amycolatopsis sp. HR167 (EP0761817) where concentrations of about 8-16 g/l were reported when ferulic acid was fermented using these bacteria. It has been reported that for Amycolatopsis strain HR167, DSM9991 and DSM9992 11.5 g/l of vanillin was produced from 19.9 g of ferulic acid within 32 hour on a 10 liter scale.

In the method of production according to the present disclosure, the microorganism of the present disclosure is exposed to a selected starting material under conditions allowing to produce the selected product. Such conditions are described, for example, in EP0885968B or EP0761817B for the production of vanillin from ferulic acid.

By way of example, Haarman & Reimer GmbH have disclosed (EP0761817B and/or U.S. Pat. No. 6,133,003A) two strains of Amycolatopsis. Using one of them they achieved a culture medium containing up to 11.5 g/l of vanillin and 1 g/l of unreacted ferulic acid. These concentrations were determined by HPLC. There is no disclosure of any work-up technique or the isolation of the product. Givaudan SA disclosed in EP0885968B and/or U.S. Pat. No. 6,235,507B1 the use of Streptomyces setonii to produce vanillin and several by-products. The concentration of vanillin is disclosed in the range of 8-16 g/l.

The microorganism of the present disclosure, which can be used in the method of the present disclosure, belongs to the family of Actinomycetales, preferably to a suborder selected from the group consisting of Actinomycineae, Actinopolysporineae, Catenulisporineae, Corynebacterineae, Frankineae, Glycomycineae, Kineosporiineae, Micrococcineae, Micromonosporineae, Propionibacterineae, Pseudonocardineae, Streptomycineae and Streptosporangineae, wherein the suborders of Pseudonocardineae and Streptomycineae are preferred, and even more preferably belongs to the family of Pseudonocardiaceae or Streptomycetaceae, and even more preferably to genus Amycolatopsis or Streptomyces, and most preferably to genus Amycolatopsis.

Preferably the microorganism is selected from the group consisting of Pseudomonas sp. HR 199, Amycolatopsis sp. ATCC 39116, Amycolatopsis sp. HR167, Sphingomonas paucimobilis SYK-6, Pseudomonas fluorescens AN103, Streptomyces seotonii, Streptomyces sannanensis, Amycolatopsis sp. strain (Zhp06) and a combination thereof.

Among the genus Amycolatopsis, the strains Amycolatopsis sp. ATCC 39116, HR167 and DSMZ 9992, respectively, are particularly preferred in connection with the present disclosure. These strains (in particular ATCC39116) are reported to exhibit a very high vanillin tolerance and allow the achievement of good yields of vanillin by conversion of ferulic acid even prior to the inactivation or deletion of the vanillin dehydrogenase gene according to the present disclosure.

Preferably the biotransformation/bioconversion medium for the production of Natural Vanillin from Ferulic Acid is a culture medium, preferably containing Actinomycetes microorganisms such as *Streptomyces setonii* or *Amycolatopsis* organisms, most preferably of the strain deposited under accession number ATCC39116 (see EP0885968 and/or U.S. Pat. No. 6,235,507B1) or mutants thereof such as mutants available from CCTCC No: 2011265 (from US2013/0115667A1).

Preferably the microorganism produces a medium containing at least 3 g/l, preferably at least 4 g/l, 5 g/l, 6 g/l, 7 g/l, 8 g/l, 9 g/l, 10 g/l, 11 g/l, 12 g/l, 13 g/l, 14 g/l, 15 g/l, 16 g/l, 17 g/l, 18 g/l, 19 g/l, 20 g/l, 21 g/l, 22 g/l, 23 g/l, 24 g/l, 25 g/l, 26 g/l, 27 g/l, 28 g/l, 29 g/l, 30 g/of of vanillin.

The additional of additional gene or genes (eg for ech and/or fcs and/or CalA and/or CalB) coding for any of the above discussed enzymes (including vanillin synthase) improve the production of vanillin by providing additional metabolic means for converting the respective precursor to the corresponding product, thereby increasing the amount of enzymes to catalyze the respective reaction.

Particularly preferred microorganisms of the present disclosure are of genus *Amycolatopsis*, even more preferred of strain *Amycolatopsis* sp. ATCC 39116, wherein the gene for vanillin dehydrogenase is inactivated by an insertion of an antibiotic resistance gene into the gene coding for vanillin dehydrogenase. Another preferred option is the generation of a markerless vanillin dehydrogenase knockout mutant (see for example, WO2012/172108 and US2014/0087428A1).

Functional homologs of the polypeptides (eg at least encoded by one or more of the following genes VaoA, MtSAD1, AtADH, CalA, CalB, fcs, ech and the like) described herein are also suitable for use in producing ferulic acid and/or vanillin in a recombinant host. Thus, the recombinant host may include one or more heterologous nucleic acid(s) encoding functional homologs of the polypeptides described above and/or a heterologous nucleic acid encoding a mutant polypeptide as described herein.

A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide: polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of the encoded gene VaoA, MtSAD1, CalA, CalB polypeptides, FCS/ECH polypeptides and the like.

Sequence analysis can involve BLAST, Reciprocal BLAST, or PSI-BLAST analysis of nonredundant databases using a relevant amino acid sequence as the reference sequence. Amino acid sequence is, in some instances, deduced from the nucleotide sequence. Those polypeptides in the database that have greater than 40% sequence identity are candidates for further evaluation for suitability as ferulic acid/vanillin biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in polypeptides or vanillin biosynthesis polypeptides, e.g., conserved functional domains.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. Sequence identity can be determined as set forth above.

The expressed MtSAD1 is based on an amino acid SEQ ID No. 1 or a variant, homologue, mutant, derivative or fragment thereof.

The expressed MtSAD1 is based on an amino acid sequence with at least 70%, 75%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID No. 1.

In an alternative embodiment, the expressed MtSAD1 is based on amino acid with at least 95% identity to SEQ ID No. 1.

Alternatively, the expressed MtSAD1 is based on an amino acid sequence with at least 90% identity to SEQ ID No. 1.

In addition, the expressed MtSAD1 is based on amino acid sequence expressed from *E. coli*.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The terms "polypeptide" and "protein" are used interchangeably herein and mean any peptide-linked chain of amino acids, regardless of length or post-translational modification.

As used herein the term "derivative" includes but is not limited to a variant and a chemically modified derivative. The terms "derivative" and "variant" are used interchangeably herein.

As used herein, the term "variant" is to be understood as a polypeptide which differs in comparison to the polypeptide from which it is derived by one or more changes in the amino acid sequence. The polypeptide from which a variant is derived is also known as the parent or reference polypeptide. Typically a variant is constructed artificially, preferably by gene-technological means. Typically, the polypeptide from which the variant is derived is a wild-type protein or wild-type protein domain. However, the variants usable in the present disclosure may also be derived from homologs, orthologs, or paralogs of the parent polypeptide or from artificially constructed variants, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites.

In preferred embodiments, a variant usable in the present disclosure exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. In preferred embodiments, a variant usable in the present disclosure differs from the protein or domain from which it is derived by up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acid exchanges, preferably conservative amino acid changes. Variants may additionally or alternatively comprise deletions of amino acids, which may be N-terminal truncations, C-terminal truncations or internal deletions or any combination of these. Such variants comprising N-terminal truncations, C-terminal truncations and/or internal deletions are referred to as "deletion variants" or "fragments" in the context of the present application. The terms "deletion variant" and "fragment" are used interchangeably herein. A deletion variant may be naturally occurring (e.g. splice variants) or it may be constructed artificially, preferably by gene-technological means. Typically, the protein or protein domain from which the deletion variant is derived is a wild-type protein. However, the deletion variants of the present disclosure may also be derived from homologs, orthologs, or paralogs of the parent polypeptide or from artificially constructed variants, provided that the deletion variants exhibit at least one biological activity of the parent polypeptide. Preferably, a deletion variant (or fragment) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide.

A "variant" as used herein, can alternatively or additionally be characterised by a certain degree of sequence identity to the parent polypeptide from which it is derived. A variant of the present disclosure may have a sequence identity of at least 50%, 55%, 60%, 65%, 70%, 75%, 80%. 85%, 90%, 91%, 92%, 93%, 94%, 95%, 96%, 97%, 98%, 99% identity to the respective reference polypeptide or to the respective reference polynucleotide. The expression "at least 50%, 55%, 60%, 65%, 70%, 75%, 80%, 85%, 90%, 91%, 92%, 93%, 94%, 95% 96%, 97%, 98%, 99% sequence identity" is used throughout the specification with regard to polypeptide and polynucleotide sequence comparisons.

More precisely, a variant in the context of the present disclosure exhibits "at least 80% sequence identity" to its parent polypeptide. Preferably, the sequence identity is over a continuous stretch of 20, 30, 40, 45, 50, 60, 70, 80, 90, 100 or more amino acids. The expression "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids. Preferably, the polynucleotide in question and the reference polynucleotide exhibit the indicated sequence identity over a continuous stretch of 60, 90, 120, 135, 150, 180, 210, 240, 270, 300 or more nucleotides. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID No. 1, 2, 3, 4, 5, 6, 7, 8, 9 or 10, if not specifically indicated otherwise.

For example, a peptide sequence consisting of 30 amino acids compared to the amino acids of full length MtSAD1 with 269 amino acid residues may exhibit a maximum sequence identity percentage of 11.15% ($^{30}/_{269}$) while a sequence with a length of 150 amino acids may exhibit a maximum sequence identity percentage of 55.70% ($^{150}/_{269}$). The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, available on the world wide web at www.hmmer.wustl.edu/) or with the CLUSTAL algorithm (Thompson, J. D., Higgins, D. G. & Gibson, T. J. (1994) Nucleic Acids Res. 22, 4673-80) available e.g. on the world wide web at www.ebi.ac.uk/Tools/clustalw/or on the world wide web at www.ebi.ac.uk/Tools/clustalw2/index.html or on the world wide web at www.npsa-pbil.ibcp.fr/cgi-bin/npsa_automat.pl?page=/NPSA/npsa_clustalw.html.

Preferred parameters used are the default parameters as they are set on the world wide web at www.ebi.ac.uk/Tools/clustalw/or on the world wide web at www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST polynucleotide searches are performed with the BLASTN program, score=100, word length=12, to obtain polynucleotide sequences that are homologous to those nucleic acids which encode the relevant protein.

BLAST protein searches are performed with the BLASTP program, score=50, word length=3, to obtain amino acid sequences homologous to the SrKO polypeptide. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:
(1) hydrophobic: Met, Ala, Val, Leu, He;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and He; (ii) Ser and Thr; (ii) Asn and Gin; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

As used herein, the term "derivative" of a polypeptide also refers to a polypeptide that has been chemically modified so that it comprises other chemical groups than the 20 naturally occurring amino acids. Examples of such other chemical groups include without limitation glycosylated amino acids and phosphorylated amino acids. The polypeptide from which the derivative derives is also known as the parent polypeptide. This parent polypeptide can be a naturally occurring protein but can also be a protein variant as defined above. Chemical modifications of a polypeptide may provide advantageous properties as compared to the parent polypeptide, e.g. one or more of enhanced stability, increased biological half-life, or increased water solubility. Chemical modifications applicable to the derivatives usable in the present disclosure include without limitation: PEGylation, glycosylation of non-glycosylated parent polypeptides, or the modification of the glycosylation pattern present in the parent polypeptide.

A "biological activity" as used herein, refers to any activity a polypeptide may exhibit, including without limitation: enzymatic activity; binding activity to another compound: e.g. binding to another polypeptide, in particular binding to a receptor, or binding to a nucleic acid); inhibitory activity (e.g. enzyme inhibitory activity); activating activity (e.g. enzyme-activating activity); or toxic effects. It is not required that the variant or derivative exhibits such an activity to the same extent as the parent polypeptide. A variant is regarded as a variant within the context of the present application, if it exhibits the relevant activity to a degree of at least 10% of the activity of the parent polypeptide. Likewise, a derivative is regarded as a derivative within the context of the present application, if it exhibits the relevant biological activity to a degree of at least 10% of the activity of the parent polypeptide.

A polynucleotide belonging to a family of any of the enzymes disclosed herein or a protein can be identified based on its similarity to the relevant gene or protein, respectively. For example, the identification can be based on sequence identity. In certain preferred embodiments the disclosure features isolated nucleic acid molecules which are at least 50% (or 55%, 65%, 75%, 85%, 90%, 95%, or 98%) identical to (a) a nucleic acid molecule that encodes the polypeptide of SEQ ID NOs: 1, 3, 5, 8 or 10 (b) the nucleotide sequence of SEQ ID NOs, 2, 4, 6, 7 or 9 and (c) a nucleic acid molecule which includes a segment of at least 30 (e.g., at least 30, 40, 50, 60, 80, 100, 125, 150, 175, 200, 250, 300, 400, 500, 600, 700, 800, 850, 900, 950, 1000, or 1010) nucleotides of SEQ ID NOs: 2, 4, 6, 7 or 9.

The determination of percent identity between two nucleic acid sequences is accomplished using the mathematical algorithm of Karlin and Altschul, Proc. Natl. Acad. Sci. USA 90, 5873-5877, 1993. Such an algorithm is incorporated into the BLASTN and BLASTP programs of Altschul et al. (1990) J. Mol. Biol. 215, 403-410. BLAST nucleotide searches are performed with the BLASTN program, score=100, wordlength=12, to obtain nucleotide sequences homologous to HIN-1-encoding nucleic acids. BLAST protein searches are performed with the BLASTP program, score=50, wordlength=3, to obtain amino acid sequences homologous to the TAS2R polypeptide. To obtain gapped alignments for comparative purposes, Gapped BLAST is utilized as described in Altschul et al. (1997) Nucleic Acids Res. 25, 3389-3402. When utilizing BLAST and Gapped BLAST programs, the default parameters of the respective programs.

Hybridization can also be used as a measure of homology between two nucleic acid sequences. A nucleic acid sequence encoding any of the proteins disclosed herein, or a portion thereof, can be used as a hybridization probe according to standard hybridization techniques. The hybridization of a probe to DNA or RNA from a test source (e.g., a mammalian cell) is an indication of the presence of the relevant DNA or RNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2 times sodium chloride/sodium citrate (SSC) at 30.degree. C., followed by a wash in 1.times SSC, 0.1% SDS at 50.degree C. Highly stringent conditions are defined as equivalent to hybridization in 6.times sodium chloride/sodium citrate (SSC) at 45.degree C. followed by a wash in 0.2.times.SSC, 0.1% SDS at 65.degree. C.

The bioconversion of ferulic acid to vanillin according to the present disclosure produces vanillin as a predominant compound but also produces compounds other than vanillin which impart pleasant flavor notes to the bioconversion mixture and contribute in a positive manner to the sensory character of the mixture increasing its value as a flavorant for foods. Sensory analysis is carried out using, for example, the "triangle test" or other well established sensory tests utilized by trained Flavourists.

Vanilla is one of the most widely used flavouring agents in the world. It is the primary component of the extract of the vanilla bean which is extracted from the orchid *Vanilla planifolia, Vanilla tahitiensis* and *Vanilla pompona*. Though there are many compounds present in the extracts of vanilla, the compound vanillin (4-hydroxy-3-methoxybenzaldehyde) is primarily responsible for the characteristic flavor and smell of vanilla.

Vanillin is a phenolic aldehyde, which is an organic compound with the molecular formula $C_8H_8O_3$. Its functional groups include aldehyde, ether, and phenol. It is a white needle-like crystalline powder with an intensely sweet and very tenacious creamy vanilla-like odour. Vanilla is the second most expensive spice after saffron because growing the vanilla seed pods is labor-intensive. Despite the expense, vanilla is highly valued for its flavor. Moreover, the consumer led demand for natural vanillin highly exceeds the amount of vanillin extracted by plant sources.

As a result, vanilla is widely used in both commercial and domestic baking, perfume manufacture and aromatherapy. It is used as the principal flavouring ingredient with a variety of functional properties. Pure vanillin is widely used for enhancing flavours in the food and as a biopreservative because it is antimicrobial and antioxidant properties. It is an important raw material in the pharmaceutical industry.

Vanillin, instead of natural vanilla extract, is now more often used as a flavoring agent in foods, beverages, and pharmaceuticals. The largest use of vanillin is as a flavoring, usually in sweet foods. The ice cream and chocolate industries together comprise 75% of the market for vanillin as a flavoring, with smaller amounts being used in confections and baked goods. Vanillin is also used in the fragrance industry, in perfumes, and to mask unpleasant odors or tastes in medicines, livestock fodder, and cleaning products. It is also used in the flavor industry, as a very important key note for many different flavors, especially creamy profiles like cream soda. In addition, vanillin has been used as a chemical intermediate in the production of pharmaceuticals and other fine chemicals.

Synthetic essence, consisting basically of a solution of synthetic vanillin in ethanol, is derived from phenol and is of high purity. Synthetic vanillin is used to manufacture a number of household products, deodorants, air fresheners, floor polishes and herbicides. The "classical" synthesis of vanillin from eugenol or isoeugenol was developed in 1896 and it remained the preferred method for about 50 years. However, vanillin is now prepared industrially in large amounts by the Reimer-Tiemann reaction. This had led to the investigation of alternative methods for its production. As a result, various biotechnology based approaches have been investigated for the production of vanillin from lignin, eugenol, isoeugenol and ferulic acid by applying fungi, bacteria, plant cells or genetically engineered microorganisms. Biotechnology employs the tools of genetic engineering to develop methods of manufacturing important food ingredients. It broadens the range of possible substrates for the biosynthesis of food flavours, expands consumer choice in providing healthy, better tasting and safe food products. Products obtained through biotechnological processes from natural substrates are generally regarded as safe and considered as natural.

The ferulic acid/vanilla product or its precursor products may be commercially used as such (ie as an end product) or as an intermediate (eg to further produce derivatives or end-products using the intermediate as a precursor. Extracts of isolated, and optionally purified, vanillin find use in flavoring consumables such as food products, dietary supplements, nutraceuticals, pharmaceutical compositions, dental hygienic compositions, and cosmetic products.

Food products also include condiments such as herbs, spices and seasonings and flavor enhancers. A food product also includes prepared packaged products, such as dietetic sweeteners, liquid sweeteners, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. Food products also include diet or low-calorie food and beverages containing little or no sucrose. Other examples of food products envisioned in accordance with the present disclosure are described below and throughout the specification.

In another embodiment, the food products are fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectioneries such as candies, gums, fruit flavored drops, and chocolates, creams, icing, ice cream, pies and breads.

In another embodiment, the consumable is a pharmaceutical composition. Preferred compositions are pharmaceutical compositions containing vanillin and/or vanillin beta-D-glucoside and one or more pharmaceutically acceptable excipients. These pharmaceutical compositions can be used to formulate pharmaceutical drugs containing one or more active agents that exert a biological effect. As such, the pharmaceutical composition preferably further include one or more active agents that exert a biological effect. Such active agents include pharmaceutical and biological agents that have an activity. Such active agents are well known in the art.

In one embodiment of the present disclosure, the pharmaceutical composition is a nutritional composition. Examples of nutritional compositions having an undesirable taste include, but are not necessarily limited to, enteral nutrition products for treatment of nutritional deficit, trauma, surgery, Crohn's disease, renal disease, hypertension, obesity and the like, to promote athletic performance, muscle enhancement or general well being or inborn errors of metabolism such as phenylketonuria. In particular, such nutritional formulations can contain one or more amino acids which have a bitter or metallic taste or aftertaste In another embodiment, there is provided a method for the production of a food, a food precursor material or additive employed in the production of a foodstuff comprising the step of admixing vanillin obtainable by the methods of the present disclosure with a comestible product, the food, the food precursor material or the additive employed in the production of the foodstuff.

In a further embodiment, there is provided a method for the production of a nutraceutical or a pharmaceutical composition comprising the step of admixing vanillin obtainable by the methods of the present disclosure with an active agent and optionally with a pharmaceutically acceptable carrier and/or adjuvant.

In a further embodiment, there is provided the method of the previous paragraph further comprising the step of formulating the pharmaceutical composition into a pharmaceutically acceptable form.

The ingestible (or comestible) composition includes both "food or beverage products" and "non-edible products". By "food or beverage products", it is meant any edible product intended for consumption by humans or animals, including solids, semi-solids, or liquids (e.g., beverages).

The term "non-edible products includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as lip balms and other personal care products.

The ingestible (or comestible) composition also includes a pharmaceutical, medicinal or alternatively a formulation, e.g., a pharmaceutical or medicinal formulation or a food or beverage product or formulation. The compounds of the present disclosure can also be provided, individually or in combination, with any ingestible composition known or later discovered.

The Flavour, Fragrance and Ingredient Industry is aware of an increased demand from food manufacturers and final consumers for authenticity and traceability. Therefore more advanced analytical methods have been developed to discriminate the botanic origins of a vanilla product.

These analytical methods include but are not limited to the following methods and are discussed in detail in: "Herkunf und Authentizitaet von Vanillearomen" in Lebensmittelchemie (2010) 64: 17-48 and extracts are provided below as background information:

Natural vanilla flavour contains in addition to vanillin other characteristic associated substances such as, for example, p-hydroxybenzaldehyde, vanillic acid and p-hydroxybenzoic acid. The concentrations of these components in natural vanilla flavour are in characteristic ratios to one other and can under certain circumstances be utilised in authenticity testing. HPLC and GC methods have come to be used for quantitative determination of these substances.

Natural vanillin that has been obtained from the vanilla pod can be distinguished from vanillin produced synthetically or biotechnologically with the aid of the stable isotope ratios. The scientific principles that are based on fractionation of the stable isotopes are described in detail in the technical literature (see for example, Gassenmeier et al (2013) Flavour Fragr. J. 28; 25-29). In accordance with their photosynthetic pathway, plants and their component substances exhibit specific stable isotope ratios of the elements carbon ($^{13}C/^{12}C$) and hydrogen ($^{2}H/^{1}H$). Thus three photosynthetic pathways are known in plants for $CO_2$ fixation. The so-called $C_3$ plants (e.g., wheat, rice, sugar beet) make use of the ribulose biphosphate carboxylate reaction, while $C_4$ plants (e.g., cane sugar, maize) use the phosphoenolpyruvate carboxylase reaction. CAM plants such as succulents and orchids (e.g., *Vanilla planifolia*) have the crassulacean acid metabolism.

By way of background information, ferulic acid, a naturally occurring phenolic compound, is the most abundant hydroxycinnamic acid found in the cell walls of C3, C4 or CAM plants where it is ester-linked to polysaccharides. Phytosynthesis, the process by which plants take energy from the sun and store it within the bonds of sugar is a simple process that needs only light, water and carbon dioxide to take place. Plants can be divided into three different types depending on their photosynthetic pathway: C3, C4 and CAM plants. C3 plants include rice and wheat. C4 plants include maize and several types of grasses. CAM is an intermediate mechanism between C3 and C4 in which the plant uses the C3 or C4 pathway. The three photosynthetic processes from C3, C4 or CAM plants will generate isotope effects, in particular 13C isotope effect which helps traceability of the botanic origin as discussed below:

Gas chromatography-IRMS (GC-IRMS) and elemental analyser-IRMS (EA-IRMS): with the direct coupling of an elemental analyser (EA) or a gas chromatograph (GC) with an isotope-ratio mass spectrometer (IRMS) it is possible to determine the stable isotopes of carbon, oxygen and hydrogen with great precision.

The use of GC-IRMS enables a component-specific analysis to be made on the isotope ratios of vanillin and with sufficient concentration also that of the associated substances in a solvent extract. Determination of the carbon isotope ratio is carried out with GC-combustion-IRMS (GC-C-IRMS) and the oxygen and hydrogen isotope ratios with GC-pyrolysis-IRMS (GC-P-IRMS).

In vanillin isolated by preparative synthesis the $^{18}O/^{16}O$ and $^{2}H/^{1}H$ isotope ratios are determined with a high temperature conversion elemental analyser (TC/EA) and the 13C/12C isotope ratios determined with a combustion elemental analyser (C/EA).

In all the processes the concentrations of the $^{13}C$ and $^{12}C$ isotopes are set as a ratio and related to the internationally established standard Vienna Pee Dee Belemnite (VPDB). The delta-value ($\delta^{13}C$ value) of the carbon isotope ratio ($^{13}C/^{12}C$) in per mil (‰) VPDB is reported according to the formula $$\delta^{13}C[\permil]=(((^{13}C_{sample}/^{12}C_{sample})/(^{13}C_{standard}/^{12}C_{standard}))-1)\times 1000.$$

The isotope ratio of hydrogen ($^{2}H/^{1}H$) and of oxygen ($^{18}O/^{16}O$) is calculated accordingly as a $\delta^{2}H$ or $\delta^{18}O$ value and reported as ‰ VSMOW (Vienna Standard Mean Ocean Water).

The $\delta^{13}C$ values of isolated vanillin determined so far as part of numerous proficiency tests of different laboratories by EA-IRMS and GC-IRMS have exhibited very good comparability; so these methods are to be considered as validated.

As used herein, the term "$\delta^{13}C$" refers to the carbon isotope ratio ($^{13}C/^{12}C$) in per mil (‰) VPDB is reported according to the formula:

$$\delta^{13}C[\permil]=(((^{13}C_{sample}/^{12}C_{sample})/(^{13}C_{standard}/^{12}C_{standard}))-1)\times 1000.$$

Table 1 below provides an overview of the stable isotope ratios published in the technical literature for carbon and hydrogen in vanillin of different geographical and botanical origin and of vanillin produced from different raw materials.

It can be seen from Table 1 below that $\delta^{13}C$ values may be used to differentiate vanillin from various botanical origins as well as different production processes:

natural vanilla from *Vanilla planifolia* or *Vanilla tahitensis* or from aqueous ethanolic extracts of these varieties produces $\delta^{13}C$ values that are more positive than −21.5‰ VPDB;

for vanillin that is produced biotechnologically—e.g., from ferulic acid (ex rice)—and may be called natural vanilla according to food law the $\delta^{13}C$ values are typically in the region of −36‰ to −37‰ VPDB;

vanillin that is chemically synthesised from lignin, eugenol or guaiacol and is classed as "nature-identical"

according to the AromenV (Flavour Regulation) still in force has $\delta^{13}C$ values that are more negative than −25‰ VPDB.

According to the disclosure in another report (see Cochennec C Perfumer & Flavourist (2013) 38: 20-27), the $\delta^{13}C$ isotope deviation of plants varies depending on the photosynthetic mechanism.

It is disclosed in Cochennec (2013) that plants with a $C_4$ photosynthetic mechanism, such as maize, displays $\delta^{13}C$ value isotopic deviation for ferulic acid from $C_4$ plants such as maize ranging from −19% to −16‰ and thus will display a mean isotope deviation of about −$\delta^{13}C$ value of about 14‰.

In contrast, it is also disclosed in Cochennec (2013) that vanillin from ferulic acid from C3 plants such as rice and wheat display a $\delta^{13}C$ value isotope deviation ranging from −38% to −35‰ which clearly differentiates it from the vanillin from ferulic acid of a $C_4$ plant or vanillin from beans (CAM plants).

Thus, $\delta^{13}C$ value for $C_4$ plants would generally be "less negative" or "greater" in value compared with the $\delta^{13}C$ for $C_3$ plants.

The $\delta^{13}C$ value for vanillin from vanilla beans (about −21.5‰ VPDB) as disclosed in Table 1 below is between that for $C_3$ and $C_4$ plants.

In Summary: According to one study (see Cochennec C Perfumer & Flavourist (2013) 38: 20-27), ferulic acid from $C_4$ plants (eg maize) have a $\delta^{13}C$ value in the range of −16 to −19‰ and vanillin from $C_3$ plants (eg rice) have a $\delta^{13}C$ value of −35 to −38‰.

According to another study (see Table 1 below) $\delta^{13}C$ values for vanillin from C3 plants (eg rice) typically in the region of −36‰ to −37‰ VPDB;

As disclosed herein in Example 5, the Applicants have demonstrated that Natural Ferulic acid/Natural Vanillin acid obtainable from Eugenol by the methods of the present disclosure has a $\delta^{13}C$ value in the range of from about −25 to about −32‰.

Preferably the Natural Ferulic acid/Natural Vanillin acid obtainable from Eugenol by the methods of the present disclosure has a $\delta^{13}C$ value of about −25‰.

Preferably the Natural Ferulic acid/Natural Vanillin acid obtainable from Eugenol by the methods of the present disclosure has a $\delta^{13}C$ value of about −26‰.

Preferably the Natural Ferulic acid/Natural Vanillin acid obtainable from Eugenol by the methods of the present disclosure has a $\delta^{13}C$ value of about −27‰.

Preferably the Natural Ferulic acid/Natural Vanillin acid obtainable from Eugenol by the methods of the present disclosure has a $\delta^{13}C$ value of about −28‰.

Preferably the Natural Ferulic acid/Natural Vanillin acid obtainable from Eugenol by the methods of the present disclosure has a $\delta^{13}C$ value of about −29‰.

Preferably the Natural Ferulic acid/Natural Vanillin acid obtainable from Eugenol by the methods of the present disclosure has a $\delta^{13}C$ value of about −30‰.

Preferably the Natural Ferulic acid/Natural Vanillin acid obtainable from Eugenol by the methods of the present disclosure has a $\delta^{13}C$ value of about −31‰.

Preferably the Natural Ferulic acid/Natural Vanillin acid obtainable from Eugenol by the methods of the present disclosure has a $\delta^{13}C$ value of about −32‰.

Natural Ferulic Acid (FA)/Natural Vanillin (NV) (Ex Eugenol) is Different from FA/NV from Other Natural Plant Sources:

Thus, in view of the above data, not only do $C_3$, $C_4$ and CAM plants have different $\delta^{13}C$ signatures allowing $C_3$, $C_4$ grasses and CAM plants to be detected and differentiated by their $\delta^{13}C$ values, natural ferulic acid and natural vanillin obtainable from eugenol using the methods of the present disclosure have $\delta^{13}C$ values which are different from the $\delta^{13}C$ value obtained from at least C3, C4 plants (ie from a natural plant group source selected from rice, maize, sugar beet, wheat and curcumin) and from the $\delta^{13}C$ value for CAM plants (eg the $\delta^{13}C$ value for vanilla extract from the traditional curing of the vanillin bean and/or from using an accelerated biologic process (see for example, WO2010/066060 and WO 2010/066061 the entire contents of which are incorporated herein by reference).

TABLE 1

Stable Isotope Ratios of Carbon and Hydrogen in Vanillin of Different Origins and Production (obtained as a translation from "Herkunf und Authentizitaet von Vanillearomen" in Lebensmittelchemie (2010) 64: 17-48) - all references to the Literature in Table 1 are references to the literature cited in the above cited 2010 publication. Processes as Determined in Different Scientific Studies

| Origin/Vanillin raw material | $\delta^{13}C_{VPDB}$ [‰] | $\delta^2H_{VSMOW}$ [‰] | Literature |
|---|---|---|---|
| ex pod (Bourbon) | −21.5 to −19.2 | | [26] |
| ex pod (Tahiti) | −19.7 to −15.9 | | [26] |
| ex pod | >−21 | | [27] |
| ex pod | −21.5 to −16.8 | −115 to −52 | [24] |
| ex pod | −22.0 to −19.0 | | [21] |
| ex guaiacol | −36.2 to −24.9 | −23 to −17 | [24] |
| ex eugenol | −31.7 to −29.9 | | [24] |
| ex lignin | −28.7 to −26.5 | −204 to −170 | [24] |
| ex ferulic acid from rice bran | −37 to −36 | | [17] |

It is stated in the above cited 2010 publication (which provides Table 1 above) that: the $^2H/^1H$ (D/H) ratios at the different positions of the vanillin molecule can be determined by means of positional $^2H$-NMR measurement. The method also known as SNIF-NMR® is based on the fact that the distribution of the $^2H$ isotope at the different positions of a molecule does not occur statistically but is dependent on discrimination effects during the (bio) synthesis of the raw material. Even the blending of natural and synthetic vanillin can be detected over the four (D/H) isotope ratios of the vanillin molecule that are relevant to evaluation. The method was tested in an AOAC (Association of Official Analytical Chemists) round robin experiment and is used in particular for authenticity monitoring in the aroma industry. As up to now relatively large quantities of substances with the highest possible purity are required, this method is not applicable in the practice of official monitoring and quality control of foods or only to a very limited extent. The first results on a determination of the positional $^{13}C$ distribution in the vanillin molecule using NMR promise advantages over $^2H$-NMR, since $^{13}C$-NMR is considerably more sensitive. Thus in this case there is a particularly significant possibility of differentiating chemically synthesised vanillin from biosynthetic vanillin. This method can probably also only be used in a few special laboratories within the foreseeable future.

Another study (Cochennec 2010) teaches that: Isotope deviation analysis such as $^{13}C$ IRMS and $^2H$-SNIF-NMR (site specific natural isotopic fractionation-nuclear magnetic resonance) are methods for the assessment of the authenticity of vanilla and are commonly used to unequivocally discriminate vanilla from vanilla bean from all other known sources of vanillin or mixtures thereof. It has been reported that 13CIRMS and 2H—SNIF-NMR isotopic deviation methods have perfectly discriminated vanillin obtained by bioconversion of ferulic acid from rice bran from vanillin coming from the vanilla bean, thus guaranteeing genuineness of the source ((see *Cochennec C Perfumer & Flavourist* (2013) 38: 20-27).

As used herein, the terms positional $^2$H-NMR measurement, D-NMR and SNIF-NMR® are used interchangeably and any reference to "D-NMR" is a reference to $^2$H-NMR measurement and/or SNIF-NMR®".

For each new source of vanillin previously unknown in the isotope database, such as natural vanillin from ferulic acid from eugenol, a determination of botanic origin may be carried out using an isotope determination in combination with D-NMR. In this regard, as evidenced by the discussion below, D-NMR was used successfully by the Applicants to differentiate between naturally derived ferulic acid/vanillin obtainable from eugenol using the methods of the present invention and artificially derived and/or synthetic ferulic acid/vanillin obtained from lignin and/or guaiacol.

Natural Ferulic Acid (FA)/Natural Vanillin (NV) (Ex Eugenol) is Different from FA/NV from Other Artificially Derived/Chemically Synthesised FA/NV Sources:

As Table 1 above and Table 6 (Example 5) demonstrate artificially/synthetically derived lignin has a $\delta^{13}$C value in the range of from about -27 to -29‰ which is a sub-range within the $\delta^{13}$C value range for ferulic acid/vanillin obtainable from Eugenol by the methods of the present disclosure. In addition, artificially/synthetically derived guaiacol has a $\delta^{13}$C value in the range of from about -25 to -36‰ which is an overlapping range with the $\delta^{13}$C value range for ferulic acid/vanillin of about -25 to -32‰ obtainable from Eugenol by the methods of the present disclosure.

However, as Example 6 demonstrates when a secondary test measuring the enrichment of deuterium on the phenyl ring of vanillin from various sources was also measured using D-NMR, the ferulic acid/vanillin samples obtained from eugenol by the methods of the present disclosure cluster at a location different from the lignin and/or guaiacol sample and thus the use of D-NMR as a secondary test in combination with a $\delta^{13}$C value measurement also facilitates the botanic origin of the natural ferulic acid/vanillin to be identified.

Other aspects of the disclosure include the following numbered paragraphs:
1. A recombinant *E. coli* strain comprising one or more VaoA, MtSAD1 and AtADH genes or a variant, homologue, mutant, derivative or fragment thereof which converts eugenol to ferulic acid.
2. A process for preparing ferulic acid comprising subjecting eugenol to the recombinant *E. coli* microorganism comprising one or more VaoA, MtSAD1 and AtADH genes or a variant, homologue, mutant, derivative or fragment thereof or an isolated enzyme thereof which bioconverts eugenol to ferulic acid for a period of time sufficient to bioconvert said eugenol to ferulic acid and recovering the ferulic thus formed.
3. The process according to paragraph 2, wherein said ferulic acid is natural ferulic acid.
4. A process according to paragraph 2 or 3 comprising using further converting the ferulic acid to vanillin.
5. The process according to paragraph 4, wherein the vanillin is produced from natural ferulic acid.
6. The process according to any one of paragraphs 4-5, wherein a first recombinant *E. coli* microorganism bioconverts eugenol to ferulic acid and a second recombinant *E. coli* strain bioconverts ferulic acid to vanillin.
7. The process according to paragraph 6, wherein the first recombinant *E. coli* strain is the *E. coli* microorganism comprises one or more VaoA, MtSAD1 and AtADH genes or a variant, homologue, mutant, derivative or fragment thereof.
8. The process according to paragraph 6 or 7, wherein the second recombinant *E. coli* microorganism comprises one or more ech and fcs genes or a variant, homologue, mutant, derivative or fragment thereof.
9. A process for preparing ferulic acid comprising subjecting eugenol to a recombinant *E. coli* microorganism comprising one or more VaoA, MtSAD1 and AtADH genes or a variant, homologue, mutant, derivative or fragment thereof or isolated enzyme thereof which converts eugenol to ferulic acid for a period of time sufficient to convert said eugenol to ferulic acid and recovering the ferulic acid thus formed, wherein if the recombinant *E. coli* microorganism bioconverts eugenol to ferulic acid then the recombinant *E. coli* microorganism is contained in a medium which comprises a carbon source.
10. The process according to paragraph 9, wherein the medium is an M9A medium.
11. The process according to paragraph 9 or 10, wherein the ferulic acid has a $\delta^{13}$C value of from about minus 25‰ to about minus 32‰.
12. The process according to any one of paragraphs 9-11 comprising further converting the ferulic acid to vanillin.
13. A process for preparing ferulic acid comprising subjecting eugenol to a recombinant *E. coli* microorganism comprising one or more VaoA, MtSAD1 and AtADH genes or a variant, homologue, mutant, derivative or fragment thereof or an isolated enzyme thereof which bioconverts eugenol to ferulic acid, to bioconvert said eugenol to ferulic acid in a concentration of at least 5-6 g/l over period of time of from about 4 to about 25 hours, a concentration of about 15-16 g/l over a period of time of from about 4 to about 40 hours and about 25-27 g/l over a period of time of from about 4 to about 70 hours and recovering the ferulic acid thus formed.
14. A process according to paragraph 13 wherein the vanillin has a $\delta^{13}$C value of from about minus 25‰ to about minus 32‰.
15. The process according to paragraph 11 or paragraph 14 wherein the authenticity of the natural ferulic acid and/or natural vanillin is determined using a $\delta^{13}$C value and/or a D-NMR value measurement.
16. A bioconversion method of making vanillin including expressing VaoA gene in a mixture, expressing MtSAD1 gene in the mixture, feeding eugenol to the mixture, and converting ferulic acid to vanillin by incubating with a microbial *Amycolatopsis* sp. microorganism (Zhp06) and/or a recombinant *E. coli* microorganism.
17. Use of a $\delta^{13}$C value and/or a D-NMR value measurement to authenticate a ferulic acid/vanillin sample obtainable from eugenol according to any one of paragraphs 1-16.
18. The use according to paragraph 17 wherein a $\delta^{13}$C value in the range of minus 25‰ to about minus 32‰ is indicative of a natural ferulic acid and/or natural vanillin obtainable from eugenol.
19. The use according to paragraph 18 wherein the authenticity of the natural ferulic acid and/or natural vanillin obtainable from eugenol is confirmed using a D-NMR test.

Additional sequences that can be used in any of the methods described herein are shown as follows:

PRT Medicago truncatula (amino sequence of MtSAD1 or a variant thereof).

SEQ ID NO. 17

Met ala Glu Ala Ser Ser Thr Asn Ser Gly Leu Arg Leu Ala Gly Lys

Val Ala Ile Val Thr Gly Gly Ala Ser Gly Ile Gly Lys Glu Thr Ala

His Leu Phe Ala Glu Gln Gly Ala Arg Met Val Val Ile Ala Asp Ile

Gln Asp Glu Leu Gly Asn Gln Val Ala Ala Ser Ile Gly Ser Arg Lys

Cys Thr Tyr Ile His Cys Asp Ile Ala Asn Glu Asp Gln Val Lys Asn

Leu Val Gln Ser Thr Val Asn Ala Tyr Gly Gln Ile Asp Ile Met Phe

Ser Asn Ala Gly Ile Ala Ser Pro Ser Asp Gln Thr Ile Leu Glu Leu

Asp Ile Ser Gln Ala Asp His Val Phe Ala Val Asn Ile Arg Gly Thr

Thr Leu Cys Val Lys Tyr Ala Ala Arg Ala Met Val Glu Gly Arg Val

Arg Gly Ser Ile Val Cys Thr Ala Ser Val Leu Gly Ser Gln Gly Val

Leu Arg Leu Thr Asp Tyr Thr Ile Ser Lys His Ala Ile Ile Gly Leu

Met Arg Ser Ala Ser Val Gln Leu Ala Lys Tyr Gly Ile Arg Val Asn

Cys Val Ser Pro Asn Gly Leu Ala Thr Pro Leu Thr Met Lys Leu Leu

Gly Ala Ser Ala Lys Thr Val Glu Leu Ile Tyr Glu Gln Asn Lys Arg

Leu Glu Gly Val Val Leu Asn Thr Lys His Val Ala Asp Ala Val Leu

Phe Leu Val Ser Asn Glu Ser Asp Phe Val Thr Gly Leu Asp Leu Arg

Val Asp Gly Ser Tyr Val Tyr Gly Lys Tyr Glu Leu Leu

DNA Medicago truncatula (DNA sequence of MtSAD1 or a variant thereof).

SEQ ID NO. 18 atggcagaag catcatccac taacagcggt cttaggttag ccggcaaagt agccatcgtc accggaggtg ccagcggcat tggcaaagag acggcacatc tctttgccga acaaggtgca cgcatggtgg tgattgccga catccaagac gagttgggca atcaagtggc tgcatccatt ggcagtcgca agtgcaccta cattcattgt gatatagcaa atgaagatca agttaaaaat ctcgttcaat caactgtcaa tgcttatgga cagatagata ttatgtttag caatgctggg attgcaagtc catctgatca gactattttg gaactcgaca tttctcaagc cgaccatgtg tttgcagtta acattcgagg aacgacattg tgtgtgaaat acgcggcacg tgcgatggtg gaggggcgcg tgaggggtag cattgtgtgc acagcgagcg tattgggtag ccaaggtgtc ttgaggttaa ccgattacac aatatcgaag catgcaataa tagggttgat gcgctcagcg agtgtgcaac ttgcaaaata cgggataaga gtgaattgtg tctcgccaaa tggattagca acaccattga ctatgaaatt gttaggggca agtgctaaga cagtcgagtt gatttatgaa caaaacaaga ggttggaagg agtggttctc aacactaaac atgttgcaga tgctgtgttg ttcttggtat ctaatgaatc tgactttgtc actggccttg atcttcgtgt ggatggcagc tatgtttatg gcaaatatga actattataa PRT Arabidopsis thaliana (Protein sequence of AtADH or a variant thereof).

SEQ ID NO. 19

Met Glu Asn Gly Lys Cys Asn Gly Ala Thr Thr Val Lys Leu Pro Glu

Ile Lys Phe Thr Lys Leu Phe Ile Asn Gly Gln Phe Ile Asp Ala Ala

Ser Gly Lys Thr Phe Glu Thr Ile Asp Pro Arg Asn Gly Glu Val Ile

Ala Thr Ile Ala Glu Gly Asp Lys Glu Asp Val Asp Leu Ala Val Asn

Ala Ala Arg Tyr Ala Phe Asp His Gly Pro Trp Pro Arg Met Thr Gly

Phe Glu Arg Ala Lys Leu Ile Asn Lys Phe Ala Asp Leu Ile Glu Glu

-continued

Asn Ile Glu Glu Leu Ala Lys Leu Asp Ala Val Asp Gly Gly Lys Leu

Phe Gln Leu Gly Lys Tyr Ala Asp Ile Pro Ala Thr Ala Gly His Phe

Arg Tyr Asn Ala Gly Ala Ala Asp Lys Ile His Gly Glu Thr Leu Lys

Met Thr Arg Gln Ser Leu Phe Gly Tyr Thr Leu Lys Glu Pro Ile Gly

Val Val Gly Asn Ile Ile Pro Trp Asn Phe Pro Ser Ile Met Phe Ala

Thr Lys Val Ala Pro Ala Met ala Ala Gly Cys Thr Met Val Val Lys

Pro Ala Glu Gln Thr Ser Leu Ser Ala Leu Phe Tyr Ala His Leu Ser

Lys Glu Ala Gly Ile Pro Asp Gly Val Leu Asn Ile Val Thr Gly Phe

Gly Ser Thr Ala Gly Ala Ala Ile Ala Ser His Met Asp Val Asp Lys

Val Ser Phe Thr Gly Ser Thr Asp Val Gly Arg Lys Ile Met Gln Ala

Ala Ala Ala Ser Asn Leu Lys Lys Val Ser Leu Glu Leu Gly Gly Lys

Ser Pro Leu Leu Ile Phe Asn Asp Ala Asp Ile Asp Lys Ala Ala Asp

Leu Ala Leu Leu Gly Cys Phe Tyr Asn Lys Gly Glu Ile Cys Val Ala

Ser Ser Arg Val Phe Val Gln Glu Gly Ile Tyr Asp Lys Val Val Glu

Lys Leu Val Glu Lys Ala Lys Asp Trp Thr Val Gly Asp Pro Phe Asp

Ser Thr Ala Arg Gln Gly Pro Gln Val Asp Lys Arg Gln Phe Glu Lys

Ile Leu Ser Tyr Ile Glu His Gly Lys Asn Glu Gly Ala Thr Leu Leu

Thr Gly Gly Lys Ala Ile Gly Asp Lys Gly Tyr Phe Ile Gln Pro Thr

Ile Phe Ala Asp Val Thr Glu Asp Met Lys Ile Tyr Gln Asp Glu Ile

Phe Gly Pro Val Met Ser Leu Met Lys Phe Lys Thr Val Glu Glu Gly

Ile Lys Cys Ala Asn Asn Thr Lys Tyr Gly Leu Ala Ala Gly Ile Leu

Ser Gln Asp Ile Asp Leu Ile Asn Thr Val Ser Arg Ser Ile Lys Ala

Gly Ile Ile Trp Val Asn Cys Tyr Phe Gly Phe Asp Leu Asp Cys Pro

Tyr Gly Gly Tyr Lys Met Ser Gly Asn Cys Arg Glu Ser Gly Met Asp

Ala Leu Asp Asn Tyr Leu Gln Thr Lys Ser Val Val Met Pro Leu His

Asn Ser Pro Trp Met

DNA Arabidopsis thaliana (DNA sequence of AtADH or a variant thereof).
SEQ ID NO. 20
atggagaacg gcaaatgcaa cggagccacg acggtgaagt taccggagat caaattcacc aagcttttca tcaacggcca gttcattgat gctgcttcag ggaagacgtt tgagacgata gaccctagga acggtgaagt gatcgcaaca atagccgaag gagacaaaga agacgttgac ttggccgtta acgctgcacg ttacgccttc gaccatggtc cttggcctcg catgaccggc ttcgagaggg caaagcttat caacaaattc gcagacttaa tagaggaaaa cattgaggaa ttggctaaac ttgatgcggt tgacggtgga aaattgtttc agttgggaaa atatgctgat attccggcca cagccggtca ttttcgatac aatgcgggtg cagcagataa aatccacggc gagactctta aaatgacgcg tcaatctttg ttcggataca ccctcaaaga accaattgga gtggttggta atatcatccc ttggaatttc ccaagcatta tgtttgccac aaaggtggct ccggctatgg ctgctggttg caccatggtg gtcaagccag ctgaacagac ttcactctct gctttgttct atgcccatct ctcaaaagaa gcgggaattc ctgatggtgt gctcaacatt gtaactggtt ttggatcaac tgctggagct gccattgcct cccatatgga cgtagacaaa gttagtttca ctgggtcaac agatgttgga aggaagataa tgcaagccgc agccgcaagt aatctcaaaa aagtttccct tgaattaggc gggaaatcgc cacttctcat attcaacgac -continued

```
gctgatattg acaaagccgc cgatcttgcg cttctcggtt gcttttacaa caagggtgaa atgtaa.

DNA Penicillium simplicissimum (DNA sequence of VaoA or a vari-
ant thereof).
                                                       SEQ ID NO. 21
atgagtaaaa cccaagaatt tcgtccgctg accttacctc cgaaattaag cctgtcagat tttaacgaat ttatacaaga catcataagg atagtgggta gcgagaacgt agaggttatc agtagcaaag atcaaatcgt ggatggcagc tacatgaagc cgacccatac ccatgacccg caccacgtta tggatcaaga ttattttctg gcaagcgcta tcgtcgcacc gcgtaacgtt gcagacgttc aaagcattgt tggtctggca aacaaattca gcttcccgct gtggccgatt agcatcggtc gtaacagcgg ttacggtgga gcagcaccgc gtgttagcgg tagcgttgtt ctcgatatgg gcaaaaacat gaatcgtgtt ctggaagtta atgtggaagg tgcctattgt gttgttgaac cgggtgttac ctatcatgat ctgcataatt atctggaagc caataacctg cgtgataagc tgtggctgga cgttccagac ctgggtggtg gcagcgtact gggtaacgca gtagaacgtg gagttggtta caccccgtat ggtgaccact ggatgatgca tagcggtatg gaggttgtgc tggcaaacgg tgagctgctg cgtaccggta tgggtgcact gccagacccg aagcgaccgg agacaatggg tctgaagccg gaggatcaac cgtggtcaaa gattgcacac ctgtttccgt atggttttgg tccgtatatt gatggtctgt ttagtcagag caacatgggt attgttacca aaattggcat ttggctgatg ccgaatccgg gtggttatca gagctatctg attaccctgc cgaaagatgg tgatctgaaa caggcagttg atattatccg tccgctgcgt ctgggtatgg cactgcagaa tgttccgacc attcgtcata ttctgctgga tgccgcagtt ctgggtgata aacgtagcta tagcagtaaa accgaaccgc tgagtgatga agaactggat aaaattgcaa aacagctgaa tctgggtcgc tggaacttt atggtgcact gtatggtccg gaaccgattc gtcgtgtgct gtgggaaacc attaaagatg catttagcgc aattccgggt gtgaaattct attttccgga agatacaccg gaaaattcag ttctgcgtgt tcgtgataaa accatgcagg gtattccgac ctatgatgaa ctgaaatgga ttgattggct gccgaatggt gcccacctct tttttagccc gatagcaaaa gttagcggag aggacgcgat gatgcagtat gcagtgacca aaaacgttg tcaagaagca ggtctggatt ttattggcac ctttaccgtt ggtatgcgtg aaatgcatca tattgtgtgc atcgtgttta acaaaaaga cctgattcag aaacgcaagg ttcaatggct tatgcgtaca ctgatagacg attgcgcagc taacggttgg ggtgagtacc gtacacacct agcatttatg gatcagatca tggagacgta taattggaat aacagcagct ttctgcgctt taatgaagtt ctgaaaaatg ccgttgatcc gaatggtatt atcgcaccgg gtaaaagcgg cgtatggcct agccagtata gccacgtaac ctggaagcta taa
```

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The term "comprising" also means "including" as well as "consisting" e.g. a composition "comprising" X may consist exclusively of X or may include something additional e.g. X+Y. It must be noted also that, as used in this specification and the appended claims, the singular forms "a", "an" and "the" include plural referents unless the content clearly dictates otherwise. By way of example, a reference to "a gene" or "an enzyme" is a reference to "one or more genes" or "one or more enzymes".

It is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art. In accordance with the present disclosure there may be conventional molecular biology, microbiology, and recombinant DNA techniques employed which are within the skill of the art.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety.

The examples described herein are illustrative of the present disclosure and are not intended to be limitations thereon. Different embodiments of the present disclosure have been described according to the present disclosure. Many modifications and variations may be made to the techniques described and illustrated herein without departing from the spirit and scope of the disclosure. Accordingly, it should be understood that the examples are illustrative only and are not limiting upon the scope of the disclosure.

DETAILED DESCRIPTION OF THE DRAWINGS IN MORE DETAIL

Figure 4:
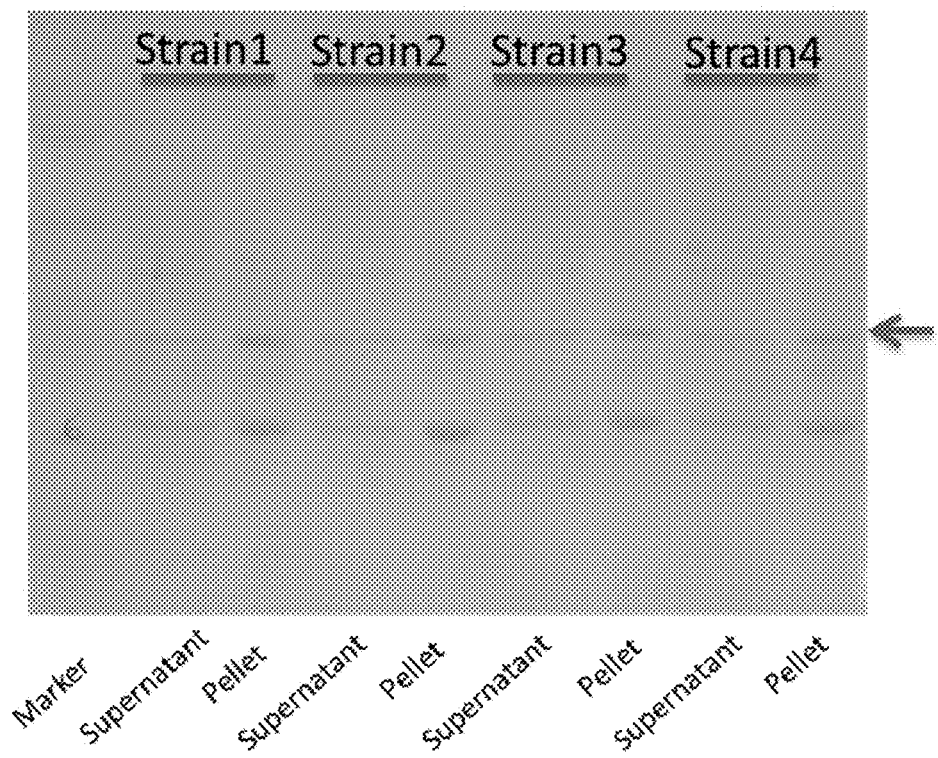
FIG. 4 is a gel picture showing the protein expression of MtSAD1 in E. coli. Arrow indicates the MtSAD1 protein.
Figure 5A:
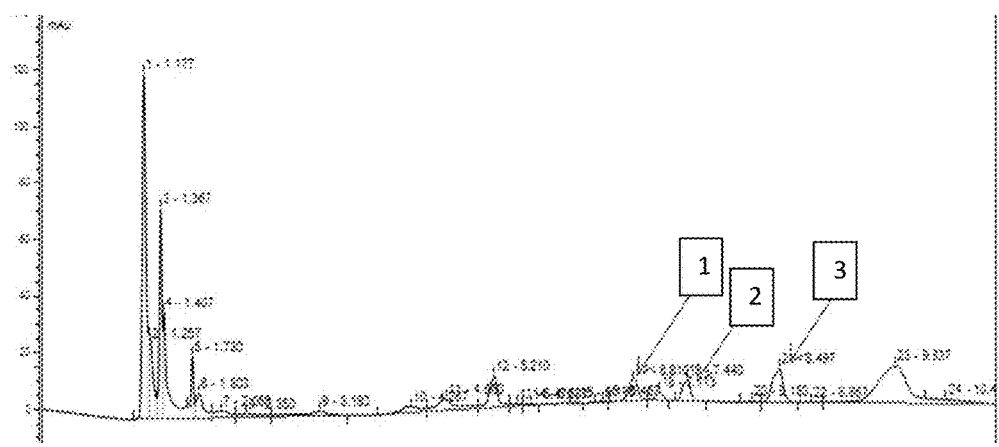
FIGS. 5A-5B are chromatograms showing the bioconversion of coniferyl alcohol by the gene product of MtSAD1.
Figure 5B:
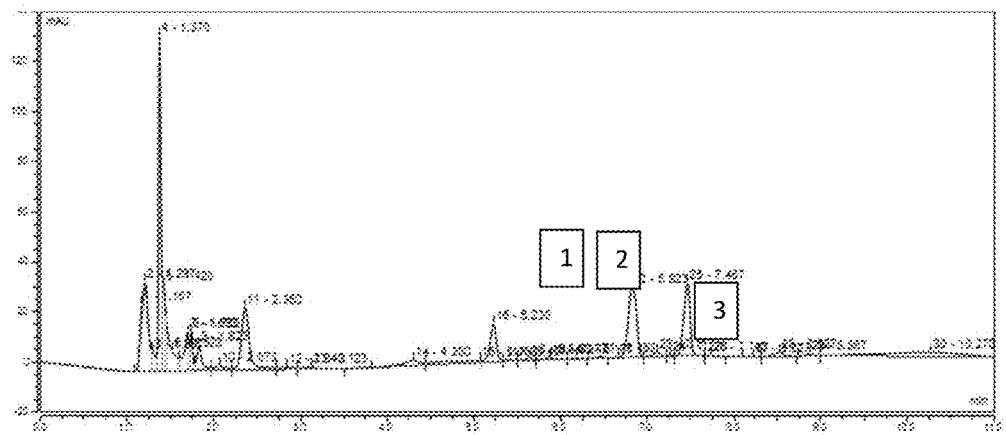
Figure 6:
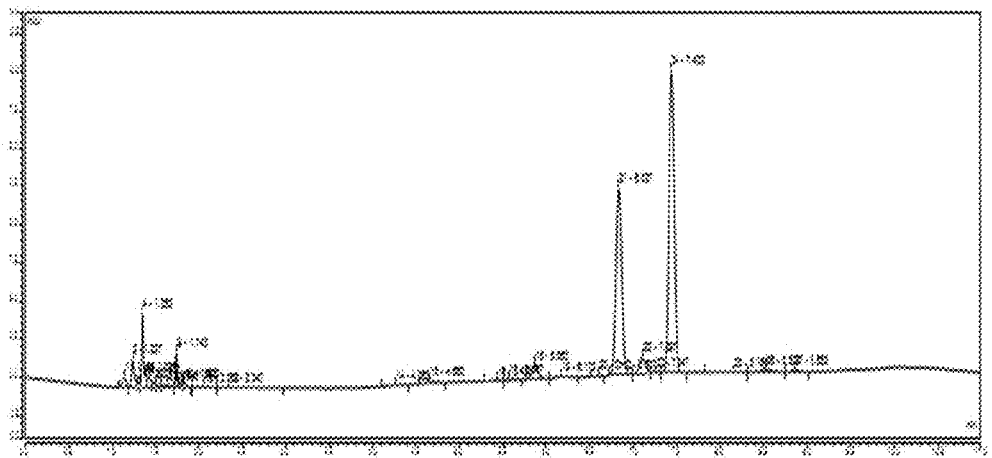
FIG. 6 is a chromatogram showing the bioconversion of coniferyl alcohol to ferulic acid in E. coli containing the gene products of MtSAD1 and AtADH.
Figure 7:
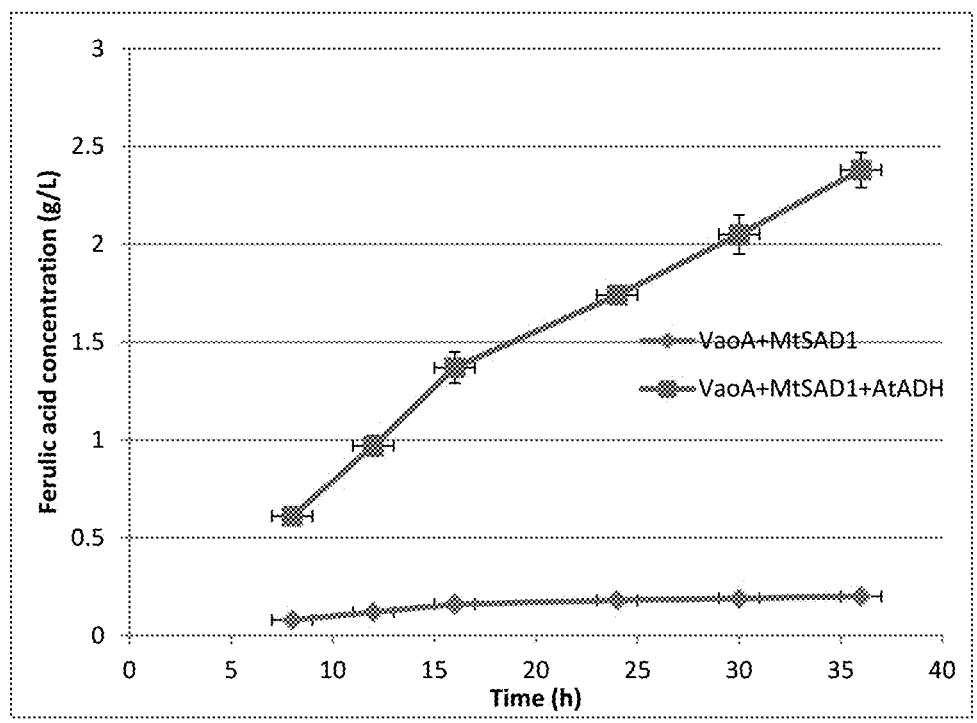
FIG. 7 is a line graph showing in vivo production of ferulic acid with eugenol in E. coli in M9A medium.

FIG. 1 illustrates the known and novel enzymatic pathways from eugenol to ferulic acid to vanillin;

FIG. 2 provides a schematic diagram of a CgVaoA-pETDuet construct. The VaoA gene was cloned into Nde/Xho site of vector pETDuet, resulting in CgVaoA-pETDuet;

FIG. 3 provides a schematic diagram of a MtSADrbsAt-ADH-pRSFDuet construct. MtSAD and AtADH were linked with a rbs sequence of cgcagcAGGAGGttaag and cloned into Nde/Xho site of vector pRSFDuet. The two constructs, CgVaoA-pETDuet and MtSADrbsAtADH-pRSFDuet, were co-transformed into BL21 (DE3) cells;

FIG. 4 discloses the protein expression of MtSAD1 in *E. coli*. Arrow indicates the MtSAD1 protein;

FIGS. 5A-5B show the bioconversion of coniferyl alcohol by the gene product of MtSAD1. As shown in FIG. 5A (upper panel), *E. coli* cells expressing MtSAD1 converted coniferyl alcohol (Peak 1) fed in the culture to coniferylaldehyde (Peak 3). Surprisingly, it also produced ferulic acid (peak 2). As the conversion time increased, the levels of coniferylaldehyde decreased and accordingly the levels of ferulic acid increased (FIG. 5B, lower panel). Based on these observations, Applicants show that MtSAD1 protein is a bi-functional enzyme, bioconverting the alcohol to the aldehyde and further converts the aldehyde to ferulic acid;

FIG. 6 shows the bioconversion of coniferyl alcohol to ferulic acid in *E. coli* containing the gene products of MtSAD1 and AtADH which increased the in-vivo conversion of alcohol to ferulic acid;

FIG. 7 shows in vivo production of ferulic acid with eugenol in *E. coli* in M9A medium.

Figure 8:
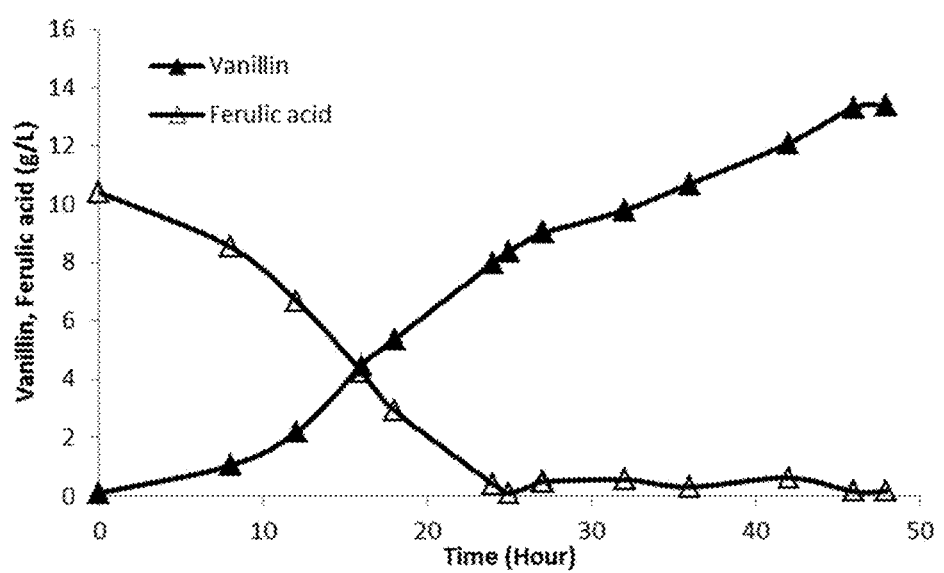
FIG. 8 is a line graph showing the production of vanillin with ferulic acid prepared from Eugenol.
Figure 9:
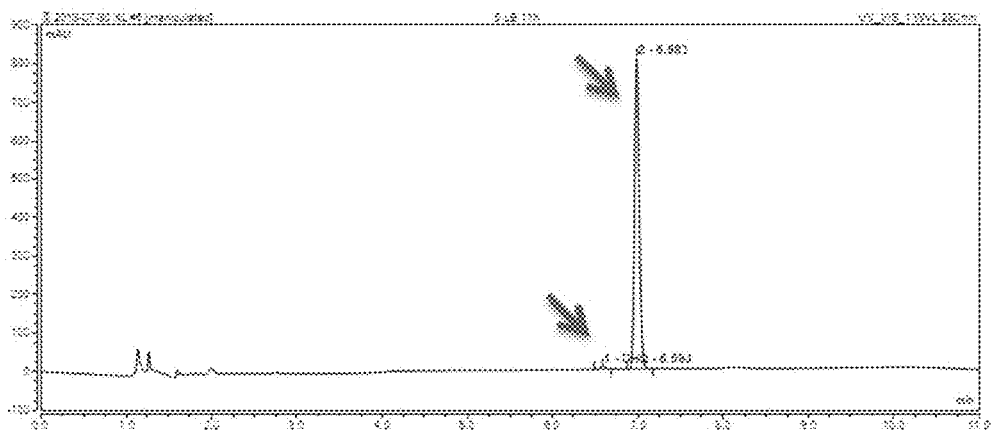
FIG. 9 is a chromatogram showing a recombinant E. coli strain comprising ech and fcs genes which bioconverts ferulic acid (blue (top) arrow) into vanillin (red (bottom) arrow) at a low efficiency in LB medium but at a relatively higher efficiency in M9A medium as all added ferulic acid was bioconverted into vanillin within 11 hours using bioconversion conditions.
Figure 10:
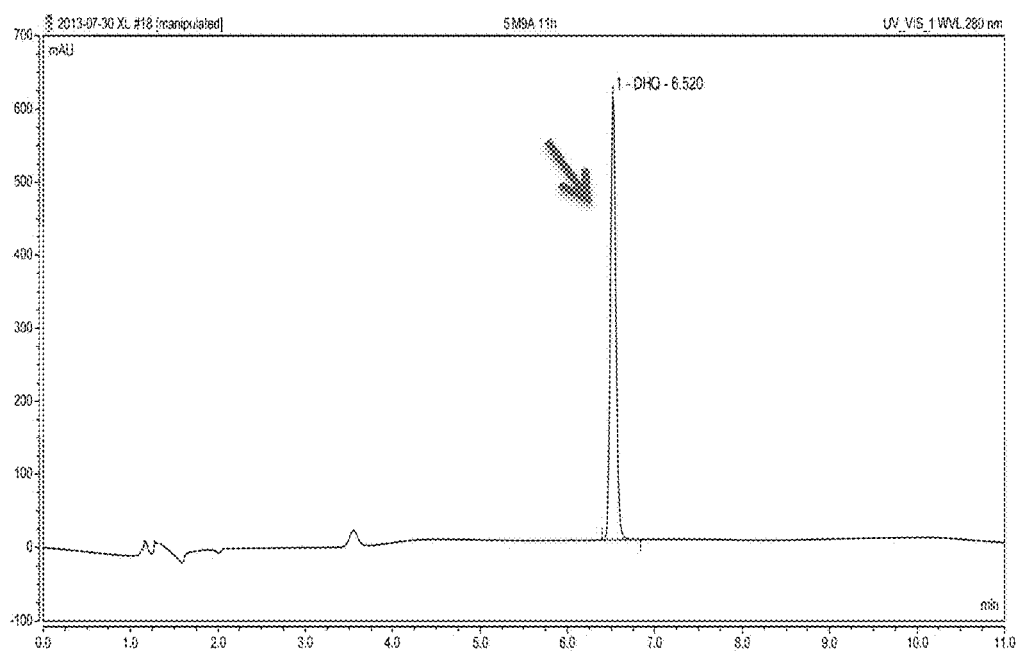
FIG. 10 is a chromatogram showing HPLC analysis of vanillin production in M9A medium where all added ferulic acid is converted into vanillin within 11 hours using bioconversion conditions.
Figure 11:
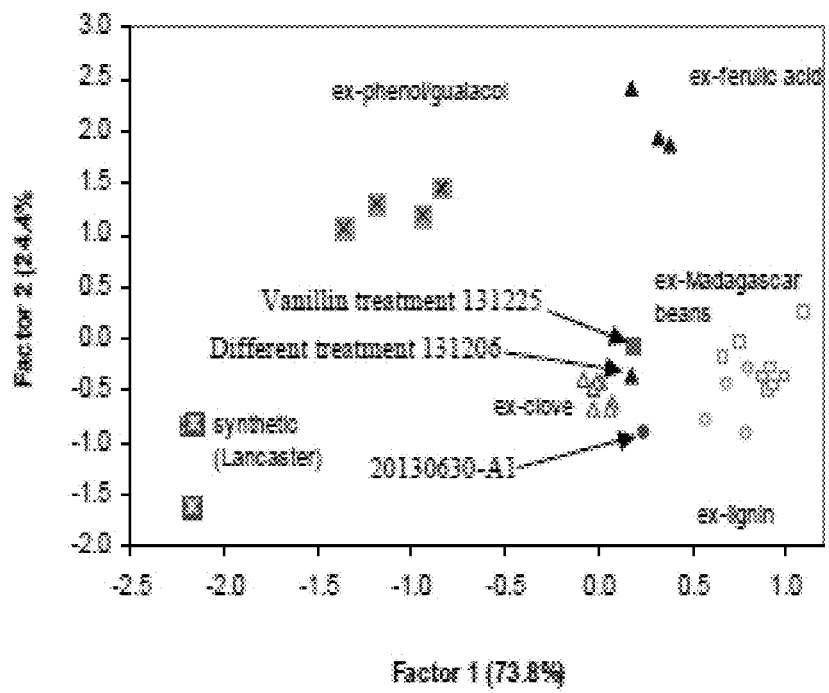
FIG. 11 is a data graph showing D-NMR results of various vanillin samples: synthetic vanillin (orange x's), ex-phenol/guaiacol (green x's), ex-ferulic acid (purple filled triangles), ex-clove (blue open triangles), ex-Madagascar beans (blue open squares), ex-lignin (purple open circles)
Figure 12:
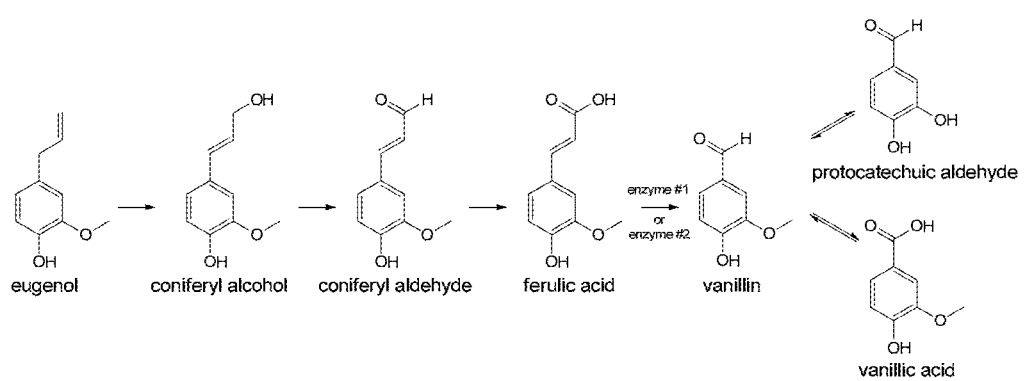
FIG. 12 shows a schematic pathway for the biotransformation of eugenol into vanillin and further transformation of vanillin into vanillic acid and protocatechuic aldehyde.

About 0.2 g/L ferulic acid was produced in the culture of *E. coli* with VaoA and MtSAD1 in 36 hours, but 2.4 g/L of ferulic acid was obtained with the introduction of AtADH in 25 mL shaker flasks;

FIG. 8 shows production of vanillin with ferulic acid prepared from Eugenol Applicants' result showed a yield of 13.4 g/L vanillin was obtained from 21.6 g/L ferulic acid (FA), corresponding to a molar yield of vanillin at 79.2%. The accumulation of vanillin is more or less linear over the fermentation period. However, the Applicant observed rapid FA reduction at the first 24 hours, suggesting *S. viridosporus* (Zhp06) bioconverts FA into different intermediates before being bioconverted to vanillin;

FIG. 9 shows a recombinant *E. coli* strain comprising ech and fcs genes can convert ferulic acid (blue (top) arrow) into vanillin (red (bottom) arrow) at a low efficiency in LB medium but at a relatively higher efficiency in M9A medium as all added ferulic acid was converted into vanillin within 11 hours using the bioconversion conditions;

FIG. 10 shows HPLC analysis of vanillin production in M9A medium where all added ferulic acid is converted into vanillin within 11 hours using the bioconversion conditions;

FIG. 11 shows D-NMR of various vanillin samples: synthetic vanillin-vanillin derived from petrochemical precursors (orange x's), ex-phenol/guaiacol (green x's), ex-ferulic acid (purple filled triangles), ex-clove-US "natural vanillin" from eugenol (blue open triangles), ex-Madagascar beans (blue open squares), ex-lignin (purple open circles); and FIG. 12 shows a schematic pathway for the biotransformation of eugenol into vanillin and further transformation of vanillin into vanillic acid and protocatechuic aldehyde.

EXAMPLES

Example 1. Production of Ferulic Acid from Eugenol in 25 mL (0.025 Liter) Shaker Flasks Cloning of a Short Chain Alcohol Dehydrogenase (MtSAD1) and Aldehyde Dehydrogenase (AtADH) from *Medicago truncatula* and *Arabidopsis*, Respectively.

MtSAD1 and AtADH were cloned from *Medicago truncatula* (ecotype A17) and *Arabidopsis thaliana* (ecotype Columbia-0). Plant total RNA was extracted with Trizol Plus RNA Purification Kit (Invitrogen Inc.). The synthesis of cDNA was carried out with Im Prom-II™ Reverse Transcription System from Promega Inc. following the manufacturer's manual. The genes were amplified from the synthesized cDNA with New England Biolab's Phusion PCR Kit with the primers listed in Table 2.

After digestion of the PCR products with corresponding restriction enzymes, MtSAD1 was inserted into the cloning site of Nde I and Xho I site of pRSFDuet-1 vector. AtADH was inserted into the cloning site of Bgl II and Xho I of pCDFDuet-1. After sequence confirmation, these constructs were introduced into BL21 (DE3) respectively. The nucleotide sequences are listed in Seq ID No 2 and Seq ID No 4, respectively, the corresponding amino acid sequences are listed in Seq ID No 1 and Seq ID No 3.

TABLE 2

Primers used for the cloning of MtSAD1, AtADH and VaoA

| | | |
|---|---|---|
| MtSAD1-Nde_F | GGAATTCCATATGGCAGAAGCA TCATCCACTAACAGC | SEQ ID NO: 11 |
| MtSAD1-Xho_R | CCGCTCGAGTTATAATAGTTCA TATTTGCCATAAAC | SEQ ID NO: 12 |
| AtADH-Bgl_F | GAAGATCTGGAGAACGGCAAAT GCAACGGAG | SEQ ID NO: 13 |
| AtADH-Xho_R | CCGCTCGAGTTACATCCAAGGG GAATTGTGAAGAG | SEQ ID NO: 14 |
| VaoA-Nde_F | GGAATTCCATATGAGTAAAACC CAAGAATTTCGTC | SEQ ID NO: 15 |
| VaoA-Xho_R | CCGCTCGAGTTATAGCTTCCAG GTTACGTGGC | SEQ ID NO: 16 |

SEQ ID No: 1. Amino sequence of MtSAD1:
MAEASSTNSGLRLAGKVAIVTGGASGIGKETAHLFAEQGARMVVIADIQDELGNQVAASIGSRKCTYIHCDI
ANEDQVKNLVQSTVNAYGQIDIMFSNAGIASPSDQTILELDISQADHVFAVNIRGTTLCVKYAARAMVEGRV
RGSIVCTASVLGSQGVLRLTDYTISKHAIIGLMRSASVQLAKYGIRVNCVSPNGLATPLTMKLLGASAKTVE
LIYEQNKRLEGVVLNTKHVADAVLFLVSNESDFVTGLDLRVDGSYVYGKYELL.

DNA sequence of MtSAD1.
Seq ID No: 2
ATGGCAGAAGCATCATCCACTAACAGCGGTCTTAGGTTAGCCGGCAAAGTAGCCATCGTCACCGGAGGTGCC
AGCGGCATTGGCAAAGAGACGGCACATCTCTTTGCCGAACAAGGTGCACGCATGGTGGTGATTGCCGACATC
CAAGACGAGTTGGGCAATCAAGTGGCTGCATCCATTGGCAGTCGCAAGTGCACCTACATTCATTGTGATATA
GCAAATGAAGATCAAGTTAAAAATCTCGTTCAATCAACTGTCAATGCTTATGGACAGATAGATATTATGTTT
AGCAATGCTGGGATTGCAAGTCCATCTGATCAGACTATTTTGGAACTCGACATTTCTCAAGCCGACCATGTG
TTTGCAGTTAACATTCGAGGAACGACATTGTGTGTGAAATACGCGGCACGTGCGATGGTGGAGGGGCGCGTG
AGGGGTAGCATTGTGTGCACAGCGAGCGTATTGGGTAGCCAAGGTGTCTTGAGGTTAACCGATTACACAATA
TCGAAGCATGCAATAATAGGGTTGATGCGCTCAGCGAGTGTGCAACTTGCAAAATACGGGATAAGAGTGAAT
TGTGTCTCGCCAAATGGATTAGCAACACCATTGACTATGAAATTGTTAGGGGCAAGTGCTAAGACAGTCGAG
TTGATTTATGAACAAAACAAGAGGTTGGAAGGAGTGGTTCTCAACACTAAACATGTTGCAGATGCTGTGTTG
TTCTTGGTATCTAATGAATCTGACTTTGTCACTGGCCTTGATCTTCGTGTGGATGGCAGCTATGTTTATGGC
AAATATGAACTATTATAA Protein sequence of AtADH.
Seq ID. No: 3
MENGKCNGATTVKLPEIKFTKLFINGQFIDAASGKTFETIDPRNGEVIATIAEGDKEDVDLAVNAARYAFDH
GPWPRMTGFERAKLINKFADLIEENIEELAKLDAVDGGKLFQLGKYADIPATAGHFRYNAGAADKIHGETLK
MTRQSLFGYTLKEPIGVVGNIIPWNFPSIMFATKVAPAMAAGCTMVVKPAEQTSLSALFYAHLSKEAGIPDG
VLNIVTGFGSTAGAAIASHMDVDKVSFTGSTDVGRKIMQAAAASNLKKVSLELGGKSPLLIFNDADIDKAAD
LALLGCFYNKGEICVASSRVFVQEGIYDKVVEKLVEKAKDWTVGDPFDSTARQGPQVDKRQFEKILSYIEHG
KNEGATLLTGGKAIGDKGYFIQPTIFADVTEDMKIYQDEIFGPVMSLMKFKTVEEGIKCANNTKYGLAAGIL
SQDIDLINTVSRSIKAGIIWVNCYFGFDLDCPYGGYKMSGNCRESGMDALDNYLQTKSVVMPLHNSPWM.

DNA sequence of AtADH.
Seq ID No: 4
ATGGAGAACGGCAAATGCAACGGAGCCACGACGGTGAAGTTACCGGAGATCAAATTCACCAAGCTTTTCATC
AACGGCCAGTTCATTGATGCTGCTTCAGGGAAGACGTTTGAGACGATAGACCCTAGGAACGGTGAAGTGATC
GCAACAATAGCCGAAGGAGACAAAGAAGACGTTGACTTGGCCGTTAACGCTGCACGTTACGCCTTCGACCAT
GGTCCTTGGCCTCGCATGACCGGCTTCGAGAGGGCAAAGCTTATCAACAAATTCGCAGACTTAATAGAGGAA
AACATTGAGGAATTGGCTAAACTTGATGCGGTTGACGGTGGAAAATTGTTTCAGTTGGGAAAATATGCTGAT
ATTCCGGCCACAGCCGGTCATTTTCGATACAATGCGGGTGCAGCAGATAAAATCCACGGCGAGACTCTTAAA -continued

```
ATGACGCGTCAATCTTTGTTCGGATACACCCTCAAAGAACCAATTGGAGTGGTTGGTAATATCATCCCTTGG
AATTTCCCAAGCATTATGTTTGCCACAAAGGTGGCTCCGGCTATGGCTGCTGGTTGCACCATGGTGGTCAAG
CCAGCTGAACAGACTTCACTCTCTGCTTTGTTCTATGCCCATCTCTCAAAAGAAGCGGGAATTCCTGATGGT
GTGCTCAACATTGTAACTGGTTTTGGATCAACTGCTGGAGCTGCCATTGCCTCCCATATGGACGTAGACAAA
GTTAGTTTCACTGGGTCAACAGATGTTGGAAGGAAGATAATGCAAGCCGCAGCCGCAAGTAATCTCAAAAAA
GTTTCCCTTGAATTAGGCGGGAAATCGCCACTTCTCATATTCAACGACGCTGATATTGACAAAGCCGCCGAT
CTTGCGCTTCTCGGTTGCTTTTACAACAAGGGTGAAATTTGCGTGGCGAGCTCTCGTGTGTTTGTTCAAGAA
GGTATATACGATAAGGTTGTGGAGAAGTTAGTAGAGAAGGCTAAAGATTGGACCGTTGGTGATCCTTTTGAT
TCCACTGCTCGACAAGGACCTCAAGTGGATAAAAGACAGTTTGAGAAGATTCTATCTTACATTGAGCACGGT
AAAAACGAAGGAGCGACCTTATTAACTGGAGGAAAAGCCATTGGAGACAAAGGATATTTCATCCAACCAACT
ATATTCGCAGATGTCACTGAGGATATGAAGATATACCAAGATGAAATCTTTGGACCAGTCATGTCACTGATG
AAATTCAAGACGGTAGAGGAAGGGATCAAATGCGCAAACAACACGAAATACGGTCTTGCAGCAGGAATACTA
AGCCAAGACATAGACTTGATCAACACGGTTTCGAGGTCAATCAAAGCTGGAATCATTTGGGTTAATTGCTAC
TTCGGGTTTGATCTTGACTGTCCTTATGGTGGCTACAAGATGAGTGGTAATTGTCGTGAAAGTGGCATGGAC
GCTCTCGACAACTATCTACAAACCAAATCCGTCGTTATGCCTCTTCACAATTCCCCTTGGATGTAA
```

Construction of VaoA Expression Vector.

VaoA gene was synthesized with the codon optimization in *E. coli* as the DNA sequence listed below resulting in the protein sequence.

```
Protein sequence of VaoA.
                                                   SEQ ID No: 5
MSKTQEFRPLTLPPKLSLSDFNEFIQDIIRIVGSENVEVISSKDQIVDGSYMKPTHTHDPHHVMDQDYFLAS
AIVAPRNVADVQSIVGLANKFSFPLWPISIGRNSGYGGAAPRVSGSVVLDMGKNMNRVLEVNVEGAYCVVEP
GVTYHDLHNYLEANNLRDKLWLDVPDLGGGSVLGNAVERGVGYTPYGDHWMMHSGMEVVLANGELLRTGMGA
LPDPKRPETMGLKPEDQPWSKIAHLFPYGFGPYIDGLFSQSNMGIVTKIGIWLMPNPGGYQSYLITLPKDGD
LKQAVDIIRPLRLGMALQNVPTIRHILLDAAVLGDKRSYSSKTEPLSDEELDKIAKQLNLGRWNFYGALYGP
EPIRRVLWETIKDAFSAIPGVKFYFPEDTPENSVLRVRDKTMQGIPTYDELKWIDWLPNGAHLFFSPIAKVS
GEDAMMQYAVTKKRCQEAGLDFIGTFTVGMREMHHIVCIVFNKKDLIQKRKVQWLMRTLIDDCAANGWGEYR
THLAFMDQIMETYNWNNSSFLRFNEVLKNAVDPNGIIAPGKSGVWPSQYSHVTWKL
DNA sequence of VaoA.
                                                   SEQ ID No: 6
ATGAGTAAAACCCAAGAATTTCGTCCGCTGACCTTACCTCCGAAATTAAGCCTGTCAGATTTTAACGAATTT
ATACAAGACATCATAAGGATAGTGGGTAGCGAGAACGTAGAGGTTATCAGTAGCAAAGATCAAATCGTGGAT
GGCAGCTACATGAAGCCGACCCATACCCATGACCCGCACCACGTTATGGATCAAGATTATTTTCTGGCAAGC
GCTATCGTCGCACCGCGTAACGTTGCAGACGTTCAAAGCATTGTTGGTCTGGCAAACAAATTCAGCTTCCCG
CTGTGGCCGATTAGCATCGGTCGTAACAGCGGTTACGGTGGAGCAGCACCGCGTGTTAGCGGTAGCGTTGTT
CTCGATATGGGCAAAAACATGAATCGTGTTCTGGAAGTTAATGTGGAAGGTGCCTATTGTGTTGTTGAACCG
GGTGTTACCTATCATGATCTGCATAATTATCTGGAAGCCAATAACCTGCGTGATAAGCTGTGGCTGGACGTT
CCAGACCTGGGTGGTGGCAGCGTACTGGGTAACGCAGTAGAACGTGGAGTTGGTTACACCCCGTATGGTGAC
CACTGGATGATGCATAGCGGTATGGAGGTTGTGCTGGCAAACGGTGAGCTGCTGCGTACCGGTATGGGTGCA
CTGCCAGACCCGAAGCGACCGGAGACAATGGGTCTGAAGCCGGAGGATCAACCGTGGTCAAAGATTGCACAC
CTGTTTCCGTATGGTTTTGGTCCGTATATTGATGGTCTGTTTAGTCAGAGCAACATGGGTATTGTTACCAAA
ATTGGCATTTGGCTGATGCCGAATCCGGGTGGTTATCAGAGCTATCTGATTACCCTGCCGAAAGATGGTGAT
```

```
                                    -continued
CTGAAACAGGCAGTTGATATTATCCGTCCGCTGCGTCTGGGTATGGCACTGCAGAATGTTCCGACCATTCGT

CATATTCTGCTGGATGCCGCAGTTCTGGGTGATAAACGTAGCTATAGCAGTAAAACCGAACCGCTGAGTGAT

GAAGAACTGGATAAAATTGCAAAACAGCTGAATCTGGGTCGCTGGAACTTTTATGGTGCACTGTATGGTCCG

GAACCGATTCGTCGTGTGCTGTGGGAAACCATTAAAGATGCATTTAGCGCAATTCCGGGTGTGAAATTCTAT

TTTCCGGAAGATACACCGGAAAATTCAGTTCTGCGTGTTCGTGATAAAACCATGCAGGGTATTCCGACCTAT

GATGAACTGAAATGGATTGATTGGCTGCCGAATGGTGCCCACCTCTTTTTTAGCCCGATAGCAAAGTTAGC

GGAGAGGACGCGATGATGCAGTATGCAGTGACCAAAAAACGTTGTCAAGAAGCAGGTCTGGATTTTATTGGC

ACCTTTACCGTTGGTATGCGTGAAATGCATCATATTGTGTGCATCGTGTTTAACAAAAAAGACCTGATTCAG

AAACGCAAGGTTCAATGGCTTATGCGTACACTGATAGACGATTGCGCAGCTAACGGTTGGGGTGAGTACCGT

ACACACCTAGCATTTATGGATCAGATCATGGAGACGTATAATTGGAATAACAGCAGCTTTCTGCGCTTTAAT

GAAGTTCTGAAAAATGCCGTTGATCCGAATGGTATTATCGCACCGGGTAAAAGCGGCGTATGGCCTAGCCAG

TATAGCCACGTAACCTGGAAGCTATAA
```

The gene was amplified with PCR as described above with the primers listed in Table 2. The PCR product was recovered from the agarose gel and digested with Nde I and Xho I, and then inserted into the Nde I and Xho I site of pETDuet-1 expression vector. The expression vector was then transformed into Topo 10 competent cells. The construct with the correct insert was confirmed by sequencing and was named VaoA-pETDuet.

Co-Expression of VaoA and MtSAD1 in E coli.

Plasmids of VaoA-pETDuet and MtSAD1-pRSFDuet were co-transformed into E. coli BL21 (DE3) competent cells according to the routine protocol. The colonies growing in LB plate with kanamycin and ampicillin were picked up for colony PCR verification of the presence of the two exogenous genes. The positive colony was used for the bioconversion study.

Co-Expression of VaoA, MtSAD1 and AtADH in E. coli.

Plasmids of VaoA-pETDuet, MtSAD1-pRSFDuet and AtADH-pCDFDuet were co-transformed into E. coli BL21 (DE3) competent cells according to routine protocol. The colonies growing in LB plate with kanamycin, ampicillin and spectinomycin were checked for the presence of the three exogenous genes by colony PCR. The positive colony was used for the bioconversion study.

FIG. 2 provides a schematic diagram of a CgVaoA-pETDuet construct. The VaoA gene was cloned into Nde/Xho site of vector pETDuet, resulting in CgVaoA-pETDuet.

FIG. 3 provides a schematic diagram of a MtSADrbsAtADH-pRSFDuet construct. MtSAD and AtADH were linked with a rbs sequence of cgcagcAGGAGGttaag and cloned into Nde/Xho site of vector pRSFDuet. The two constructs, CgVaoA-pETDuet and MtSADrbsAtADH-pRSFDuet, were co-transformed into BL21(DE3) cells.

The new recombinant E. coli strain comprising both plasmids CgVaoA-pETDuet and MtSADrbsAtADH-pRSFDuet bioconverts eugenol to ferulic acid.

Bioconversion of Coniferyl Alcohol.

E coli BL21 (DE3) containing MtSAD1 or MtSAD1+ AtADH was grown in M9 medium plus 1.25 g/L yeast extract with 50 µg/L ampicillin and 100 µg/L spectinomycin to OD600=0.6 in a shaker at 37° C., and then changed to 30° C. with addition of lactose to final concentration of 1.5% (w/v) to induce the expression of the two genes. After 8 hours of expression induction, coniferyl alcohol dissolved in 50% methanol was added to the culture. The culture was kept shaking under the same culture condition, and samples were taken at interval for HPLC analysis.

Bioconversion of Eugenol to Ferulic Acid.

E coli BL21 (DE3) containing VaoA, MtSAD1 and AtADH was grown in M9A medium plus 1.25 g/L yeast extract with 50 µg/L ampicillin and 100 µg/L spectinomycin to OD600=0.6 in a shaker at 37° C., and then changed to 30° C. with addition of lactose to final concentration of 1.5% (w/v) to induce the expression of the two genes. After 8 hours of expression induction, eugenol was added to the medium at the rate of 0.1 mL/hour per liter of the culture. The culture was kept shaking under the same culture condition, and samples were taken at interval for HPLC analysis.

Transformation of Ferulic Acid to Vanillin in Fermentor.

S. viridosporus seed medium used is Glucose Yeast Extract (GYE) medium and fermenter medium components are: Yeast extract, 8 g/L; glucose, 30 g/L; $MgSO_4.7H_2O$, 0.8 g/L; $Na_2HPO_4*7H_2O$, 7.5 g/L; $KH_2PO_4$, 1.0 g/L; and 0.2 mL/L antifoam. The medium were autoclaved at 120° C. for 15 and 30 minutes respectively.

Single S. viridosporus [renamed Amycolatopsis sp. strain (Zhp06)] colony was inoculated into TSB and shaken at 30° C. until the late exponential phase, and then sub-cultured into 2 L fermentor at 5%. The fermentor (New Brunswick Scientific Bioflo-115 3.0 L) was controlled at 30° C. to maintain DO above 20% with rpm and aeration. pH was controlled at 7 during the growth. Freshly made ferulic acid (FA) stock solution in 1 M NaOH was fed into fermentor at about 10% during early stationary phase and concentration of FA, vanillin and vanillin alcohol was followed by HPLC assay. When FA depleted from the culture, new batch of FA solution was fed to fermentor to continue the biotransformation. The process for converting FA to natural vanillin (NV) using Amycolatopsis sp. strain (Zhp06) is described in detail in US2013/00115667A1 and CN102321563B1, the contents of which are incorporated herein by reference.

HPLC Analysis.

The HPLC analysis of ferulic and eugenol was carried out with Dionex Ultimate 3000 system. Intermediates were separated by reverse-phase chromatography on a Dionex Acclaim 120 C18 column (particle size 3 am; 150 by 2.1 mm) with a gradient of 0.15% (vol/vol) acetic acid (eluant A) and acetonitrile (eluant B) in a range of 10 to 40% (vol/vol) eluant B and at a flow rate of 0.6 ml/min. For quantification, all intermediates were calibrated with external standards. The compounds were identified by their retention times, as well as the corresponding spectra, which were identified with a diode array detector in the system.

Isotopic Analysis of Vanillin Obtained Through Fermentation and the Ferulic Acid Substrate.

Different sources of ferulic acid, along with several batch of biotransformed vanillin were analyzed for 613C analysis by EA-IRMS at Isotech Laboratories, Inc. (Champaign, Ill.).

Results I

MtSAD1 Protein is Bi-Functional.

MtSAD1 protein showed bi-functional activity in catalyzing the conversion of coniferyl alcohol to coniferylaldehyde and the conversion of coniferyladehyde to ferulic acid. As shown in FIG. 2, MtSAD1 gene product was successfully expressed in *E. coli* tested by SDS-PAGE. The MtSAD1 protein existed in both soluble and insoluble fractions.

MtSAD1 Protein Catalyzes the Conversion of Coniferyl Alcohol to Coniferylaldehyde; it Also Converts the Latter to Ferulic Acid.

As shown in FIG. 5A (upper panel), *E. coli* cells with the expression of MtSAD1 converted coniferyl alcohol (Peak 1) fed in the culture to coniferylaldehyde (Peak 3). Surprisingly, it also produced ferulic acid (peak 2). As the conversion time increased, the levels of coniferylaldehyde decreased and accordingly the levels of ferulic acid increased (FIG. 5B, lower panel). Based on these observations, applicants show that MtSAD1 protein is a bi-functional enzyme, converting the alcohol to the aldehyde and further converts the aldehyde to ferulic acid.

The Presence of AtADH Protein Improved the Conversion Efficiency of Eugenol to Ferulic Acid in *E. coli*.

From the above results, Applicants appreciate that the catalytic efficiency is low for industrial utilization. An aldehyde dehydrogenase was cloned from *Arabidopsis* (AtADH). *E. coli* cells with co-expression of MtSAD1 and AtADH dramatically increased the in vivo conversion of alcohol to ferulic acid (FIG. 4).

Production of Ferulic Acid with Eugenol in *E coli* Containing VaoA, MtSAD1 and AtADH.

*E. coli* cells with the expression of VaoA, MtSAD1 can convert eugenol to ferulic acid. With the introduction of AtADH, the production of ferulic acid was dramatically increased. About 0.2 g/L ferulic acid was produced in the culture of *E. coli* with VaoA and MtSAD1 in 36 hours, but 2.4 g/L of ferulic acid was obtained with the introduction of AtADH (FIGS. 5A-5B) in 25 mL shaker flasks.

Example 2A. Production of Ferulic Acid with Eugenol in a 30 L Volume in a 50-Liter Fermenter One milliliter of glycerol stock solution with the *E. coli* cells harboring CgVaoA-pETDuet and MtSADrbsAtADH-pRSFDuet was inoculated into 1 L LB medium containing 100 mg/L ampercillin and 30 mg/L kanamycin and cultured at 37° C. overnight as the seed, which was then transferred into 30 liter LB medium containing 100 mg/L ampercillin and 30 mg/L kanamycin in 50-liter fermenter. Set initial temperature at 37° C., agitation at 300 rpm, dissolved oxygen (DO) maintained at over 30%, air at 0.6 vvm without the control of pH at the beginning. After 1 to 1.5 hours, reduce the temperature to 30 C, added 2 L of 22.5 g/L lactose, making the final concentration to 15 g/L to start induction. The volume is approximately 33-34 Liters at this time. Maintain air at 0.6 vvm, increase agitation to 350 rpm, maintain DO above 15%. After fermentation for 14 to 16 hours, add substrate eugenol with the temperature was kept at 30 C, air at 0.6 vvm, agitation at 350 rpm, and DO above 15%. The speed of eugenol addition is as follows: eugenol at about 0.67%/h/L fermentation broth at 16-32 hours, reduced to about 0.4%/h/L at 32 to 48 hours, and further reduced to about 0.3%/h/L after that until the end at 72 hours. Samples were taken from the fermenter at interval for HPLC analysis.

Results 2A

High conversion of FA from eugenol was achieved in our fermentation study. On average, the titer of around 25-30 g/L was obtained under our study condition with very little accumulation of the intermediate product coniferyl alcohol (CA) (Table 3).

TABLE 3

The bioconversion of eugenol to ferulic acid in 50-liter fermenter.

| Fermentation time (h) | OD600 | FA (g/L) | CA (g/L) |
|---|---|---|---|
| 1.2 | 1.08 | | |
| 16 | 17.08 | 0 | |
| 19 | 16.96 | 1.83 | |
| 22 | 17.55 | 3.92 | |
| 40 | 16.12 | 14.86 | |
| 43 | 15.69 | 16.80 | 0.06 |
| 46 | 15.25 | 18.69 | 0.03 |
| 64 | 14.01 | 26.29 | 0.05 |

Comparative Data

Overhage et al (Appl Env Microbiol (2003) 69; 6569-6576) disclose a biotransformation process for converting eugenol to ferulic acid and further conversion to vanillin in recombinant strains of *E. coli*. The biotransformation process was successfully transferred to a 30 L scale where a ferulic acid concentration of 14.7 g/l after a total fermentation time of 30 hours was obtained. No data/information was provided on whether the process could be enhanced to improve yields by extending the incubation time. It was reported in US 20140087428A that the yields of vanillin (0.3 g/l vanillin after 2 hours) obtained using a second recombinant *E. coli* strains were too low for an economically feasible process.

The successful adoption of metabolic engineering approaches in *E. coli* can offer a low cost and industrially economical process for vanillin production. A bioconversion/biotransformation process for converting eugenol to ferulic acid in a recombinant strain of *E. coli* is disclosed. The known bacterial CalA/CalB genes of *Pseudomonas* sp. HR199 (as disclosed in Overhage et al 2003 Appl Env Microbiol (2003) 69; 6569-6576) were replaced with plant based genes (MtSAD1 and AtADH1) which successfully converted eugenol to coniferyl alcohol, coniferyl aldehyde and finally to ferulic acid. Ferulic acid (26 g/l) was recovered after 64 hours of incubation when this biotransformation was scaled up to 30 L fermentation volume.

Example 2B. Bioconversion of Ferulic Acid to Vanillin

The purified ferulic acid (FA) converted from eugenol with our VaoA-MtSAD1-AtADH system was used as a substrate for vanillin production. FA was converted to natural vanillin (NV) using *Amycolatopsis* sp. strain (Zhp06)] and the process as described in US 2013/0115667A1 and CN102321563B1. Applicants' result showed a yield of 13.4 g/L vanillin was obtained from 21.6 g/L FA, corresponding to a molar yield of vanillin at 79.2% (FIG. 8). The accumulation of vanillin is more or less linear over the fermentation period. However, the Applicant observed rapid FA reduction at the first 24 hours, suggesting *S. viridosporus* converts FA into different intermediates before being converted to vanillin.

Example 3. The Development of E. coli Strain for Producing Vanillin with Ferulic Acid The vanillin producing genes ech (Enoyl-CoA Hydrataase/Aldosase) and fcs (trans-feruloyl-CoA synthase) were cloned in *E. coli* to produce natural vanillin.

Exemplary Methods
Construction of AmFCS Expression Vector.
AmFCS gene was synthesized with the codon optimization in *E. coli* as the sequence listed below. The gene was amplified with PCR and inserted into the Nde I and Xho I site of pCDFDuet-1 expression vector, resulting in a plasmid of AmFCS-pCDFDuet.

SEQ ID NO. 7: nucleotide sequence for FCS
ATGCGTAATCAGGGTCTGGGTAGCTGGCCGGTTCGTCGTGCTCGTATGTCCCCGCATGCAACGGCTGTTCGTCACGGTGG

TACGGCGCTGACCTATGCCGAACTGAGTCGTCGTGTGGCACGTCTGGCAAACGGTCTGCGTGCAGCAGGTGTGCGTCCGG

GTGATCGCGTTGCGTATCTGGGTCCGAATCATCCGGCCTACCTGGAAACCCTGTTTGCATGCGGCCAGGCCGGTGCAGTT

TTTGTCCCGCTGAACTTCCGTCTGGGCGTTCCGGAACTGGATCACGCTCTGGCGGACTCAGGTGCCTCGGTGCTGATTCA

TACCCCGGAACACGCAGAAACGGTTGCAGCTCTGGCAGCAGGTCGTCTGCTGCGCGTCCCGGCAGGTGAACTGGATGCAG

CTGATGACGAACCGCCGGACCTGCCGGTTGGTCTGGATGACGTCTGCCTGCTGATGTATACCAGTGGCTCCACGGGTCGT

CCGAAAGGCGCGATGCTGACCCACGGCAATCTGACGTGGAACTGTGTGAATGTTCTGGTCGAAACCGATCTGGCCAGCGA

CGAACGTGCACTGGTGGCAGCACCGCTGTTTCATGCAGCTGCGCTGGGTATGGTGTGCCTGCCGACCCTGCTGAAAGGCG

GTACGGTTATTCTGCACAGTGCGTTTGATCCGGGCGCTGTGCTGTCCGCGGTTGAACAGGAACGTGTCACCCTGGTGTTC

GGTGTTCCGACGATGTACCAAGCTATCGCAGCACATCCGCGTTGGCGTAGCGCAGATCTGAGCTCTCTGCGCACCCTGCT

GTGTGGTGGTGCACCGGTGCCGGCTGATCTGGCGTCTCGTTATCTGGACCGCGGCCTGGCGTTCGTTCAAGGCTACGGTA

TGACCGAAGCTGCGCCGGGTGTGCTGGTTCTGGATCGTGCCCACGTGGCAGAAAAAATTGGCAGCGCGGGTGTCCCGAGC

TTTTTCACGGATGTTCGTCTGGCAGGTCCGTCAGGTGAACCGGTTCCGCCGGGCGAAAAAGGTGAAATCGTGGTTTCGGG

CCCGAACGTGATGAAAGGCTATTGGGGTCGTCCGGAAGCCACCGCAGAAGTTCTGCGCGATGGCTGGTTTCATTCTGGTG

ACGTCGCCACGGTGGATGGCGACGGTTATTTCCACGTCGTGGATCGTCTGAAAGACATGATTATCAGCGGCGGTGAAAAC

ATTTACCCGGCGGAAGTTGAAAATGAACTGTATGGCTACCCGGGTGTCGAAGCTTGTGCGGTTATCGGCGTGCCGGACCC

GCGTTGGGGTGAAGTGGGTAAAGCTGTTGTCGTGCCGGCAGACGGCAGTCGCATCGATGGTGACGAACTGCTGGCTTGGC

TGCGTACCCGTCTGGCAGGTTACAAAGTCCCGAAATCCGTGGAATTCACGGATCGCCTGCCGACCACGGGCTCCGGTAAA

ATCCTGAAAGGCGAAGTGCGTCGTCGTTTTGGCTAA

SEQ ID NO: 8 Amino acid sequence for FCS:
MRNQGLGSWPVRRARMSPHATAVRHGGTALTYAELSRRVARLANGLRAAGVRPGDRVAYL

GPNHPAYLETLFACGQAGAVFVPLNFRLGVPELDHALADSGASVLIHTPEHAETVAALAA

GRLLRVPAGELDAADDEPPDLPVGLDDVCLLMYTSGSTGRPKGAMLTHGNLTWNCVNVLV

ETDLASDERALVAAPLFHAAALGMVCLPTLLKGGTVILHSAFDPGAVLSAVEQERVTLVF

GVPTMYQAIAAHPRWRSADLSSLRTLLCGGAPVPADLASRYLDRGLAFVQGYGMTEAAPG

VLVLDRAHVAEKIGSAGVPSFFTDVRLAGPSGEPVPPGEKGEIVVSGPNVMKGYWGRPEA

TAEVLRDGWFHSGDVATVDGDGYFHVVDRLKDMIISGGENIYPAEVENELYGYPGVEACA

VIGVPDPRWGEVGKAVVVPADGSRIDGDELLAWLRTRLAGYKVPKSVEFTDRLPTTGSGK

ILKGEVRRRFG*

Construction of PfECH Expression Vector.
PfECH gene was synthesized with the codon optimization in *E. coli* as the sequence listed below. The gene was amplified with PCR and inserted into the Nde I and Xho I site of pRSFDuet-1 expression vector, resulting in a plasmid of AmFCS-pRSFDuet.

SEQ ID NO. 9: nucleotide sequence for ECH
ATGAGCACATACGAAGGTCGCTGGAAAACGGTCAAGGTCGAAATCGAAGACGGCATCGCGTTTGTCATCCTCAATCGCCC

GGAAAAACGCAACGCGATGAGCCCGACCCTGAACCGCGAGATGATCGATGTTCTGGAAACCCTGGAGCAGGACCCTGCCG

-continued

```
CCGGTGTGCTGGTGCTGACCGGTGCGGGCGAAGCCTGGACCGCAGGCATGGACCTCAAGGAATACTTCCGCGAAGTGGAC

GCCGGCCCGGAAATCCTCCAGGAAAAAATCCGCCGCGAAGCCTCGCAATGGCAATGGAAACTGCTGCGCATGTACGCCAA

GCCGACCATCGCGATGGTCAATGGCTGGTGCTTCGGCGGCGGTTTCAGCCCGCTGGTGGCCTGCGACCTGGCGATCTGCG

CCGACGAAGCAACCTTCGGTCTCTCGGAAATCAACTGGGGTATCCCGCCGGGCAACCTGGTGAGCAAGGCGATGGCCGAC

ACCGTGGGCCACCGCCAGTCGCTCTACTACATCATGACCGGCAAGACCTTCGGTGGGCAGAAAGCCGCCGAGATGGGCCT

GGTCAACGAAAGCGTGCCCCTGGCGCAACTGCGCGAAGTCACCATCGAGCTGGCGCGTAACCTGCTCGAAAAAAACCCGG

TGGTGCTGCGTGCCGCCAAACACGGTTTCAAACGCTGCCGCGAACTGACCTGGGAGCAGAACGAGGATTACCTGTACGCC

AAGCTCGATCAGTCGCGTTTGCTGGACACCGAAGGCGGTCGCGAGCAGGGCATGAAGCAATTCCTCGACGACAAGAGCAT

CAAGCCTGGCCTGCAACCGTATAAACGCTGA

SEQ ID NO: 10  Amino acid sequence for ECH:
MSTYEGRWKTVKVEIEDGIAFVILNRPEKRNAMSPTLNREMIDVLETLEQDPAAGVLVLT

GAGEAWTAGMDLKEYFREVDAGPEILQEKIRREASQWQWKLLRMYAKPTIAMVNGWCEGG

GESPLVACDLAICADEATFGLSEINWGIPPGNLVSKAMADTVGHRQSLYYIMTGKTFGGQ

KAAEMGLVNESVPLAQLREVTIELARNLLEKNPVVLRAAKHGFKRCRELTWEQNEDYLYA

KLDQSRLLDTEGGREQGMKQFLDDKSIKPGLQAYKR*
```

Co-Expression of AmFCS and PfECH in *E. coli*.

Plasmids of AmFCS-pCDFDuet and PfECH-pRSFDuet were co-transformed into BL21 (DE3). The colonies growing in LB plate with kanamycin and spectromycin were picked up for colony PCR check. The positive colony was used for the bioconversion study.

Bioconversion of Ferulic Acid to Vanillin.

*E coli* BL21(DE3) containing AmFCS-pCDFDuet and PfECH-pRSFDuet was grown in LB medium or M9A medium (14 g/L KH2PO4, 16 g/L K2HPO4, 1 g/L Na3Citrate.2H2O, 7.5 g/L (NH4)2SO4, 0.25 g/L MgSO4.7H2O, 0.015 g/L CaCl2.2H2O, 5 g/L of glucose) with 30 mg/L kanamycin and 50 mg/L spectinomycin to OD600=0.6 in a shaker at 37° C., and then changed to 30° C. with addition of IPTG to final concentration of 0.5 mM to induce the expression of the two genes. After 5 hours of expression induction, ferulic acid dissolved in 0.1 M NaOH (100 g/L) was added to the culture to final concentration of 2 g/L. The culture was kept shaking under the same culture condition, 1 g/L of ferulic acid was added to the culture after the first addition of ferulic acid, and samples were taken at interval for HPLC analysis.

HPLC Analysis.

The HPLC analysis of ferulic acid and vanillin was carried out with Dionex Ultimate 3000 system. Intermediates were separated by reverse-phase chromatography on a Dionex Acclaim 120 C18 column (particle size 3 μm; 150 by 2.1 mm) with a gradient of 0.15% (vol/vol) acetic acid (eluant A) and acetonitrile (eluant B) in a range of 10 to 40% (vol/vol) eluant B and at a flow rate of 0.6 ml/min. For quantification, all intermediates were calibrated with external standards. The compounds were identified by their retention times, as well as the corresponding spectra, which were identified with a diode array detector in the system.

As FIG. 9 shows, the recombinant *E. coli* strain converts ferulic acid (blue (top) arrow) into vanillin (red (bottom) arrow) in LB medium at a relatively low efficiency. A little vanillin was observed in LB culture after 11 hours of the addition of ferulic acid. In contrast, the conversion efficiency is relatively high in M9A medium as all added ferulic acid was converted into vanillin within 11 hours in our conversion conditions (FIG. 9). All of the total 3 g/L added ferulic acid was completed converted and the yield of vanillin was about 2.2 g/L after 24 hour conversion.

The vanillin producing genes ech and fcs were cloned in *E. coli* to produce natural vanillin with limited success in LB culture but with much improved conversion rates in M9A culture medium.

Example 4. δ13C (C13/C12) Isotope Analysis

Different sources of ferulic acid (eg from maize and eugenol), along with several batch of bioconverted/biotransformed vanillin were analyzed for $^{13}C/^{12}C$ ($\delta^{13}C$) analysis by EA-IRMS at Isotech Laboratories, Inc. (Isotech Laboratories, Inc. 1308 Parkland Court|Champaign Ill. 61821) (Table 4).

Ferulic acid/vanillin from maize was prepared in accordance with methods disclosed in WO 2014/106189A2, the entire contents of which are incorporated herein by reference.

Ferulic acid/vanillin from eugenol was prepared in accordance with the methods disclosed and claimed herein.

The $\delta^{13}C$ values were determined as follows:

The ratio for $^{13}C/^{12}C$ is reported as $\delta^{13}C$. The definition is, in per mil:

$$\delta^{13}C = \left\{ \frac{\left(\frac{^{13}C}{^{12}C}\right)_{sample}}{\left(\frac{^{13}C}{^{12}C}\right)_{standard}} - 1 \right\} \times 1000\%$$

where the standard is an established reference material.

The standard established for carbon-13 work was the Pee Dee Belemnite or (PDB) and was based on a Cretaceous marine fossil, *Belemnitella americana*, which was from the Pee Dee Formation in South Carolina. This material had an anomalously high $^{13}C{:}^{12}C$ ratio (0.0112372), and was established as $\delta^{13}C$ value of zero. Use of this standard gives most natural material a negative $\delta^{13}C$. The standards are used for verifying the accuracy of mass spectroscopy; as isotope studies became more common, the demand for the standard exhausted the supply. Other standards, including one known as VPDB, for Vienna PDB, have replaced the original.

$C_3$ and $C_4$ plants have different $\delta^{13}C$ signatures, allowing $C_4$ grasses to be detected using a $\delta^{13}C$ value measurement which can be summarised as follows:

According to one study (see Cochennec C Perfumer & Flavourist (2013) 38: 20-27), ferulic acid from $C_4$ plants (eg maize) has a $\delta^{13}C$ value in the range of −16 to −19‰ and vanillin from $C_3$ plants (eg rice) has a $\delta^{13}C$ value of −35 to −38‰.

According to another study (see Table from "Herkunf und Authentizitaet von Vanillearomen" in Lebensmittelchemie (2010) 64: 17-48)

$\delta^{13}C$ values for vanillin produced biotechnologically from C3 plants (eg rice) typically in the region of −36‰ to −37‰ VPDB;

Thus, $\delta^{13}C$ value for $C_4$ plants would generally be "less negative" or "greater" in value compared with the $\delta^{13}C$ value for $C_3$ plants.

Results 4

Carbon isotope ($\delta^{13}C$) analysis suggests that ferulic acid (FA) prepared from eugenol and the vanillin produced with this FA preparation according to the methods of the present disclosure have different $\delta^{13}C$ values from the $\delta^{13}C$ value for ferulic acid/vanillin from maize cob. Table 4 indicates that the $\delta^{13}C$ value for vanillin obtained from maize is −16.6‰. The average value range of $\delta^{13}C$ for vanillin prepared from maize cob FA is about −19 to −16.0‰ (see Cochennec C Perfumer & Flavourist (2013) 38; 20-27). In contrast, Table 4 indicates that a $\delta^{13}C$ value of about −32‰ was observed for ferulic acid (FA) and the resultant vanillin prepared from eugenol according to the methods of the present disclosure.

Without wishing to be bound by theory, the variation between the $\delta^{13}C$ values for ferulic acid/vanillin from these two different plant sources (ie maize and eugenol) may originate from the different photosynthetic pathways for the plant source starting materials. The plant from which most eugenol is derived is a $C_3$ plant which photosynthetically assimilates more $^{12}C$ than $^{13}C$, which potentially leads to a lower (ie more negative) $\delta^{13}C$ value for ferulic acid/vanillin from those plant materials compared with $C_4$ plants. As maize is a $C_4$ plant and its carbon dioxide fixation shows much less discrimination between $^{12}C$ and $^{13}C$, the $\delta^{13}C$ value for ferulic acid/vanillin obtainable from maize may be comparable to that in the environment.

TABLE 4

Isotopic analysis of vanillin and ferulic acid from different biomaterial sources

| Sample Number | Sample Code | Sample Name | $\delta^{13}C_{PDB}$ ‰) |
|---|---|---|---|
| 130034 | FA120322 | FA from Maize cob | −13.4 |
| 130035 | NV120915 | Vanillin converted from maize cob FA | −16.6 |
| 130036 | FA130420 | FA from eugenol | −31.8 |
| 130037 | NV130428 | NV converted from FA from eugenol | −32.5 |

Natural Ferulic Acid (FA)/Natural Vanillin (NV) (Ex Eugenol) is Different from FA/NV from Other Natural Plant Sources:

The results in Table 4 and in the cited prior art as discussed above demonstrate that at least $C_3$, $C_4$ and CAM plants have different $\delta^{13}C$ signatures allowing $C_3$, $C_4$ grasses and CAM plants to be detected and differentiated by their $\delta^{13}C$ values. In addition, the data in Table 4 indicates that natural ferulic acid and natural vanillin obtainable from eugenol using the methods of the present disclosure also have a $\delta^{13}C$ value (of about −32‰) which is different from the $\delta^{13}C$ value obtained from at least C3, C4 (such as, for example, from a natural plant group source selected from rice, maize, sugar beet, wheat and curcumin) and/or CAM plants ((eg the $\delta^{13}C$ value for vanilla extract from the traditional curing of the vanillin bean and/or from using an accelerated biologic process (see for example, WO2010/066060 and WO 2010/066061).

Example 5

A comparison of the $\delta^{13}C$ values for ferulic acid/vanillin obtained using the known bioconversion process described in Overhage et al (Appl Env Microbiol (2003) 69; 6569-6576) using VaoA/CalA and CalB genes and the bioconversion process of present disclosure using VaoA/MtSAD1 and AtADH genes was carried out. These bioconversion processes are termed "known" and "new" processes respectively.

Results 5

Surprisingly, the isotope analysis indicates the $\delta^{13}C$ is about −28.1 for vanillin obtained using the "new" process which is different from the $\delta^{13}C$ value of −31.7 for vanillin obtained using the "known" process.

TABLE 5

$\delta^{13}C$ values for vanillin derived from eugenol with alternative oxidation enzymes.

| Sample # | Oxidation Enzyme | $\delta^{13}C$ ‰ |
|---|---|---|
| 1 | 1 (known process) | −31.7 |
| 2 | 1 (known process) | −31.7 |
| 3 | 1 (known process) | −31.8 |
| 4 | 2 (new process) | −28.1 |
| 5 | 2 (new process) | −28.1 |
| 6 | 2 (new process) | −28.2 |

The known process (as disclosed in Overhage et al (Appl Env Microbiol (2003) 69; 6569-6576)) incorporating oxidation enzyme #1 (CalA) resulted in a δ13C value (of about −32‰). Replacement of oxidation enzyme #1 (CalA) with enzyme #2 (MtSAD1) resulted in a $\delta^{13}C$ value change from −31.7‰ to −28.1‰. In view of the data disclosed in Table 5 and the fact the different botanic sources of eugenol from different regions and territories may have different $\delta^{13}C$ values, the Applicants propose that the natural Ferulic acid/Vanillin acid obtainable from eugenol by the methods of the present disclosure has a $\delta^{13}C$ value range of from about −25 to −32‰.

Without wishing to be bound by theory, there are two proposed routes which may explain the observed change in $\delta^{13}C$ value. In the first case, enzyme #2 (MtSAD1) may have a secondary activity which demethylates vanillin to protocatechuic acid in a reversible reaction (see FIG. 12). During the reverse reaction, a methyl group derived from C4 based corn sugar used to grow the cells is incorporated onto protocatechuic acid resulting in vanillin. Because the original methyl group on a $C_3$ source is replaced with a C4 based methyl group, there is a change in the $\delta^{13}C$ value from the expected value.

The second route by which the change in $\delta^{13}C$ value may take place takes into account enzyme kinetics and the kinetic isotope effect. Enzyme #2 (MtSAD1) may cause additional oxidation of vanillin to vanillic acid as a secondary activity. The rate of aldehyde oxidation is different for each carbon isotope which can alter the $\delta^{13}C$ value for vanillin as portions are bled away as vanillic acid. Further studies will determine if vanillic acid is formed when enzyme #2 is incorporated in the pathway.

Example 6

A $\delta^{13}C$ value in the range of minus 25‰ to minus 32‰ has its own set of challenges because it cannot be reliably distinguished from artificially derived vanillin from guaiacol or lignin or US natural vanillin (which has a $\delta^{13}C$ value in the range of −28.7‰ to −26.5‰ (see Table 6 below)). Accordingly, a secondary D-NMR test was used which measured the enrichment of deuterium on the phenyl ring of vanillin from various sources.

Result 6

As FIG. 9 shows, clusters can be seen for vanillin from varying sources. Samples 20130630-A1 (red filled circle) and 131206 (blue filled triangle) were produced from two sources of eugenol using enzymes #1 (CalA) in the process. Sample 131225 represents vanillin obtained from eugenol which incorporates enzyme #2 (MtSAD1) in the process. All three samples cluster closely with but separately from ex-clove which corresponds with US "natural" vanillin derived from eugenol. Independently, the $\delta^{13}C$ values could be misinterpreted as artificial/adulterated vanillin (eg artificially derived vanillin from guaiacol or lignin) while the D-NMR results would suggest that the D-NMR method can distinguish natural vanillin from eugenol, natural vanillin from other sources and from artificially derived vanillin from guaiacol or lignin as well as US "natural" vanillin derived from eugenol.

In summary, a bioconversion process for producing ferulic acid/natural vanillin (FA/NV) from eugenol has been developed and disclosed herein but it may require two lines of evidence to prove that the FA/NV material is unique from those derived artificially, synthetically or by means not accepted in the EU.

TABLE 6

$\delta^{13}C$ value for vanillin from various sources (data obtained from "Herkunf und Authentizitaet von Vanillearomen" in Lebensmittelchemie (2010) 64: 17-48)

| Source | Regulatory Status | $\delta^{13}C$ ‰ |
|---|---|---|
| vanilla bean | natural | −21.5 to −19.2 |
| guaiacol | artificial | −36.2 to −24.9 |
| lignin | artificial | −28.7 to −26.5 |
| ferulic acid | Natural (ex rice) | −37.0 to −36.0 |
| ferulic acid | artificial | −37.0 to −36.0 |
| eugenol | US natural | −31.7 to −29.9 |

The present disclosure provides a fermentation based process which converts eugenol to vanillin that fits the regulatory requirements for a natural ingredient in the EU. The fermentation based process incorporates a novel oxidation enzyme (MtSAD1) which facilitates the conversion of eugenol to ferulic acid. It was discovered that the new process using this enzyme results in a different $\delta^{13}C$ value range than expected compared to that obtained using the fermentation based process based on the disclosure in Overhage et al (2003) which uses VaoA/CalA/CalB fermentation process.

SUMMARY

The successful adoption of a bioconversion process in *E. coli* offers a low cost and industrially economical process for vanillin production. The known bacterial CalA/CalB genes of *Pseudomonas* sp. HR199 were replaced with plant based genes (MtSAD1 and AtADH1) which successfully converted ferulic acid to natural vanillin with a molar yield of 90% to 96% within 24 hours of incubation. Ferulic acid (26 g/l) was recovered after about 60 hours of incubation with the novel recombinant *E. coli* microorganism comprising VaoA and the plant based genes (MtSAD1 and AtADH1) when this biotransformation was scaled up to 30 L fermentation volume in a 50 L bioreactor.

A biotransformation process for converting eugenol to ferulic acid and further conversion to vanillin in recombinant strains of *E. coli* is disclosed. The biotransformation process was successfully transferred to a 30 L scale where a ferulic acid concentration of 26 g/l after a total fermentation time of 64 hours was obtained. Based on this successful conversion, two different two step biotransformation process leading from eugenol to vanillin were established. The first two step biotransformation process uses a recombinant *E. coli* strain in the first step and a *Streptomyces/Amcolatopsis* strain in the second step to convert ferulic acid to natural vanillin. The second two step biotransformation process uses a recombinant *E. coli* strain in the first step and a different recombinant *E. coli* strain in the second step.

Using the first two step biotransformation process, Applicants' result showed a yield of 13.4 g/L vanillin was obtained from 21.6 g/L FA, corresponding to a molar yield of vanillin at 79.2%. The accumulation of vanillin is more or less linear over the fermentation period. However, a rapid FA reduction was observed at the first 24 hours, suggesting *S. viridosporus* converts ferulic acid into different intermediates before being converted to vanillin. Using the second two step biotransformation process, the sequential application of two recombinant *E. coli* strains harbouring the hybrid plasmids AmFCS-pCDFDuet and PfECH-pRSFDuet initially led to the production of 2.2 g/l after 24 hours from 3 g/l of ferulic acid which is a better yield than that obtained by Overhage et al (2003) where only a yield of 0.3 g/l of FA was obtained after two hours.

The present disclosure provides a fermentation based process which converts eugenol to vanillin that fits the regulatory requirements for a natural ingredient in the EU. The novel fermentation based process incorporates an oxidation enzyme (MtSAD1) which facilitates the conversion of eugenol to ferulic acid. It was discovered that the novel process results in ferulic acid/vanillin product with a different $\delta^{13}C$ value range when compared with the $\delta^{13}C$ value range obtained for ferulic acid/vanillin obtained from other plant sources selected from rice, maize, sugar beet, wheat and curcumin.

The invention claimed is:

1. A bioconversion method of making vanillin comprising:
    expressing a Vanillyl-alcohol oxidase (VaoA) gene product obtained from *Penicillum* species and
    a Saponin-deficient 1 (mtSAD1) gene product obtained from *Medicago* species expressed in a *Escherichia coli* (*E. coli*) host cell;
    feeding eugenol to the *E. coli* host cell; wherein
    the *E. coli* host cell converts ferulic acid to vanillin, thereby making vanillin.

2. The bioconversion method of making vanillin of claim 1, wherein the MtSAD1 gene product comprises an amino acid sequence selected from the group consisting of: SEQ ID No. 1; an amino acid sequence with at least 90% or at least 95% identity to SEQ ID No. 1; and an amino acid sequence expressed from *E. coli*.

3. The bioconversion method of making vanillin of claim 1, wherein the VaoA gene product comprises an amino acid sequence selected from the group consisting of: SEQ ID No. 5; an amino acid sequence with at or at least 90% or at least 95% identity to SEQ ID No. 5; and an amino acid sequence expressed from *E. coli*.

4. The bioconversion method of making vanillin of claim 1 further comprising expressing an Alcohol Dehydrogenase (ADH) gene product of SEQ ID No. 3.

5. The bioconversion method of making vanillin of claim 1, further comprising the step of purifying the VaoA, MtSAD1 and/or ADH gene product as a recombinant protein.

6. The bioconversion method of making vanillin of claim 1, wherein converting ferulic acid to vanillin further comprises incubating ferulic acid with a microorganism selected from the group consisting of *Pseudomonas* sp. HR 199, *Amycolatopsis* sp. ATCC 39116, *Amycolatopsis* sp. HR167, *Sphingomonas paucimobilis* SYK-6, *Pseudomonas fluorescens* AN103, *Streptomyces setonii*, *Streptomyces sannanensis*, *Amycolatopsis* sp. strain (Zhp06) and a combination thereof.

7. A composition comprising vanillin obtained by the method of claim 1, wherein the vanillin has a $\delta^{13}C$ value range of −25 to −32 that differs from the $\delta^{13}C$ value range of vanillin obtained in other plant sources selected from the group consisting of rice, maize, sugar beet, wheat and curcumin; and wherein the value range differs from vanillin obtained from lignin and guaiacol.

8. A method of flavoring a consumable product, the method comprising: the vanillian prepared by the method of claim 1, wherein the vanillin is admixed with the consumable product.

9. The method of claim 8, wherein the consumable product is selected from the group consisting of a food product, a pharmaceutical composition, a dietary supplement, a nutraceutical, and a cosmetic product.

* * * * *

SEQUENCE LISTING

<160> NUMBER OF SEQ ID NOS: 22

<210> SEQ ID NO 1
<211> LENGTH: 269
<212> TYPE: PRT
<213> ORGANISM: Medicago truncatula

<400> SEQUENCE: 1

Met Ala Glu Ala Ser Ser Thr Asn Ser Gly Leu Arg Leu Ala Gly Lys
1               5                   10                  15

Val Ala Ile Val Thr Gly Gly Ala Ser Gly Ile Gly Lys Glu Thr Ala
            20                  25                  30

His Leu Phe Ala Glu Gln Gly Ala Arg Met Val Val Ile Ala Asp Ile
        35                  40                  45

Gln Asp Glu Leu Gly Asn Gln Val Ala Ala Ser Ile Gly Ser Arg Lys
    50                  55                  60

Cys Thr Tyr Ile His Cys Asp Ile Ala Asn Glu Asp Gln Val Lys Asn
65                  70                  75                  80

Leu Val Gln Ser Thr Val Asn Ala Tyr Gly Gln Ile Asp Ile Met Phe
                85                  90                  95

Ser Asn Ala Gly Ile Ala Ser Pro Ser Asp Gln Thr Ile Leu Glu Leu
            100                 105                 110

Asp Ile Ser Gln Ala Asp His Val Phe Ala Val Asn Ile Arg Gly Thr
        115                 120                 125

Thr Leu Cys Val Lys Tyr Ala Ala Arg Ala Met Val Glu Gly Arg Val
130                 135                 140

Arg Gly Ser Ile Val Cys Thr Ala Ser Val Leu Gly Ser Gln Gly Val
145                 150                 155                 160

Leu Arg Leu Thr Asp Tyr Thr Ile Ser Lys His Ala Ile Ile Gly Leu
                165                 170                 175

Met Arg Ser Ala Ser Val Gln Leu Ala Lys Tyr Gly Ile Arg Val Asn
            180                 185                 190

Cys Val Ser Pro Asn Gly Leu Ala Thr Pro Leu Thr Met Lys Leu Leu
        195                 200                 205

Gly Ala Ser Ala Lys Thr Val Glu Leu Ile Tyr Glu Gln Asn Lys Arg
    210                 215                 220

Leu Glu Gly Val Val Leu Asn Thr Lys His Val Ala Asp Ala Val Leu
225                 230                 235                 240

Phe Leu Val Ser Asn Glu Ser Asp Phe Val Thr Gly Leu Asp Leu Arg
                245                 250                 255

Val Asp Gly Ser Tyr Val Tyr Gly Lys Tyr Glu Leu Leu
            260                 265

<210> SEQ ID NO 2
<211> LENGTH: 810
<212> TYPE: DNA
<213> ORGANISM: Medicago truncatula

<400> SEQUENCE: 2
atggcagaag catcatccac taacagcggt cttaggttag ccggcaaagt agccatcgtc      60
accggaggtg ccagcggcat tggcaaagag acggcacatc tctttgccga acaaggtgca     120
cgcatggtgg tgattgccga catccaagac gagttgggca atcaagtggc tgcatccatt     180
ggcagtcgca agtgcaccta cattcattgt gatatagcaa atgaagatca agttaaaaat     240
ctcgttcaat caactgtcaa tgcttatgga cagatagata ttatgtttag caatgctggg     300
attgcaagtc catctgatca gactattttg gaactcgaca tttctcaagc cgaccatgtg     360
tttgcagtta acattcgagg aacgacattg tgtgtgaaat acgcggcacg tgcgatggtg     420
gaggggcgcg tgaggggtag cattgtgtgc acagcgagcg tattgggtag ccaaggtgtc     480
ttgaggttaa ccgattacac aatatcgaag catgcaataa tagggttgat gcgctcagcg     540

-continued

```
agtgtgcaac ttgcaaaata cgggataaga gtgaattgtg tctcgccaaa tggattagca      600
acaccattga ctatgaaatt gttaggggca agtgctaaga cagtcgagtt gatttatgaa      660
caaaacaaga ggttggaagg agtggttctc aacactaaac atgttgcaga tgctgtgttg      720
ttcttggtat ctaatgaatc tgactttgtc actggccttg atcttcgtgt ggatggcagc      780
tatgtttatg gcaaatatga actattataa                                      810
```

```
<210> SEQ ID NO 3
<211> LENGTH: 501
<212> TYPE: PRT
<213> ORGANISM: Arabidopsis thaliana

<400> SEQUENCE: 3
```

| | | | | | | | | | | | | | | |
|---|---|---|---|---|---|---|---|---|---|---|---|---|---|---|
| Met | Glu | Asn | Gly | Lys | Cys | Asn | Gly | Ala | Thr | Thr | Val | Lys | Leu | Pro | Glu |
| 1 | | | | 5 | | | | | 10 | | | | | 15 | |

Met Glu Asn Gly Lys Cys Asn Gly Ala Thr Thr Val Lys Leu Pro Glu
1               5                   10                  15

Ile Lys Phe Thr Lys Leu Phe Ile Asn Gly Gln Phe Ile Asp Ala Ala
                20                  25                  30

Ser Gly Lys Thr Phe Glu Thr Ile Asp Pro Arg Asn Gly Glu Val Ile
            35                  40                  45

Ala Thr Ile Ala Glu Gly Asp Lys Glu Asp Val Asp Leu Ala Val Asn
50                  55                  60

Ala Ala Arg Tyr Ala Phe Asp His Gly Pro Trp Pro Arg Met Thr Gly
65                  70                  75                  80

Phe Glu Arg Ala Lys Leu Ile Asn Lys Phe Ala Asp Leu Ile Glu Glu
                85                  90                  95

Asn Ile Glu Glu Leu Ala Lys Leu Asp Ala Val Asp Gly Gly Lys Leu
            100                 105                 110

Phe Gln Leu Gly Lys Tyr Ala Asp Ile Pro Ala Thr Ala Gly His Phe
        115                 120                 125

Arg Tyr Asn Ala Gly Ala Ala Asp Lys Ile His Gly Glu Thr Leu Lys
130                 135                 140

Met Thr Arg Gln Ser Leu Phe Gly Tyr Thr Leu Lys Glu Pro Ile Gly
145                 150                 155                 160

Val Val Gly Asn Ile Ile Pro Trp Asn Phe Pro Ser Ile Met Phe Ala
                165                 170                 175

Thr Lys Val Ala Pro Ala Met Ala Ala Gly Cys Thr Met Val Val Lys
            180                 185                 190

Pro Ala Glu Gln Thr Ser Leu Ser Ala Leu Phe Tyr Ala His Leu Ser
        195                 200                 205

Lys Glu Ala Gly Ile Pro Asp Gly Val Leu Asn Ile Val Thr Gly Phe
210                 215                 220

Gly Ser Thr Ala Gly Ala Ala Ile Ala Ser His Met Asp Val Asp Lys
225                 230                 235                 240

Val Ser Phe Thr Gly Ser Thr Asp Val Gly Arg Lys Ile Met Gln Ala
                245                 250                 255

Ala Ala Ala Ser Asn Leu Lys Lys Val Ser Leu Glu Leu Gly Gly Lys
            260                 265                 270

Ser Pro Leu Leu Ile Phe Asn Asp Ala Asp Ile Asp Lys Ala Ala Asp
        275                 280                 285

Leu Ala Leu Leu Gly Cys Phe Tyr Asn Lys Gly Glu Ile Cys Val Ala
290                 295                 300

Ser Ser Arg Val Phe Val Gln Glu Gly Ile Tyr Asp Lys Val Val Glu
305                 310                 315                 320

Lys Leu Val Glu Lys Ala Lys Asp Trp Thr Val Gly Asp Pro Phe Asp
            325                 330                 335

Ser Thr Ala Arg Gln Gly Pro Gln Val Asp Lys Arg Gln Phe Glu Lys
            340                 345                 350

Ile Leu Ser Tyr Ile Glu His Gly Lys Asn Glu Gly Ala Thr Leu Leu
            355                 360                 365

Thr Gly Gly Lys Ala Ile Gly Asp Lys Gly Tyr Phe Ile Gln Pro Thr
        370                 375                 380

Ile Phe Ala Asp Val Thr Glu Asp Met Lys Ile Tyr Gln Asp Glu Ile
385                 390                 395                 400

Phe Gly Pro Val Met Ser Leu Met Lys Phe Lys Thr Val Glu Glu Gly
                405                 410                 415

Ile Lys Cys Ala Asn Asn Thr Lys Tyr Gly Leu Ala Ala Gly Ile Leu
            420                 425                 430

Ser Gln Asp Ile Asp Leu Ile Asn Thr Val Ser Arg Ser Ile Lys Ala
            435                 440                 445

Gly Ile Ile Trp Val Asn Cys Tyr Phe Gly Phe Asp Leu Asp Cys Pro
        450                 455                 460

Tyr Gly Gly Tyr Lys Met Ser Gly Asn Cys Arg Glu Ser Gly Met Asp
465                 470                 475                 480

Ala Leu Asp Asn Tyr Leu Gln Thr Lys Ser Val Val Met Pro Leu His
                485                 490                 495

Asn Ser Pro Trp Met
            500

<210> SEQ ID NO 4
<211> LENGTH: 1506
<212> TYPE: DNA
<213> ORGANISM: Arabidopsis thaliana

<400> SEQUENCE: 4

```
atggagaacg gcaaatgcaa cggagccacg acggtgaagt taccggagat caaattcacc        60
aagcttttca tcaacggcca gttcattgat gctgcttcag ggaagacgtt tgagacgata       120
gaccctagga acggtgaagt gatcgcaaca atagccgaag agacaaagaa agacgttgac       180
ttggccgtta acgctgcacg ttacgccttc gaccatggtc cttggcctcg catgaccggc       240
ttcgagaggg caaagcttat caacaaattc gcagacttaa tagaggaaaa cattgaggaa       300
ttggctaaac ttgatgcggt tgacggtgga aaattgtttc agttgggaaa atatgctgat       360
attccggcca cagccggtca ttttcgatac aatgcgggtg cagcagataa aatccacggc       420
gagactctta aaatgacgcg tcaatctttg ttcggataca ccctcaaaga accaattgga       480
gtggttggta atatcatccc ttggaatttc ccaagcatta tgtttgccac aaaggtggct       540
ccggctatgg ctgctggttg caccatggtg gtcaagccag ctgaacagac ttcactctct       600
gctttgttct atgcccatct ctcaaaagaa gcgggaattc ctgatggtgt gctcaacatt       660
gtaactggtt ttggatcaac tgctggagct gccattgcct cccatatgga cgtagacaaa       720
gttagtttca ctgggtcaac agatgttgga aggaagataa tgcaagccgc agccgcaagt       780
aatctcaaaa agtttccct tgaattaggc gggaaatcgc cacttctcat attcaacgac       840
gctgatattg acaaagccgc cgatcttgcg cttctcggtt gcttttacaa caagggtgaa       900
atttgcgtgg cgagctctcg tgtgtttgtt caagaaggta tatacgataa ggttgtggag       960
aagttagtag agaaggctaa agattggacc gttggtgatc cttttgattc cactgctcga      1020
caaggaccctc aagtggataa aagacagttt gagaagattc tatcttacat tgagcacggt      1080
```

```
aaaaacgaag gagcgacctt attaactgga ggaaaagcca ttggagacaa aggatatttc    1140
atccaaccaa ctatattcgc agatgtcact gaggatatga agatataccaa agatgaaatc    1200 tttggaccag tcatgtcact gatgaaattc aagacggtag aggaagggat caaatgcgca    1260
aacaacacga atacggtct tgcagcagga atactaagcc aagacataga cttgatcaac    1320
acggtttcga ggtcaatcaa agctggaatc atttgggtta attgctactt cgggtttgat    1380
cttgactgtc cttatggtgg ctacaagatg agtggtaatt gtcgtgaaag tggcatggac    1440
gctctcgaca actatctaca aaccaaatcc gtcgttatgc ctcttcacaa ttccccttgg    1500
atgtaa                                                                1506
```

<210> SEQ ID NO 5
<211> LENGTH: 560
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Met Ser Lys Thr Gln Glu Phe Arg Pro Leu Thr Leu Pro Pro Lys Leu
1               5                   10                  15

Ser Leu Ser Asp Phe Asn Glu Phe Ile Gln Asp Ile Ile Arg Ile Val
            20                  25                  30

Gly Ser Glu Asn Val Glu Val Ile Ser Ser Lys Asp Gln Ile Val Asp
        35                  40                  45

Gly Ser Tyr Met Lys Pro Thr His Thr His Asp Pro His His Val Met
    50                  55                  60

Asp Gln Asp Tyr Phe Leu Ala Ser Ala Ile Val Ala Pro Arg Asn Val
65                  70                  75                  80

Ala Asp Val Gln Ser Ile Val Gly Leu Ala Asn Lys Phe Ser Phe Pro
                85                  90                  95

Leu Trp Pro Ile Ser Ile Gly Arg Asn Ser Gly Tyr Gly Gly Ala Ala
            100                 105                 110

Pro Arg Val Ser Gly Ser Val Val Leu Asp Met Gly Lys Asn Met Asn
        115                 120                 125

Arg Val Leu Glu Val Asn Val Glu Gly Ala Tyr Cys Val Val Glu Pro
    130                 135                 140

Gly Val Thr Tyr His Asp Leu His Asn Tyr Leu Glu Ala Asn Asn Leu
145                 150                 155                 160

Arg Asp Lys Leu Trp Leu Asp Val Pro Asp Leu Gly Gly Gly Ser Val
                165                 170                 175

Leu Gly Asn Ala Val Glu Arg Gly Val Gly Tyr Thr Pro Tyr Gly Asp
            180                 185                 190

His Trp Met Met His Ser Gly Met Glu Val Val Leu Ala Asn Gly Glu
        195                 200                 205

Leu Leu Arg Thr Gly Met Gly Ala Leu Pro Asp Pro Lys Arg Pro Glu
    210                 215                 220

Thr Met Gly Leu Lys Pro Glu Asp Gln Pro Trp Ser Lys Ile Ala His
225                 230                 235                 240

Leu Phe Pro Tyr Gly Phe Gly Pro Tyr Ile Asp Gly Leu Phe Ser Gln
                245                 250                 255

Ser Asn Met Gly Ile Val Thr Lys Ile Gly Ile Trp Leu Met Pro Asn
            260                 265                 270
```

```
Pro Gly Gly Tyr Gln Ser Tyr Leu Ile Thr Leu Pro Lys Asp Gly Asp
            275                 280                 285

Leu Lys Gln Ala Val Asp Ile Ile Arg Pro Leu Arg Leu Gly Met Ala
    290                 295                 300

Leu Gln Asn Val Pro Thr Ile Arg His Ile Leu Leu Asp Ala Ala Val
305                 310                 315                 320

Leu Gly Asp Lys Arg Ser Tyr Ser Ser Lys Thr Glu Pro Leu Ser Asp
            325                 330                 335

Glu Glu Leu Asp Lys Ile Ala Lys Gln Leu Asn Leu Gly Arg Trp Asn
            340                 345                 350

Phe Tyr Gly Ala Leu Tyr Gly Pro Glu Pro Ile Arg Arg Val Leu Trp
    355                 360                 365

Glu Thr Ile Lys Asp Ala Phe Ser Ala Ile Pro Gly Val Lys Phe Tyr
    370                 375                 380

Phe Pro Glu Asp Thr Pro Glu Asn Ser Val Leu Arg Val Arg Asp Lys
385                 390                 395                 400

Thr Met Gln Gly Ile Pro Thr Tyr Asp Glu Leu Lys Trp Ile Asp Trp
            405                 410                 415

Leu Pro Asn Gly Ala His Leu Phe Phe Ser Pro Ile Ala Lys Val Ser
            420                 425                 430

Gly Glu Asp Ala Met Met Gln Tyr Ala Val Thr Lys Lys Arg Cys Gln
            435                 440                 445

Glu Ala Gly Leu Asp Phe Ile Gly Thr Phe Thr Val Gly Met Arg Glu
    450                 455                 460

Met His His Ile Val Cys Ile Val Phe Asn Lys Lys Asp Leu Ile Gln
465                 470                 475                 480

Lys Arg Lys Val Gln Trp Leu Met Arg Thr Leu Ile Asp Asp Cys Ala
            485                 490                 495

Ala Asn Gly Trp Gly Glu Tyr Arg Thr His Leu Ala Phe Met Asp Gln
            500                 505                 510

Ile Met Glu Thr Tyr Asn Trp Asn Asn Ser Ser Phe Leu Arg Phe Asn
    515                 520                 525

Glu Val Leu Lys Asn Ala Val Asp Pro Asn Gly Ile Ile Ala Pro Gly
530                 535                 540

Lys Ser Gly Val Trp Pro Ser Gln Tyr Ser His Val Thr Trp Lys Leu
545                 550                 555                 560
```

<210> SEQ ID NO 6
<211> LENGTH: 1683
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
atgagtaaaa cccaagaatt tcgtccgctg accttacctc gaaattaag cctgtcagat      60 tttaacgaat ttatacaaga catcataagg atagtgggta gcgagaacgt agaggttatc    120
agtagcaaag atcaaatcgt ggatggcagc tacatgaagc cgacccatac ccatgacccg    180
caccacgtta tggatcaaga ttattttctg gcaagcgcta tcgtcgcacc gcgtaacgtt    240
gcagacgttc aaagcattgt tggtctggca aacaaattca gcttcccgct gtggccgatt    300
agcatcggtc gtaacagcgg ttacggtgga gcagcaccgc gtgttagcgg tagcgttgtt    360
ctcgatatgg gcaaaaacat gaatcgtgtt ctggaagtta atgtggaagg tgcctattgt    420

| | |
|---|---|
| gttgttgaac cgggtgttac ctatcatgat ctgcataatt atctggaagc caataacctg | 480 |
| cgtgataagc tgtggctgga cgttccagac ctgggtggtg gcagcgtact gggtaacgca | 540 |
| gtagaacgtg gagttggtta caccccgtat ggtgaccact ggatgatgca tagcggtatg | 600 |
| gaggttgtgc tggcaaacgg tgagctgctg cgtaccggta tgggtgcact gccagacccg | 660 |
| aagcgaccgg agacaatggg tctgaagccg gaggatcaac cgtggtcaaa gattgcacac | 720 |
| ctgtttccgt atggttttgg tccgtatatt gatggtctgt ttagtcagag caacatgggt | 780 |
| attgttacca aaattggcat ttggctgatg ccgaatccgg gtggttatca gagctatctg | 840 |
| attaccctgc cgaaagatgg tgatctgaaa caggcagttg atattatccg tccgctgcgt | 900 |
| ctgggtatgg cactgcagaa tgttccgacc attcgtcata ttctgctgga tgccgcagtt | 960 |
| ctgggtgata acgtagcta tagcagtaaa accgaaccgc tgagtgatga agaactggat | 1020 |
| aaaattgcaa acagctgaa tctgggtcgc tggaactttt atggtgcact gtatggtccg | 1080 |
| gaaccgattc gtcgtgtgct gtgggaaacc attaagatg catttagcgc aattccgggt | 1140 |
| gtgaaattct attttccgga agatacaccg gaaaattcag ttctgcgtgt tcgtgataaa | 1200 |
| accatgcagg gtattccgac ctatgatgaa ctgaaatgga ttgattggct gccgaatggt | 1260 |
| gcccacctct tttttagccc gatagcaaaa gttagcggag aggacgcgat gatgcagtat | 1320 |
| gcagtgacca aaaaacgttg tcaagaagca ggtctggatt ttattggcac ctttaccgtt | 1380 |
| ggtatgcgta aaatgcatca tattgtgtgc atcgtgttta acaaaaaaga cctgattcag | 1440 |
| aaacgcaagg ttcaatggct tatgcgtaca ctgatagacg attgcgcagc taacggttgg | 1500 |
| ggtgagtacc gtacacacct agcatttatg gatcagatca tggagacgta taattggaat | 1560 |
| aacagcagct ttctgcgctt taatgaagtt ctgaaaaatg ccgttgatcc gaatggtatt | 1620 |
| atcgcaccgg gtaaaagcgg cgtatggcct agccagtata gccacgtaac ctggaagcta | 1680 |
| taa | 1683 |

<210> SEQ ID NO 7
<211> LENGTH: 1476
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

| | |
|---|---|
| atgcgtaatc agggtctggg tagctggccg gttcgtcgtg ctcgtatgtc cccgcatgca | 60 |
| acggctgttc gtcacggtgg tacggcgctg acctatgccg aactgagtcg tcgtgtggca | 120 |
| cgtctggcaa acggtctgcg tgcagcaggt gtgcgtccgg gtgatcgcgt tgcgtatctg | 180 |
| ggtccgaatc atccggccta cctggaaacc ctgtttgcat gcggccaggc cggtgcagtt | 240 |
| tttgtcccgc tgaacttccg tctgggcgtt ccggaactgg atcacgctct ggcggactca | 300 |
| ggtgcctcgg tgctgattca tacccccgaa cacgcagaaa cggttgcagc tctggcagca | 360 |
| ggtcgtctgc tgcgcgtccc ggcaggtgaa ctggatgcag ctgatgacga accgccggac | 420 |
| ctgccggttg gtctggatga cgtctgcctg ctgatgtata ccagtggctc cacgggtcgt | 480 |
| ccgaaaggcg cgatgctgac ccacggcaat ctgacgtgga actgtgtgaa tgttctggtc | 540 |
| gaaaccgatc tggccagcga cgaacgtgca ctggtggcag caccgctgtt tcatgcagct | 600 |
| gcgctgggta tggtgtgcct gccgaccctg ctgaaaggcg gtacggttat tctgcacagt | 660 |
| gcgtttgatc cgggcgctgt gctgtccgcg gttgaacagg aacgtgtcac cctggtgttc | 720 |

```
ggtgttccga cgatgtacca agctatcgca gcacatccgc gttggcgtag cgcagatctg    780
agctctctgc gcaccctgct gtgtggtggt gcaccggtgc cggctgatct ggcgtctcgt    840
tatctggacc gcggcctggc gttcgttcaa ggctacggta tgaccgaagc tgcgccgggt    900
gtgctggttc tggatcgtgc ccacgtggca gaaaaaattg gcagcgcggg tgtcccgagc    960
tttttcacgg atgttcgtct ggcaggtccg tcaggtgaac cggttccgcc gggcgaaaaa   1020
ggtgaaatcg tggtttcggg cccgaacgtg atgaaaggct attggggtcg tccggaagcc   1080
accgcagaag ttctgcgcga tggctggttt cattctggtg acgtcgccac ggtggatggc   1140
gacggttatt ccacgtcgt ggatcgtctg aaagacatga ttatcagcgg cggtgaaaac   1200
```

```
ggtgttccga cgatgtacca agctatcgca gcacatccgc gttggcgtag cgcagatctg    780
agctctctgc gcaccctgct gtgtggtggt gcaccggtgc cggctgatct ggcgtctcgt    840
tatctggacc gcggcctggc gttcgttcaa ggctacggta tgaccgaagc tgcgccgggt    900
gtgctggttc tggatcgtgc ccacgtggca gaaaaaattg gcagcgcggg tgtcccgagc    960
tttttcacgg atgttcgtct ggcaggtccg tcaggtgaac cggttccgcc gggcgaaaaa   1020
ggtgaaatcg tggtttcggg cccgaacgtg atgaaaggct attggggtcg tccggaagcc   1080
accgcagaag ttctgcgcga tggctggttt cattctggtg acgtcgccac ggtggatggc   1140
gacggttatt ccacgtcgt ggatcgtctg aaagacatga ttatcagcgg cggtgaaaac   1200
atttacccgg cggaagttga aaatgaactg tatggctacc cgggtgtcga agcttgtgcg   1260
gttatcggcg tgccggaccc gcgttggggt gaagtgggta agctgttgt cgtgccggca   1320
gacggcagtc gcatcgatgg tgacgaactg ctggcttggc tgcgtacccg tctggcaggt   1380
tacaaagtcc cgaaatccgt ggaattcacg gatcgcctgc cgaccacggg ctccggtaaa   1440
atcctgaaag gcgaagtgcg tcgtcgtttt ggctaa                             1476
```

<210> SEQ ID NO 8
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Met Arg Asn Gln Gly Leu Gly Ser Trp Pro Val Arg Ala Arg Met
1               5                   10                  15

Ser Pro His Ala Thr Ala Val Arg His Gly Gly Thr Ala Leu Thr Tyr
            20                  25                  30

Ala Glu Leu Ser Arg Arg Val Ala Arg Leu Ala Asn Gly Leu Arg Ala
        35                  40                  45

Ala Gly Val Arg Pro Gly Asp Arg Val Ala Tyr Leu Gly Pro Asn His
    50                  55                  60

Pro Ala Tyr Leu Glu Thr Leu Phe Ala Cys Gly Gln Ala Gly Ala Val
65                  70                  75                  80

Phe Val Pro Leu Asn Phe Arg Leu Gly Val Pro Glu Leu Asp His Ala
                85                  90                  95

Leu Ala Asp Ser Gly Ala Ser Val Leu Ile His Thr Pro Glu His Ala
            100                 105                 110

Glu Thr Val Ala Ala Leu Ala Ala Gly Arg Leu Leu Arg Val Pro Ala
        115                 120                 125

Gly Glu Leu Asp Ala Ala Asp Asp Glu Pro Pro Asp Leu Pro Val Gly
    130                 135                 140

Leu Asp Asp Val Cys Leu Leu Met Tyr Thr Ser Gly Ser Thr Gly Arg
145                 150                 155                 160

Pro Lys Gly Ala Met Leu Thr His Gly Asn Leu Thr Trp Asn Cys Val
                165                 170                 175

Asn Val Leu Val Glu Thr Asp Leu Ala Ser Asp Glu Arg Ala Leu Val
            180                 185                 190

Ala Ala Pro Leu Phe His Ala Ala Leu Gly Met Val Cys Leu Pro
        195                 200                 205

Thr Leu Leu Lys Gly Gly Thr Val Ile Leu His Ser Ala Phe Asp Pro
    210                 215                 220

Gly Ala Val Leu Ser Ala Val Glu Gln Glu Arg Val Thr Leu Val Phe
225                 230                 235                 240

Gly Val Pro Thr Met Tyr Gln Ala Ile Ala Ala His Pro Arg Trp Arg
            245                 250                 255

Ser Ala Asp Leu Ser Ser Leu Arg Thr Leu Leu Cys Gly Gly Ala Pro
        260                 265                 270

Val Pro Ala Asp Leu Ala Ser Arg Tyr Leu Asp Arg Gly Leu Ala Phe
    275                 280                 285

Val Gln Gly Tyr Gly Met Thr Glu Ala Ala Pro Gly Val Leu Val Leu
290                 295                 300

Asp Arg Ala His Val Ala Glu Lys Ile Gly Ser Ala Gly Val Pro Ser
305                 310                 315                 320

Phe Phe Thr Asp Val Arg Leu Ala Gly Pro Ser Gly Glu Pro Val Pro
            325                 330                 335

Pro Gly Glu Lys Gly Glu Ile Val Val Ser Gly Pro Asn Val Met Lys
        340                 345                 350

Gly Tyr Trp Gly Arg Pro Glu Ala Thr Ala Glu Val Leu Arg Asp Gly
    355                 360                 365

Trp Phe His Ser Gly Asp Val Ala Thr Val Asp Gly Asp Gly Tyr Phe
370                 375                 380

His Val Val Asp Arg Leu Lys Asp Met Ile Ile Ser Gly Gly Glu Asn
385                 390                 395                 400

Ile Tyr Pro Ala Glu Val Glu Asn Glu Leu Tyr Gly Tyr Pro Gly Val
            405                 410                 415

Glu Ala Cys Ala Val Ile Gly Val Pro Asp Pro Arg Trp Gly Glu Val
        420                 425                 430

Gly Lys Ala Val Val Pro Ala Asp Gly Ser Arg Ile Asp Gly Asp
    435                 440                 445

Glu Leu Leu Ala Trp Leu Arg Thr Arg Leu Ala Gly Tyr Lys Val Pro
450                 455                 460

Lys Ser Val Glu Phe Thr Asp Arg Leu Pro Thr Thr Gly Ser Gly Lys
465                 470                 475                 480

Ile Leu Lys Gly Glu Val Arg Arg Arg Phe Gly
            485                 490

<210> SEQ ID NO 9
<211> LENGTH: 831
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atgagcacat acgaaggtcg ctggaaaacg gtcaaggtcg aaatcgaaga cggcatcgcg     60
tttgtcatcc tcaatcgccc ggaaaaacgc aacgcgatga gcccgaccct gaaccgcgag    120
atgatcgatg ttctggaaac cctggagcag gaccctgccg ccggtgtgct ggtgctgacc    180
ggtgcgggcg aagcctggac cgcaggcatg gacctcaagg aatacttccg cgaagtggac    240
gccggcccgg aaatcctcca ggaaaaaatc gccgcgaagc ctcgcaatg caatggaaa     300 ctgctgcgca tgtacgccaa gccgaccatc gcgatggtca atggctggtg cttcggcggc    360
ggtttcagcc cgctggtggc ctgcgacctg gcgatctgcg ccgacgaagc aaccttcggt    420
ctctcggaaa tcaactgggg tatcccgccg ggcaacctgg tgagcaaggc gatggccgac    480

```
accgtgggcc accgccagtc gctctactac atcatgaccg gcaagacctt cggtgggcag      540
aaagccgccg agatgggcct ggtcaacgaa agcgtgcccc tggcgcaact gcgcgaagtc      600
accatcgagc tggcgcgtaa cctgctcgaa aaaacccgg tggtgctgcg tgccgccaaa       660
cacggtttca acgctgccg cgaactgacc tgggagcaga acgaggatta cctgtacgcc       720
aagctcgatc agtcgcgttt gctggacacc gaaggcggtc gcgagcaggg catgaagcaa      780
ttcctcgacg acaagagcat caagcctggc ctgcaagcgt ataaacgctg a               831
```

<210> SEQ ID NO 10
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Met Ser Thr Tyr Glu Gly Arg Trp Lys Thr Val Lys Val Glu Ile Glu
1               5                   10                  15

Asp Gly Ile Ala Phe Val Ile Leu Asn Arg Pro Glu Lys Arg Asn Ala
            20                  25                  30

Met Ser Pro Thr Leu Asn Arg Glu Met Ile Asp Val Leu Glu Thr Leu
        35                  40                  45

Glu Gln Asp Pro Ala Ala Gly Val Leu Val Leu Thr Gly Ala Gly Glu
    50                  55                  60

Ala Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Glu Ala Ser Gln
                85                  90                  95

Trp Gln Trp Lys Leu Leu Arg Met Tyr Ala Lys Pro Thr Ile Ala Met
            100                 105                 110

Val Asn Gly Trp Cys Phe Gly Gly Gly Phe Ser Pro Leu Val Ala Cys
        115                 120                 125

Asp Leu Ala Ile Cys Ala Asp Glu Ala Thr Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Gln Lys Ala Ala Glu Met Gly Leu Val Asn Glu Ser Val
            180                 185                 190

Pro Leu Ala Gln Leu Arg Glu Val Thr Ile Glu Leu Ala Arg Asn Leu
        195                 200                 205

Leu Glu Lys Asn Pro Val Val Leu Arg Ala Ala Lys His Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Gly Arg Glu Gln
                245                 250                 255

Gly Met Lys Gln Phe Leu Asp Asp Lys Ser Ile Lys Pro Gly Leu Gln
            260                 265                 270

Ala Tyr Lys Arg
        275
```

-continued

```
<210> SEQ ID NO 11
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ggaattccat atggcagaag catcatccac taacagc                                37

<210> SEQ ID NO 12
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ccgctcgagt tataatagtt catatttgcc ataaac                                 36

<210> SEQ ID NO 13
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
gaagatctgg agaacggcaa atgcaacgga g                                     31

<210> SEQ ID NO 14
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
ccgctcgagt tacatccaag gggaattgtg aagag                                 35

<210> SEQ ID NO 15
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
ggaattccat atgagtaaaa cccaagaatt tcgtc                                 35

<210> SEQ ID NO 16
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 16
ccgctcgagt tatagcttcc aggttacgtg gc                                    32

<210> SEQ ID NO 17
<211> LENGTH: 269
<212> TYPE: PRT
<213> ORGANISM: Medicago truncatula

<400> SEQUENCE: 17

Met Ala Glu Ala Ser Ser Thr Asn Ser Gly Leu Arg Leu Ala Gly Lys
1               5                   10                  15

Val Ala Ile Val Thr Gly Gly Ala Ser Gly Ile Gly Lys Glu Thr Ala
            20                  25                  30

His Leu Phe Ala Glu Gln Gly Ala Arg Met Val Val Ile Ala Asp Ile
        35                  40                  45

Gln Asp Glu Leu Gly Asn Gln Val Ala Ala Ser Ile Gly Ser Arg Lys
    50                  55                  60

Cys Thr Tyr Ile His Cys Asp Ile Ala Asn Glu Asp Gln Val Lys Asn
65                  70                  75                  80

Leu Val Gln Ser Thr Val Asn Ala Tyr Gly Gln Ile Asp Ile Met Phe
                85                  90                  95

Ser Asn Ala Gly Ile Ala Ser Pro Ser Asp Gln Thr Ile Leu Glu Leu
            100                 105                 110

Asp Ile Ser Gln Ala Asp His Val Phe Ala Val Asn Ile Arg Gly Thr
        115                 120                 125

Thr Leu Cys Val Lys Tyr Ala Ala Arg Ala Met Val Glu Gly Arg Val
    130                 135                 140

Arg Gly Ser Ile Val Cys Thr Ala Ser Val Leu Gly Ser Gln Gly Val
145                 150                 155                 160

Leu Arg Leu Thr Asp Tyr Thr Ile Ser Lys His Ala Ile Ile Gly Leu
                165                 170                 175

Met Arg Ser Ala Ser Val Gln Leu Ala Lys Tyr Gly Ile Arg Val Asn
            180                 185                 190

Cys Val Ser Pro Asn Gly Leu Ala Thr Pro Leu Thr Met Lys Leu Leu
        195                 200                 205

Gly Ala Ser Ala Lys Thr Val Glu Leu Ile Tyr Glu Gln Asn Lys Arg
    210                 215                 220

Leu Glu Gly Val Val Leu Asn Thr Lys His Val Ala Asp Ala Val Leu
225                 230                 235                 240

Phe Leu Val Ser Asn Glu Ser Asp Phe Val Thr Gly Leu Asp Leu Arg
                245                 250                 255

Val Asp Gly Ser Tyr Val Tyr Gly Lys Tyr Glu Leu Leu
            260                 265

<210> SEQ ID NO 18
<211> LENGTH: 810
<212> TYPE: DNA
<213> ORGANISM: Medicago truncatula

<400> SEQUENCE: 18
atggcagaag catcatccac taacagcggt cttaggttag ccggcaaagt agccatcgtc      60
accggaggtg ccagcggcat tggcaaagag acggcacatc tctttgccga acaaggtgca     120
cgcatggtgg tgattgccga catccaagac gagttgggca atcaagtggc tgcatccatt     180
ggcagtcgca agtgcaccta cattcattgt gatatagcaa atgaagatca agttaaaaat     240

```
ctcgttcaat caactgtcaa tgcttatgga cagatagata ttatgtttag caatgctggg      300
attgcaagtc catctgatca gactattttg gaactcgaca tttctcaagc cgaccatgtg      360
tttgcagtta acattcgagg aacgacattg tgtgtgaaat acgcggcacg tgcgatggtg      420 gagggggcgcg tgaggggtag cattgtgtgc acagcgagcg tattgggtag ccaaggtgtc     480
ttgaggttaa ccgattacac aatatcgaag catgcaataa tagggttgat gcgctcagcg      540
agtgtgcaac ttgcaaaata cgggataaga gtgaattgtg tctcgccaaa tggattagca     600
acaccattga ctatgaaatt gttaggggca agtgctaaga cagtcgagtt gatttatgaa      660
caaaacaaga ggttggaagg agtggttctc aacactaaac atgttgcaga tgctgtgttg      720
ttcttggtat ctaatgaatc tgactttgtc actggccttg atcttcgtgt ggatggcagc      780
tatgtttatg gcaaatatga actattataa                                      810
```

<210> SEQ ID NO 19
<211> LENGTH: 501
<212> TYPE: PRT
<213> ORGANISM: Arabidopsis thaliana

<400> SEQUENCE: 19

```
Met Glu Asn Gly Lys Cys Asn Gly Ala Thr Thr Val Lys Leu Pro Glu
1               5                   10                  15

Ile Lys Phe Thr Lys Leu Phe Ile Asn Gly Gln Phe Ile Asp Ala Ala
            20                  25                  30

Ser Gly Lys Thr Phe Glu Thr Ile Asp Pro Arg Asn Gly Glu Val Ile
        35                  40                  45

Ala Thr Ile Ala Glu Gly Asp Lys Glu Asp Val Asp Leu Ala Val Asn
    50                  55                  60

Ala Ala Arg Tyr Ala Phe Asp His Gly Pro Trp Pro Arg Met Thr Gly
65                  70                  75                  80

Phe Glu Arg Ala Lys Leu Ile Asn Lys Phe Ala Asp Leu Ile Glu Glu
                85                  90                  95

Asn Ile Glu Glu Leu Ala Lys Leu Asp Ala Val Asp Gly Gly Lys Leu
            100                 105                 110

Phe Gln Leu Gly Lys Tyr Ala Asp Ile Pro Ala Thr Ala Gly His Phe
        115                 120                 125

Arg Tyr Asn Ala Gly Ala Ala Asp Lys Ile His Gly Glu Thr Leu Lys
    130                 135                 140

Met Thr Arg Gln Ser Leu Phe Gly Tyr Thr Leu Lys Glu Pro Ile Gly
145                 150                 155                 160

Val Val Gly Asn Ile Ile Pro Trp Asn Phe Pro Ser Ile Met Phe Ala
                165                 170                 175

Thr Lys Val Ala Pro Ala Met Ala Ala Gly Cys Thr Met Val Val Lys
            180                 185                 190

Pro Ala Glu Gln Thr Ser Leu Ser Ala Leu Phe Tyr Ala His Leu Ser
        195                 200                 205

Lys Glu Ala Gly Ile Pro Asp Gly Val Leu Asn Ile Val Thr Gly Phe
    210                 215                 220

Gly Ser Thr Ala Gly Ala Ala Ile Ala Ser His Met Asp Val Asp Lys
225                 230                 235                 240

Val Ser Phe Thr Gly Ser Thr Asp Val Gly Arg Lys Ile Met Gln Ala
                245                 250                 255

Ala Ala Ala Ser Asn Leu Lys Lys Val Ser Leu Glu Leu Gly Gly Lys
            260                 265                 270
```

```
Ser Pro Leu Leu Ile Phe Asn Asp Ala Asp Ile Asp Lys Ala Ala Asp
        275                 280                 285

Leu Ala Leu Leu Gly Cys Phe Tyr Asn Lys Gly Glu Ile Cys Val Ala
    290                 295                 300

Ser Ser Arg Val Phe Val Gln Glu Gly Ile Tyr Asp Lys Val Val Glu
305                 310                 315                 320

Lys Leu Val Glu Lys Ala Lys Asp Trp Thr Val Gly Asp Pro Phe Asp
                325                 330                 335

Ser Thr Ala Arg Gln Gly Pro Gln Val Asp Lys Arg Gln Phe Glu Lys
            340                 345                 350

Ile Leu Ser Tyr Ile Glu His Gly Lys Asn Glu Gly Ala Thr Leu Leu
        355                 360                 365

Thr Gly Gly Lys Ala Ile Gly Asp Lys Gly Tyr Phe Ile Gln Pro Thr
    370                 375                 380

Ile Phe Ala Asp Val Thr Glu Asp Met Lys Ile Tyr Gln Asp Glu Ile
385                 390                 395                 400

Phe Gly Pro Val Met Ser Leu Met Lys Phe Lys Thr Val Glu Glu Gly
                405                 410                 415

Ile Lys Cys Ala Asn Asn Thr Lys Tyr Gly Leu Ala Ala Gly Ile Leu
            420                 425                 430

Ser Gln Asp Ile Asp Leu Ile Asn Thr Val Ser Arg Ser Ile Lys Ala
        435                 440                 445

Gly Ile Ile Trp Val Asn Cys Tyr Phe Gly Phe Asp Leu Asp Cys Pro
    450                 455                 460

Tyr Gly Gly Tyr Lys Met Ser Gly Asn Cys Arg Glu Ser Gly Met Asp
465                 470                 475                 480

Ala Leu Asp Asn Tyr Leu Gln Thr Lys Ser Val Val Met Pro Leu His
                485                 490                 495

Asn Ser Pro Trp Met
            500

<210> SEQ ID NO 20
<211> LENGTH: 1506
<212> TYPE: DNA
<213> ORGANISM: Arabidopsis thaliana

<400> SEQUENCE: 20
atggagaacg gcaaatgcaa cggagccacg acggtgaagt taccggagat caaattcacc      60
aagcttttca tcaacggcca gttcattgat gctgcttcag ggaagacgtt tgagacgata     120
gaccctagga acggtgaagt gatcgcaaca atagccgaag agacaaaga agacgttgac      180 ttggccgtta acgctgcacg ttacgccttc gaccatggtc cttggcctcg catgaccggc     240
ttcgagaggg caaagcttat caacaaattc gcagacttaa tagaggaaaa cattgaggaa     300
ttggctaaac ttgatgcggt tgacggtgga aaattgtttc agttgggaaa atatgctgat     360
attccggcca cagccggtca ttttcgatac aatgcgggtg cagcagataa aatccacggc     420
gagactctta aaatgacgcg tcaatctttg ttcggataca ccctcaaaga accaattgga     480
gtggttggta atatcatccc ttggaatttc ccaagcatta tgtttgccac aaaggtggct     540
ccggctatgg ctgctggttg caccatggtg gtcaagccag ctgaacagac ttcactctct     600
gctttgttct atgcccatct ctcaaaagaa gcggaattc tgatggtgt gctcaacatt      660 gtaactggtt ttgatcaac tgctggagct gccattgcct cccatatgga cgtagacaaa     720
gttagtttca ctgggtcaac agatgttgga aggaagataa tgcaagccgc agccgcaagt     780
```

```
aatctcaaaa aagtttccct tgaattaggc gggaaatcgc cacttctcat attcaacgac    840
gctgatattg acaaagccgc cgatcttgcg cttctcggtt gcttttacaa caagggtgaa    900
atttgcgtgg cgagctctcg tgtgtttgtt caagaaggta tatacgataa ggttgtggag    960
aagttagtag agaaggctaa agattggacc gttggtgatc cttttgattc cactgctcga   1020
caaggacctc aagtggataa aagacagttt gagaagattc tatcttacat tgagcacggt   1080
aaaaacgaag gagcgacctt attaactgga ggaaaagcca ttggagacaa aggatatttc   1140
atccaaccaa ctatattcgc agatgtcact gaggatatga agatataccaa gatgaaatc   1200
tttggaccag tcatgtcact gatgaaattc aagacggtag aggaagggat caaatgcgca   1260
aacaacacga atacggtct tgcagcagga atactaagcc aagacataga cttgatcaac    1320
acggtttcga ggtcaatcaa agctggaatc atttgggtta attgctactt cgggtttgat   1380
cttgactgtc cttatggtgg ctacaagatg agtggtaatt gtcgtgaaag tggcatggac   1440
gctctcgaca actatctaca aaccaaatcc gtcgttatgc ctcttcacaa ttccccttgg   1500
atgtaa                                                              1506

<210> SEQ ID NO 21
<211> LENGTH: 1683
<212> TYPE: DNA
<213> ORGANISM: Penicillium simplicissimum

<400> SEQUENCE: 21
atgagtaaaa cccaagaatt tcgtccgctg accttacctc cgaaattaag cctgtcagat     60
tttaacgaat ttatacaaga catcataagg atagtgggta gcgagaacgt agaggttatc    120
agtagcaaag atcaaatcgt ggatggcagc tacatgaagc cgacccatac ccatgacccg    180
caccacgtta tggatcaaga ttattttctg caagcgcta tcgtcgcacc gcgtaacgtt     240
gcagacgttc aaagcattgt tggtctggca acaaattca gcttcccgct gtggccgatt     300
agcatcggtc gtaacagcgg ttacggtgga gcagcaccgc gtgttagcgg tagcgttgtt    360
ctcgatatgg gcaaaaacat gaatcgtgtt ctggaagtta atgtggaagg tgcctattgt    420
gttgttgaac cgggtgttac ctatcatgat ctgcataatt atctggaagc caataacctg    480
cgtgataagc tgtggctgga cgttccagac ctgggtggtg cagcgtact gggtaacgca     540
gtagaacgtg gagttggtta cacccgtat ggtgaccact ggatgatgca tagcggtatg     600
gaggttgtgc tggcaaacgg tgagctgctg cgtaccggta tgggtgcact gccagacccg    660
aagcgaccgg agacaatggg tctgaagccg gaggatcaac cgtggtcaaa gattgcacac    720
ctgtttccgt atggttttgg tccgtatatt gatggtctgt ttagtcagag caacatgggt    780
attgttacca aaattggcat ttggctgatg ccgaatccgg tggttatca gagctatctg     840
attaccctgc cgaaagatgg tgatctgaaa caggcagttg atattatccg tccgctgcgt    900
ctgggtatgg cactgcagaa tgttccgacc attcgtcata ttctgctgga tgccgcagtt    960
ctgggtgata acgtagcta tagcagtaaa accgaaccgc tgagtgatga agaactggat   1020
aaaattgcaa acagctgaa tctgggtcgc tggaacttt atggtgcact gtatggtccg    1080
gaaccgattc gtcgtgtgct gtgggaaacc attaaagatg catttagcgc aattccgggt   1140
gtgaaattct atttttccgga agatacaccg gaaaaattcag ttctgcgtgt tcgtgataaa   1200
accatgcagg gtattccgac ctatgatgaa ctgaaatgga ttgattggct gccgaatggt   1260
gcccacctct ttttagcccc gatagcaaaa gttagcggag aggacgcgat gatgcagtat   1320
gcagtgacca aaaaacgttg tcaagaagca ggtctggatt ttattggcac ctttaccgtt   1380
```

```
ggtatgcgtg aaatgcatca tattgtgtgc atcgtgttta acaaaaaaga cctgattcag    1440
aaacgcaagg ttcaatggct tatgcgtaca ctgatagacg attgcgcagc taacggttgg    1500
ggtgagtacc gtacacacct agcatttatg gatcagatca tggagacgta taattggaat    1560
aacagcagct ttctgcgctt taatgaagtt ctgaaaaatg ccgttgatcc gaatggtatt    1620
atcgcaccgg gtaaaagcgg cgtatggcct agccagtata gccacgtaac ctggaagcta    1680
taa                                                                  1683
```

<210> SEQ ID NO 22
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22

```
cgcagcagga ggttaag                                                   17
```